(12) United States Patent
Ylikoski et al.

(10) Patent No.: US 6,448,283 B1
(45) Date of Patent: Sep. 10, 2002

(54) METHODS FOR PREVENTING/TREATING DAMAGE TO SENSORY HAIR CELLS AND COCHLEAR NEURONS

(75) Inventors: Jukka Ylikoski; Ulla Pirvola, both of Kauniainen; Mart Saarma, Helsinki, all of (FI); Kevin M. Walton, Old Saybrook, CT (US); Robert L. Hudkins, Chester Springs, PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 09/404,187

(22) Filed: Sep. 24, 1999

Related U.S. Application Data
(60) Provisional application No. 60/101,763, filed on Sep. 25, 1998.

(51) Int. Cl.[7] ............................................... A01N 43/38
(52) U.S. Cl. ...................................................... 514/411
(58) Field of Search ........................................ 514/411

(56) References Cited

U.S. PATENT DOCUMENTS

| | | | | |
|---|---|---|---|---|
| 4,877,776 A | | 10/1989 | Murakata et al. | 514/43 |
| 4,923,986 A | | 5/1990 | Murakata et al. | 540/545 |
| 5,093,330 A | | 3/1992 | Caravatti et al. | 514/211 |
| 5,461,146 A | | 10/1995 | Lewis et al. | 540/545 |
| 5,468,872 A | | 11/1995 | Glicksman et al. | 548/416 |
| 5,475,110 A | | 12/1995 | Hudkins et al. | 546/256 |
| 5,516,771 A | | 5/1996 | Dionne et al. | 514/211 |
| 5,591,855 A | | 1/1997 | Hudkins et al. | 546/256 |
| 5,594,009 A | | 1/1997 | Hudkins et al. | 514/338 |
| 5,599,808 A | | 2/1997 | Goldstein et al. | 514/211 |
| 5,616,724 A | * | 4/1997 | Hudkins et al. | 548/417 |
| 5,621,100 A | * | 4/1997 | Lewis et al. | 540/545 |
| 5,621,101 A | * | 4/1997 | Lewis et al. | 540/545 |
| 5,705,511 A | * | 1/1998 | Hudkins et al. | 514/338 |
| 5,801,190 A | * | 9/1998 | Hudkins et al. | 514/410 |

FOREIGN PATENT DOCUMENTS

| | | |
|---|---|---|
| WO | WO 93/08809 | 5/1993 |
| WO | WO 97/30722 | 8/1997 |
| WO | WO 97/46565 | 12/1997 |
| WO | WO 97/49406 | 12/1997 |
| WO | WO 99/47522 | 9/1999 |

OTHER PUBLICATIONS

U.S. application No. 09/325,140, Singh et al., filed Jun. 3, 1999.*

U.S. application No. 60/119,834, Hudkins et al., filed Feb. 12, 1999.*

Jukka Ylikoski et al. "C–Jun phosphorylation by c–jun N–terminal kinase (JNK) mediates cochlear hair cell death induced by noise and neomycin, but not by cisplatin" ARO Abstracts vol. 24, 2001.

Basile et al., "N–Methyl–D–aspartate antagonists limit aminoglycoside antibiotic–induced hearing loss," Nature Med., 1996, 2(12), 1338–1343.

Behrens et al., "Amino–terminal phosphorylationof c–Jun regulates stress–induced apoptosis and cellular proliferation," Nature Gen., 1999, 21, 326–329.

Blank et al., "Acute Streptococcus pneumonide Meningogenic Labyrinthitis," Arch. Otol. Head Neck Surg., 1994, 120, 1342–1346.

Brady et al., "BDNF is a Target–Derived Survival Factor for Arterial Baroreceptor and Chemoafferent Primary Sensory Neurons," J. Neurosci., 1999, 19(6), 2131–2142.

Campbell et al., "D–Methionine provides excellent protection from cisplatin ototoxicity in the rat," Hear. Res., 1996, 102, 90–98.

Comis et al., "Cytotoxic Effects on Hair Cells of Guinea Pig Cochlea Produced by Pneumolysin, the Thiol Activated Toxin of Streptococcus pneumoniae," Acta Otolaryngol (Stockholm), 1993, 113(2), 152–159.

deGroot et al., "Co–administration of the neurotrophic ACTH$_{(4-9)}$ analogue, ORG 2766, may reduce the cochleotoxic effects of cisplatin," Hear. Res., 1997, 106, 9–19.

Dérijard et al., "JNK1: A Protein Kinase Stimulated by UV Light and Ha–Ras That Binds and Phosphorylates the c–Jun Activation Domain," Cell, 1994, 76, 1025–1037.

Dickens et al., "A Cytoplasmic Inhibitor of the JNK Signal Transduction Pathway," Science, 1997, 277, 693–696.

Ernfors et al., "Protection of auditory neurons from aminoglycoside toxicity by neurotrophin–3," Nature Med., 1996, 2(4), 463–467.

Ernfors et al., "Neurotrophins, NMDA Receptors, and Nitric Oxide in Development and Protection of the Auditory System," in Ototoxicity: Basic Science and Clinical Applications, Annals of the New York Academy of Sciences, 1999, vol. 884, 131–142.

Estus et al., "Altered Gene Expression in Neurons during Programmed Cell Death: Identification of c–jun as Necessary for Neuronal Apoptosis," J. Cell Biol., 1994, 127(6:1), 1717–1727.

Forge, "Outer hair cell loss and supporting cell expansion following chronic gentamicin treatment," Hear. Res., 1985, 19, 171–182.

Gabaizadeh et al., "Protection of Both Auditory Hair Cells and Auditory Neurons from Cisplatin Induced Damage," Acta Otolaryngol (Stockholm), 1997, 117, 232–238.

Gao et al., "Neurotrophin–3 Reverses Experimental Cisplatin–induced Peripheral Sensory Neuropathy," Ann. Neurol., 1995, 38(1), 30–37.

(List continued on next page.)

Primary Examiner—Zohreh Fay
(74) Attorney, Agent, or Firm—Woodcock Washburn LLP

(57) ABSTRACT

Methods for preventing or treating damage to sensory hair cells and cochlear neurons are disclosed. The methods comprise the administration of an effective amount of a compound of Formula I or Formula II. The method provides for the prevention/treatment of both hearing loss and loss of the sense of balance.

12 Claims, 13 Drawing Sheets

OTHER PUBLICATIONS

Garetz et al., "Attenuation of gentamicin ototoxicity by glutathione in the guinea pig in vivo," *Hear. Res.*, 1994, 77, 81–87.

Ham et al., "A c–Jun Dominant Negative Mutant Protects Sympathetic Neurons against Programmed Cell Death," *Neuron*, 1995, 14, 927–939.

Hawkins, J.E., "Drug Ototoxicity," in *Handbook of Sensory Physiology*., Keidel, W. et al. (eds.), Springer, New York, 1976, vol. V/3, 707–748.

Hu et al., "R–phenylisopropyladenosine attenuates noise–induced hearing loss in the chinchilla," *Hear. Res.*, 1997, 113, 198–206.

Hulka et al., "Use of Poly–L–Aspartic Acid to Inhibit Aminoglycoside Cochlear Ototoxicity," *Am. J. Otol.*, 1993, 14(4), 352–356.

Johnsson et al., "Speech understanding and aging," *J. Acoust. Soc. Am.*, 1988, 83(3), 859–895.

Johnsson et al., "Sensory and Neural Degeneration with Aging, as Seen in Microdissections of the Human Inner Ear," *Ann. Otol.*, 1972, 81, 179–193.

Johnsson et al., "Vascular Changes in the Human Inner Ear Associated with Aging," *Ann. Otol.*, 1972, 81, 364–376.

Kaltenbach et al., "Comparison of five agents in protecting the cochlea against the ototoxic effects of cisplatin in the hamster," *Otol. Head Neck Surg.*, 1997, 117(5), 493–500.

Keithley et al., "GDNF protects the cochlea against noise damage," *NeuroReport*, 1998, 9(10), 2183–2187.

Kellerhals, "Acoustic Trauma and Cochlear Microcirculation," in *Advances Oto–Rhino– Laryngology*, 1972, 18, 91–168.

Korver et al., "Round window application of D–methionine provides cisplatin otoprotection," 21st Midwinter Research Meeting of ARO, St. Petersburg, Florida, Feb. 15–19, 1998, Abstract No. 536, Session R3, 1 page.

Kyriakis et al., "The stress–activated protein kinase subfamily of c–Jun kinase," *Nature*, 1994, 369, 156–160.

Lang et al., "Apoptosis and hair cell degeneration in the vestibular sensory epithelia of the guinea pig following a gentamicin insult," *Hearing Res.*, 1997, 111, 177–184.

Leary, "Restoring Hearing, After Too Much Noise," *New York Times, Health*, Sep. 1, 1998.

Leclere, P. et al., "Effects of Glial Cell Line–Derived Neurotrophic Factor on Axonal Growth and Apoptosis in Adult Mammalian Sensory Neurons In Vitro," *Neurosci.*, 1997, 82(2), 545–558.

Li et al., "Two Modes of Hair Cell Loss from the Vestibular Sensory Epithelia of the Guinea Pig Inner Ear," *J. Comparative Neur.*, 1995, 355, 405–417.

Liu et al., "Caspase inhibitors prevent cisplatin–induced apoptosis of auditory sensory cells," *NeurReport*, 1998, 9, 2609–2614.

Low et al., "Basic Fibroblast Growth Factor (FGF–2) Protects Rats Cochlear Hair Cells in Organotypical Culture From Aminoglycoside Injury," *J. Cell Physiol.*, 1996, 167, 443–450.

Malgrange et al., "Transforming growth factor alpha (TGFa) acts with retinoic acid to protect auditory hair cells from ainoglycoside induced ototoxicity," *Abstracts of the Seventh Annual MidWinter Research Meeting of the ARO*, St. Petersburg Beach, Florida, Popelka, G.R., Ph.D. (ed.), Feb. 6–10, 1994, p. 138, Abstract No. 551.

Maroney et al., "Motoneuron Apoptosis is Blocked by CEP–1347 (KT 7515), a Novel Inhibitor of the JNK Singaling Pathway," *J. Neuroscience*, 1998, 18(91), 104–111.

Moody et al., "Synthesis of the Staurosporine Aglycon," *J. Org. Chem.*, 1992, 57, 2105–2114.

Nakagawa et al., "Gentamicin ototoxicity induced apoptosis of the vestibular hair cells of guinea pigs," *Eur. Arch. Otor.*, 1997, 254, 9–14.

Nakagawa et al., "Apoptosis of guinea pig cochlear hair cells following chronic aminoglycoside treatment," *Eur. Arch. Otorhinolaryngol.*, 1998, 255, 127–131.

Nakagawa et al., "Two Modes of Auditory Hair Cell Loss following Acoustic Overstimulation in the Avian Inner Ear," *ORL*, 1997, 59, 303–310.

Osborne et al., "The cochlear lesion in experimental bacterial meningitis of the rabbit," *Int'l. J. Exp. Pathol.*, 1995, 76(5), 317–330.

Paparella et al. (eds.), "Chemical and Drug Effects on the Inner Ear," in *Otolaryngology*, Second Edition, 1980, vol. 2, 1817.

Pettmann et al., "Neuronal Cell Death," *Neuron*, 1998, 20, 633–647.

Pirvola et al., "Coordinated expression and function of neurotrophins and their receptors in the rat inner ear during target innervation," *Hearing Res.*, 1994, 75, 131–144.

Quirk et al., "Lipid peroxidation inhibitor attenuates noise–induced temporary threshold shifts," *Hear. Res.*, 1994, 74, 217–220.

Ravi et al., "Mechanism of Cisplatin Ototoxicity: Antioxidant System," *Pharm. Toxicol.*, 1995, 76, 386–394.

Schuknecht, "Further Observations on the Pathology of Presbycusis," *Arch. Otol.*, 1964, 80, 369–382.

Shoji et al., "GDNF protects hair cell from noise damage," 21st Midwinter Research Meeting of ARO, St. Petersburg, Florida, Feb. 15–19, 1998, Abstract No. 539, Session R3, 1 page.

Song et al., "Protection from Gentamicin Ototoxicity by Iron Chelators in Guinea Pig In Vivo," *J. Pharmacol. Exp. Therapeutics*, 1997, 282(1), 369–377.

Tay et al., "In vivo protection of auditory hair cells from gentamicin ototoxicity by intracochlear administration of GDNF," 21st Midwinter Research Meeting of ARO, St. Petersburg, Florida, Feb. 15–19, 1998, Abstract No. 538, Session R3, 1 page.

Thurmond et al., "Sudden Sensorineural Hearing Loss: Etiologies and Treatments," *J. La. State Med. Soc.*, 1998, 150, 200–203.*

Vago et al., "Amikacin intoxication induces apoptosis and cell proliferation in rat organ of Corti," *NeuroReport*, 1998, 9, 431–436.*

Watson et al., "Phosphorylation of c–Jun is Necessary for Apoptosis Induced by Survival Signal Withdrawal in Cerebellar Granule Neurons," *J. Neurosci.*, 1998, 18(2), 751–762.*

Winter et al., "Ultrastructural Damage to the Organ of Corti during Acute Experimental *Escherichia coli* and Pneumococcal Meningitis in Guinea Pigs," *Acta. Otolaryngol (Stockholm)*, 1996, 116(3), 401–407.*

Xia et al., "Opposing Effects of ERK and JNK–p38 MAP Kinases on Apoptosis," *Science*, 1995, 270, 1326–1331.*

Yamasoba et al., "Chronic strychnine administration into the cochlea potentiates permanent threshold shift following noise exposure," *Hear. Res.*, 1997, 112, 13–20.*

Yang et al., "Absence of excitotoxicity–induced apoptosis in the hippocampus of mice lacking the Jnk3 gene," *Nature*, 1997, 389, 865–870.*

Ylikoski et al., "Expression patterns of neurotrophin and their receptor mRNAs in the rat inner ear," *Hear. Res.*, 1993, 65, 69–78.*

Ylikoski, "Guinea–Pig Hair Cell Pathology from Ototoxic Antibiotics" *Acta. Otolaryngol.* (*Stockholm*), 1974, Suppl. 326, 5–22.*

Ylikoski et al., "Guinea pig auditory neurons are protected by glial cell line–derived growth factor from degeneration after noise trauma," *Hear. Res.*, 1998, 124, 17–26.*

*Remington's Sciences*, 17th ed., Mack Publishing Co., Easton, PA, 1985.*

Green and Wuts, P.G.M., *Protective Groups in Organic Synthesis*, 2d. Ed., Wiley & Sons, 1991.*

* cited by examiner

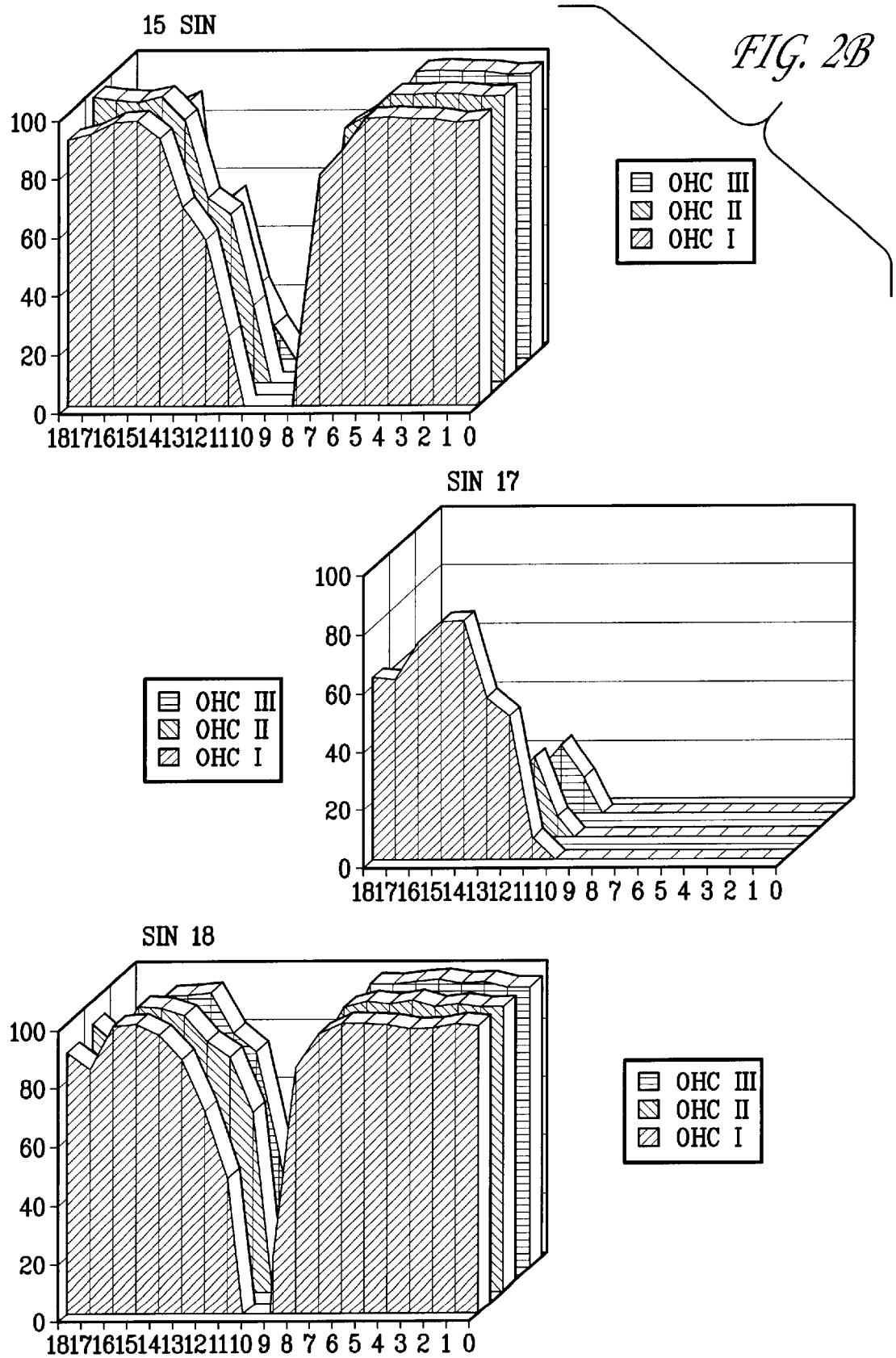

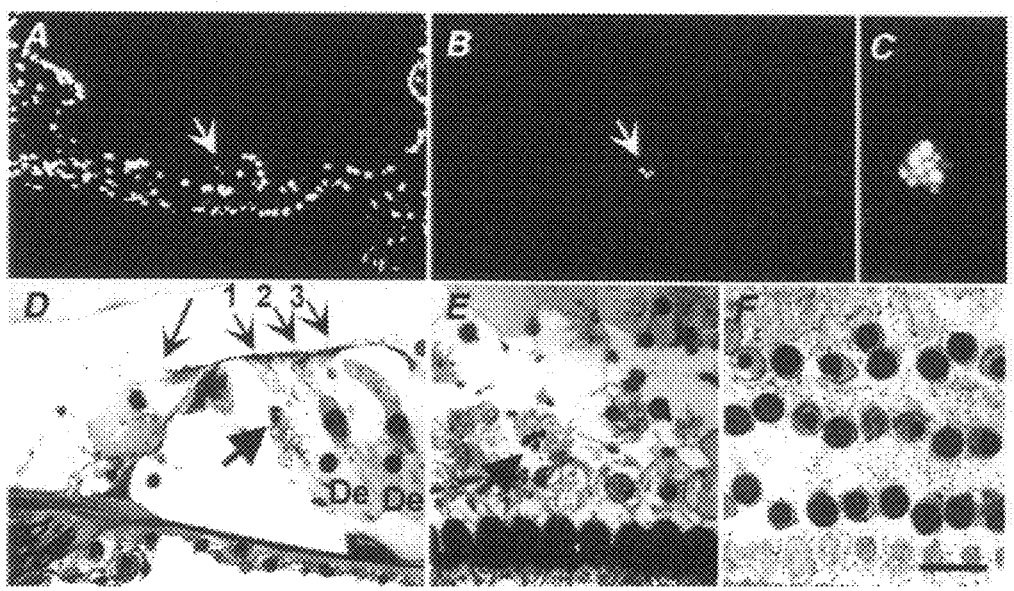

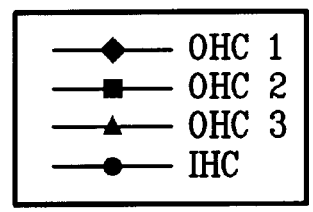
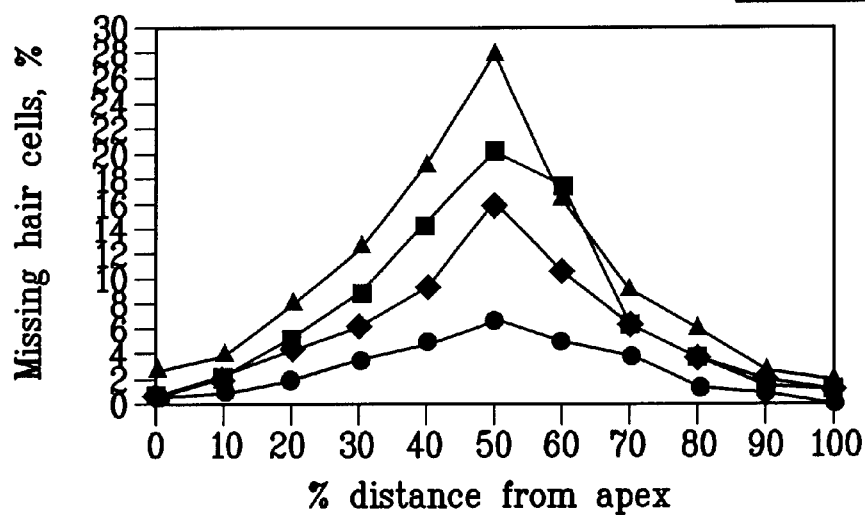
FIG. 5A
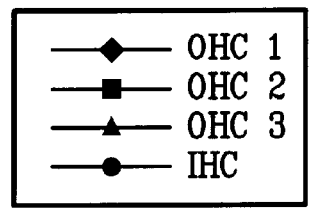
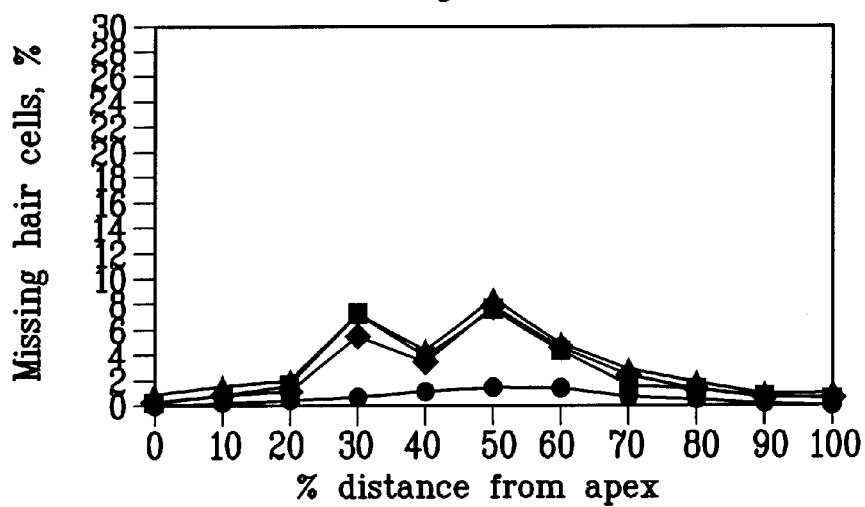
FIG. 5B

METHODS FOR PREVENTING/TREATING DAMAGE TO SENSORY HAIR CELLS AND COCHLEAR NEURONS

CROSS-REFERENCE TO RELATED APPLICATION

This application claims the benefit of U.S. Provisional Application Ser. No. 60/101,763, filed Sep. 25, 1998, the disclosure of which is hereby incorporated herein by reference, in its entirety.

TECHNICAL FIELD OF THE INVENTION

The present invention provides methods for preventing and/or treating hearing loss and loss of the sense of balance. More specifically, the present invention provides methods for preserving sensory hair cells and cochlear neurons in a subject by administering an effective amount of compounds of Formula I and/or Formula II.

BACKGROUND OF THE INVENTION

The mammalian ear functions by transforming sound waves, or airborne vibrations, into electrical impulses. The brain then recognizes these electrical impulses as sound. The ear has three major parts, the outer, middle, and inner ear. Sound waves enter the outer ear and cause the eardrum to vibrate. The vibrations of the eardrum are transmitted serially through the three ossicles in the middle ear- the malleus, incus and stapes, also called the hammer, anvil and stirrup, respectively. The stirrup transmits the vibrations to the inner ear. The inner ear comprises the cochlea and is connected to the middle ear via the oval and round windows. The inner ear is filled with fluid and vibrations transmitted to the inner ear cause fluid movement in the cochlea of the inner ear. Fluid movement in the cochlea causes movement of sensory hair cells which initiates nerve impulses. These nerve impulses are interpreted in the brain as sound.

The sensory hair cells are contained in the organ of Corti, which coils around the inside of the cochlea. Within the organ of Corti there are inner and outer sensory hair cells. The outer sensory hair cells are present in three rows, designated OHC1, OHC2 and OHC3; inner sensory hair cells are present in one row. The sensory hair cells are attached to the basilar membrane and contact the tectorial membrane. Movement of fluids within the inner ear causes a movement of the basilar membrane relative to the tectorial membrane. This relative movement causes the cilia on the sensory hair cells to bend and leads to electrical activity. Cochlear ganglion neurons below the sensory hair cells transmit this electrical activity to auditory regions of the brain via the auditory nerve.

The fluid filled inner ear, also called the membranous labyrinth, further contains the two mammalian organs of equilibrium which make up the vestibular system. The first organ of equilibrium is composed of the saccule and utricle which detect and convey information on body position relative to gravitational force. Both the saccule and utricle also contain sensory hair cells. Tiny particles of calcium carbonate lie on the sensory hair cells in the saccule and utricle and bend the cilia to stimulate the sensory hair cells to send appropriate signals to the brain, including "up", "down", "tilt" and "acceleration" in a particular direction. Sensory hair cells in the utricle detect linear movement in the horizontal plane while sensory hair cells in the saccule detect movement in the vertical plane.

The second organ of equilibrium is composed of three semicircular canals which detect and convey information on movement, detected as fluid acceleration, to the brain. The semicircular canals are also lined with sensory hair cells, and are arranged at near 90 degree angles with respect to one another and can detect movement in three dimensions. As the head is accelerated in one of these planes, fluid movement in the canal corresponding to the plane of movement stimulates movement of the cilia of the sensory hair cells.

The vestibular organs—the saccule, the utricle and the semicircular canals —stimulate nerve endings of vestibular ganglion neurons which then transmit information to a number of sites for different purposes. For example, information is transmitted from the vestibular system to the eyes to keep the eyes focused on a target while the body is moving. Neurons also interconnect the vestibular system and the cerebellum for producing smooth and coordinated bodily movements. Vestibular information also travels down the spinal cord to muscles in order to maintain proper posture and balance.

Significant hearing loss causing communication problems occurs in about ten percent of the population and more than one third of us will have substantial hearing loss by old age. Noise-induced hearing loss is estimated to be the cause of hearing loss in about one-third of the 28 million Americans with hearing loss (NIH Publication No. 97–4233, April 1997). In most cases, the auditory impairment results from the death of sensory hair cells in the organ of Corti. Sensory hair cells are delicate cells and thus are susceptible to damage from several sources, including, but not limited to, noise, infection, drugs, vascular insufficiency and idiopathic effects. Idiopathic effects are those effects which arise spontaneously or from an unknown or obscure cause.

Presbycusis is age-related hearing loss. Four distinct types of presbycusis have been described which are based upon audiograms and pathological analyses: 1) sensory—loss of sensory hair cells and secondary degeneration of cochlear neuronal structures, 2) neural—loss of cochlear ganglion cells and/or nerve, 3) metabolic—atrophy of the *stria vascularis*, and 4) mechanical—stiffening of the basilar membrane (Schuknecht, Arch. Otol., 80:369–382, 1964). The neural and metabolic causes of presbycusis may also result in the ultimate loss of hair cells.

While no frequency data is associated with the descriptions of the types of presbycusis, sensory presbycusis is the most common (Working Group on Speech Understanding and Aging, Speech understanding and aging, J. Acoust. Soc. Am. 83:859–895, 1988). Johnsson et al. have described both degeneration of the *stria vascularis* and hair cell loss in 150 patients ranging in age from newborn to 97 years of age. Both are progressive and most pronounced in elderly subjects. An age-related loss of hair cells of the vestibular apparatus—saccule and utricle—was also noted that may account for vestibular disturbances in the elderly (Johnsson et al., Ann. Otol. Rhinol. Laryngol. 81:179–193, 1972; Johnsson et al., Ann. Otol. Rhinol. Laryngol. 81:364–376, 1972).

We are born with a complement of about 16,000 sensory hair cells and 30,000 auditory neurons in each ear. These cells do not regenerate during postnatal life. Therefore, loss of each cell, due to, for example, noise, infection, toxic drugs (such as platinum-based cytotoxic agents and aminoglycosides) or idiopathic effects is irreversible and cumulative. If enough sensory cells are lost, the end result can be total deafness.

Noise trauma is a widespread cause of hearing loss. Sound overexposure has been demonstrated to lead to sensory hair cell apoptosis in the avian inner ear (Nakagawa et al., ORL, 59:303–310, 1997). There is increasing evidence that the death of sensory hair cells caused by drugs such as platinum-based cytotoxic agents and aminoglycosides is partially, if not mainly, apoptotic. Noise-induced sensory hair cell loss in the cochlea apparently has a similar mechanism.

Aminoglycosides are widely used antibiotics used in patients with Gram-negative bacterial infections (Paparella et al, Otolaryngology, 1817, Saunders-Philadelphia, 1980). Aminoglycosides are known to cause damage to sensory hair cells and thereby affect hearing. Aminoglycosides include, but are not limited to, neomycin, kanamycin, amikacin, streptomycin and gentamicin. Amikacin causes apoptosis of sensory hair cells in rat cochleas (Vago et al., NeuroReport 9:431–436, 1998). Gentamicin treatment results in degeneration of sensory hair cells in guinea pigs (Li et al., J. Comparative Neur., 355:405–417, 1995; Lang et al., Hearing Res., 111:177–184, 1997).

The loss of sensory hair cells in the cochlea has been attributed to aminoglycoside ototoxicity. Apoptosis of sensory hair cells of guinea pigs was observed following chronic treatment with aminoglycoside (Nakagawa et al., Eur. Arch. Otor., 254:9–14, 1997; Nakagawa et al., Acta Otol., 255(3):127–131, 1998). Studies have assessed the protective effect of various polypeptides on sensory hair cells in the cochlea. (See, for example, Malgrange et al., Abstr. Assoc. Res. Otol., 17:138, 1994; Low et al., J. Cell. Physiol. 167:443–450, 1996; and Ernfors et al., Nature Medicine, 2:463–467, 1996). Ernfors et al. noted that, although the peptide NT-3 is a potent factor for preventing the degeneration of spiral ganglion neurons, NT-3 "insufficiently protects the hair cells" (Ernfors et al., Nature Medicine, 2:463–467, 1996).

Platinum-based cytotoxic agents include, but are not limited to, cisplatin and carboplatin. Cisplatin is a widely used antitumor drug which causes structural changes in the inner ear and peripheral sensory neuropathy. Hearing loss due to cisplatin is usually permanent and cumulative.

Rapid onset hearing loss, also named sudden sensorineural hearing loss, may also occur without any obvious reasons. Hearing loss in these situations develops either instantaneously or after a few hours. The location of the damage is within the cochlea, and has been partially attributed to sensory hair cell damage. Such hearing loss may be due to idiopathic causes or as a result of other causes, including vascular disease, hypertension and thyroid disease and viral infection by viruses including mumps, measles, mononucleosis, adenovirus, (Thurmond et al., J. La. State Med. Soc., 150:201–203, 1998).

Damage to sensory hair cells and cochlear neurons may also occur as a result of infection. For example, the onset of meningitis has been linked to hearing loss as a result of damage to sensory hair cells. (Blank et al., Arch. Otol. Head Neck Surg., 120:1342–1346, 1994). Meningitis as a result of E. Coli infection also damages sensory hair cells (Marwick et al., Acta Otol. (Stockholm), 116(3):401–407, 1996). Toxins from Streptococcus pneumoniae have also been linked to damage to sensory hair cells (Comis et al., Acta Otol. (Stockholm) 113(2):152–159, 1993).

Accessory epithelial structures of the cochlea and innervating cochlear neurons stay intact for a considerable length of time following trauma, but undergo secondary retrograde degeneration following the loss of IHCs (Ylikoski et al., 1974; Hawkins, 1976).

Several authors have recently shown that the cochlear sensory hair cells can be protected to some extent from both ototoxic and noise damage using various compounds. This was shown in animal model systems using hair cell counts and hearing threshold measurements, e.g. by auditory brainstem responses. The most commonly used therapeutic compounds have been antioxidants or free radical scavengers.

In addition to immediate mechanical damage, oxidative stress associated with the formation of free radicals (see discussion) and excitotoxicity (Basile et al., Nature Med. 2:1338–1343, 1996) have been implicated in the pathogenesis of hearing loss. Evidence in various cell lines and in vivo neuronal and non-neuronal model systems shows that apoptotic death can be induced by both oxidative stress and excitotoxicity (reviewed by Pettmann and Henderson, Neuron 20:633–647, 1998). In the inner ear, necrotic hair cell death, characterized by cellular swelling, has been demonstrated following acoustic trauma (Kellerhals, Adv. Oto-Rhino. Laryng. 18:91–168, 1972). More recent data, obtained in the ototoxic drug-damaged inner ear, have suggested that hair cells may also die through apoptosis, based on the observations of nuclear fragmentation (Forge, Hear. Res. 19:171–182, 1985; Lee et al. J. Comp. Neur., vol.355, 405–417, 1995;

Liu et al., Neuroreport 9:2609–2614, 1998; Nakagawa et al., Eur. Arch.

Otorhinolaryngol. 255:127–131, 1998; Vago et al., NeuroReport 9:431–436, 1998). However, the contribution of apoptotic hair cell death to the loss of hearing function is not known. In addition, the molecular mechanisms involved in commitment to hair cell death are unknown.

Antioxidants and free radical scavengers have been tested because both ototoxic drug and noise damage have been postulated to produce an excess of reactive oxygen species (ROS) in the inner ear. Overproduction of ROS is thought to cause sensory hair cell damage by overwhelming the cochlea's antioxidant defense system (Ravi et al., Pharmacology and Toxicology 76:386–394, 1995).

One of the signaling cascades that has been shown to mediate apoptotic death in response to a variety of stressful stimuli is the c-Jun-N-terminal kinase (JNK) pathway, also known as the stress-activated protein kinase (SAPK) pathway (Dérijard et al., Cell 76:1025–1037, 1994; Kyriakis et al., Nature 369:156–160,1994). JNK activation by phosphorylation has been shown to be important for neuronal cell death after trophic factor withdrawal in vitro and after injury in vivo (Xia et al., Science 270:1326–1331, 1995; Dickens et al., Science 277:693–696, 1997; Yang et al., Nature 389:865–870, 1997). JNKs in turn phosphorylate c-Jun, a component of the transcription factor AP-1. Blockade of c-Jun activation and transcriptional activity in vitro has been shown to prevent neuronal cell death (Estus et al., J. Cell Biol. 127:1717–1727, 1994; Ham et al., Neuron 14:927–939, 1995; Watson et al., J. Neurosci. 15:751–762, 1998). Recent data from c-Jun phosphorylation-deficient mice (Behrens et al., Nature Gen. 21:326–329, 1999) and from JNK knock-out mice (Yang et al., 1997) show that c-Jun phosphorylation is essential for injury-induced neuronal death.

Neurotrophic factors including NT-3, BDNF and GDNF have also been shown to be important for protection of neurons within the inner ear, and may also have a role in hair cell protection after cochlear insult (Gabaizadeh et al., Acta Otol. (Stockholm), 117:232–235, 1997; Ernfors et al. Ototoxicity: Basic Research and clinical applications, Savelletri di Fasano, Italy, Jun. 18–20, 1998, Abstract No. 12; Keithley et al., Neuroreport, 9:(10), 2183–2187, 1988; Shoji et al., ARO Meeting, St. Petersburg Beach, Fla., Abstract No.539, 1998; Tay et al., ARO Meeting, St. Petersburg Beach, Fla., Abstract No.538, 1998; Ylikoski et al., Hear Res 124:17–26, 1998). The loss of mechanoreception following cisplatin-induced neuropathy has been reversed through the administration of NT-3 (Gao et al., Ann. Neurol., 38:30–37, 1995).

Table 1, below, summarizes some compounds tested for protection of cochlear sensory hair cells from damage, in vivo.

TABLE 1

| TEST COMPOUND | TYPE OF LESION | REFERENCE |
|---|---|---|
| antioxidants/free oxygen scavengers | | |
| Lipid peroxidation inhibitor | noise | Quirk et al., 1994[1] |
| R-phenylisopropanyl-adenosine | noise | Hu et al., 1997[2] |
| Glutathione | gentamicin | Garetz et al., 1994[3] |
| Glutathione | noise | Yamasoba et al., 1998[4] |
| D-methionine | cisplatin | Campbell et al, 1996[5] |
| D-methionine (+BDNF) | cisplatin | Gabaizadeh et al., 1997, supra. |
| Na-thiosulfate (STS) | cisplatin | Kaltenbach et al., 1997[6] |
| neurotrotrophic factors | | |
| BDNF (+D-methionine) | cisplatin | Gabaizadeb et al., 1997, supra. |
| NT-3 + MK801 | noise, amikacin | Emfors et al., 1998, supra. |
| GDNF | cisplatin | Tay et al., 1998, supra. |
| GDNF | gentamicin | Shoji et al., 1998, supra. |
| GDNF | noise | Keithley et al., 1998, supra. |
| others | | |
| NMDA antagonists (MK801,ifenprodil) | aminoglycosides | Basile et al., 1996[7] |
| ORG 2766 (ACTH analogue) | cisplatin | DeGroot et al., 1997[8] |
| Iron chelators | gentamicin | Song et al., 1997[9] |
| poly-1-aspartic acid | gentamicin | Hulka et al., 1993[10] |

Notated references from Table 1 (not cited previously).
[1]Quirk et al., Hear. Res., 74: 217–220, 1994.
[2]Hu et al., Hear. Res., 113: 198–206, 1997.
[3]Garetz et al., Hear. Res., 77: 81–87, 1994.
[4]Yamasoba et al., Hear. Res., 784: 82–90, 1998.
[5]Campbell et al., Hear. Res., 102: 90–98, 1996.
[6]Kaltenbach et al., Otol. Head Neck Surg., 117: 493–500, 1997.
[7]Basile et al., Nat. Med., 2: 1338–1343, 1996.
[8]DeGroot et al., Hear. Res., 106: 9–19, 1997.
[9]Song et al., J. Pharmacol. Exp. Therapeutics, 282: 369–377, 1997.
[10]Hulka et al., Am. J. Otol., 14: 352–356, 1993.

One problem in drug-based therapy of cochlear lesions is the limited biological activity of exogenously administered polypeptides. The biological half-life of many neurotrophic factors has been shown to be very short. On the other hand, degeneration of sensory hair cells does not occur instantly; a large number of sensory hair cells at first seem to be reversibly damaged and might recover if treated promptly. After noise exposure, the typical pattern of cellular damage in the organ of Corti takes 2–3 weeks to be complete. Affected cochlear neurons start to degenerate after noise has destroyed the sensory hair cells and the nerve terminals, 3–4 weeks postexposure.

There is no effective medical treatment to date for auditory sensory hair cell loss. Also, prevention of sensory hair cell degeneration is obscured by the fact that exact molecular mechanisms of damage to the auditory organ are unknown. Consequently, no effective regimen has been developed to prevent or treat damage to sensory hair cells. Therefore, there exists a need for compositions and methods to prevent and/or treat sensory hair cell damage.

There is also no effective medical treatment known to date for loss of cochlear neurons. Therefore, a need exists for compositions and methods to prevent and/or treat damage or loss of cochlear neurons.

As is clear from the foregoing discussion, damage to sensory hair cells or cochlear neurons can also affect the vestibular system and can result, for example, in vertigo. Benign paroxysmal positional vertigo (BPPV) affects about 40 to 60 people per 100,000 population every year. Also, Meniere's disease affects about 40 people per 100,000 population each year. During the course of these and other diseases, the sensory hair cells of the vestibular system have a tendency to degenerate. No effective regimen to date has been developed to prevent or treat damage to sensory hair cells in the vestibular system. Therefore, there exists a need for compositions and methods to prevent and/or treat damage to sensory hair cells and neurons in the vestibular system.

SUMMARY OF THE INVENTION

According to one aspect of the invention, a method is provided for preventing hearing loss in a subject comprising administering to said subject an effective amount of a fused pyrrolocarbazole of Formula I having the formula:

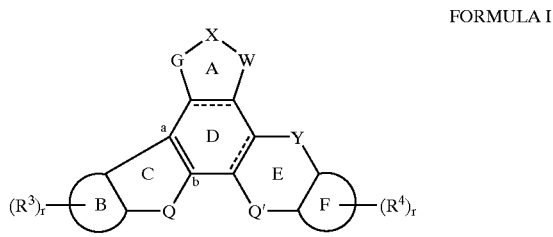

FORMULA I or a stereoisomer or pharmaceutically acceptable salt form thereof, wherein:

ring D is selected from phenyl and cyclohexene with double bond a–b;

ring B and ring F are independently selected from:
   (a) a 6-membered carbocyclic ring in which from 1 to 3 carbon atoms may be replaced by heteroatoms;
   (b) a 5-membered carbocyclic ring; and
   (c) a 5-membered carbocyclic ring in which either:
      (1) one carbon atom is replaced with an oxygen, nitrogen, or sulfur atom;
      (2) two carbon atoms are replaced with a sulfur and a nitrogen atom, an oxygen and a nitrogen atom, or two nitrogen atoms; or
      (3) three carbon atoms are replaced with three nitrogen atoms, one oxygen and two nitrogen atoms, or one sulfur and two nitrogen atoms;

G-X-W is selected from:
   (a) $(Z^1Z^2)C-N(R^1)-C(Z^1Z^2)$;
   (b) $CH(R^1)-C(=O)-N(R^1)$; and
   (c) $N(R^1)-C(=O)-CH(R^1)$;

$Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;

R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR^{1b}$, optionally substituted arylalkyl and optionally substituted heteroarylalkyl;

$R^1$ is independently selected from:
  (a) H, optionally substituted alkyl, optionally substituted aryl, optionally substituted arylalkyl, optionally substituted heteroaryl and optionally substituted heteroarylalkyl;
  (b) $C(=O)R^{1a}$;
  (c) $OR^{1b}$;
  (d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$, $R^{1a}$ is independently selected from optionally substituted alkyl, optionally substituted aryl and optionally substituted heteroaryl;

$R^{1b}$ is independently selected from H and optionally substituted alkyl;

$R^{1c}$ and $R^{1d}$ are each independently selected from H, optionally substituted alkyl and a linking group of the formula $(CH_2)_2$—$X^1$—$(CH_2)_2$;

$X^1$ is independently selected from O, S and $CH_2$;

Q is selected from $NR^2$, 0, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;

$R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;

$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;

$R^{2b}$ is selected from H and optionally substituted alkyl;

$R^{2c}$ and $R^{2d}$ are each independently selected from H and optionally substituted alkyl, or together form a linking group of the formula $(CH_2)_2$—$X^1$—$(CH_2)_2$;

$R^3$ and $R^4$ are each independently selected from:
  (a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
  (b) $CH_2OR^{14}$;
  (c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
  (d) $S(O)_yR^9$, $(CH_2)_pS(O)_yR^9$ and $CH_2S(O)_yR^{14}$;
  (e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2$—$X^1$—$(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
  (a) a direct bond;
  (b) optionally substituted $CH_2$, $CH_2CH_2$ or $CH_2CH_2CH_2$, wherein said optional substituents are one to about three $R^{19}$ groups; and
  (c) $CH=CH$, $CH(OH)$—$CH(OH)$, O, S, $S(=O)$, $S(=O)_2$, $C(R^{18})_2$, $C=C(R^{19})_2$, $C(=O)$, $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2$—$X^1$—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
  (a) a direct bond;
  (b) $NR^6$;
  (c) optionally substituted $CH_2$, $CH_2CH_2$ or $CH_2CH_2CH_2$;
  (d) $CR^{22}R^{24}$; and
  (e) $CH=CH$, $CH(OH)CH(OH)$, O, S, $S(=O)$, $S(=O)_2$, $C(=O)$, $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, $Z'$—$CH_2$ and $CH_2Z'CH_2$;

$Z'$ is selected from $C(R^{11})(OR^{12})$, O, S, $C(=O)$, $C(=NOR^{11})$ and $NR^{11}$;

$R^6$ is selected from H, $SO_2R^{2a}$, $CO_2R^{2c}$ $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

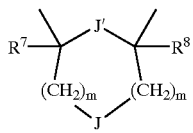

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2—X^3—CH_2$;

$X^3$ is a bond, O, S, or $NR^{10}$;

J is selected from a bond, O, CH=CH, S, C(=O), $CH(OR^{10})$, $N(OR^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

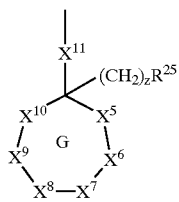

$X^5$ and $X^6$ are independently selected from O, N, S, $CHR^{26}$, $C(OH)R^{26}$, C(=O) and $CH_2=C$;

$X^7$ and $X^8$ are independently selected from a bond, O, N, S, $CHR^{26}$, $C(OH)R^{26}$, C(=O) and $CH_2=C$;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein
  (1) ring G contains 0 to about 3 ring heteroatoms;
  (2) any two adjacent hydroxyl groups of ring G can be joined to form a dioxolane ring;
  (3) any two adjacent ring carbon atoms of ring G can be joined to form a fused aryl or heteroaryl ring; with the provisos that:
    (a) when $X^{11}$ is a bond, ring G can be heteroaryl; and
    (b) ring G:
      (i) contains at least one carbon atom that is saturated;
      (ii) does not contain two adjacent ring O atoms;
      (iii) contains a maximum of two C(=O) groups;

$R^{27}$ is selected from H and alkyl;

$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;

$R^{29}$ is selected from alkyl, aryl and heteroaryl;

$R^{30}$ is selected from H, alkyl, acyl and $C(=O)NR^{11}R^{12}$;

m is independently selected from 0, 1, and 2;

p is independently selected from 1, 2, 3, and 4;

r is independently selected from 0, 1, and 2;

y is independently selected from 0, 1 and 2; and z is selected from 0, 1, 2, 3 and 4;

with the provisos that at least one of Y and Q' is a direct bond, when Y is a direct bond, Q' is other than a direct bond, when Q' is a direct bond, Y is other than a direct bond, and when rings B and F are phenyl, G-X-W is $CH_2NHC(=O)$, Y is a direct bond, Q is $NR^2$ and Q' is $NR^6$ where $R^6$ is joined with $R^2$ to form

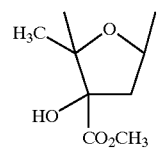

then $R^3$ is other than $CH_2SCH_2CH_3$.

Another aspect of the invention provides a method for preventing loss of sense of balance in a subject comprising administering to said subject an effective amount of a fused pyrrolocarbazole of Formula I, as defined above.

Yet another aspect of the invention provides a method for preventing the death of sensory hair cells in a subject comprising administering an effective amount of the compound of Formula I, as defined above.

A further aspect of the invention provides a method for preventing sudden sensorineural hearing loss due to the loss of sensory hair cells comprising administering an effective amount of the compound of Formula I, as defined above.

Another aspect of the invention provides a method for preserving function of sensory hair cells prior to or subsequent to trauma in a subject comprising administering an effective amount of the compound of Formula I, as defined above.

Yet another aspect of the invention provides a method for treating damaged sensory hair cells comprising administering an effective amount of the compound of Formula I, as defined above.

A further aspect of the invention provides a method for preventing death of cochlear neurons in a subject comprising administering an effective amount of Formula I, as defined above.

A further aspect of the present invention provides a method for preventing hearing loss in a subject comprising administering to said subject an effective amount of the compound of Formula II;

FORMULA II

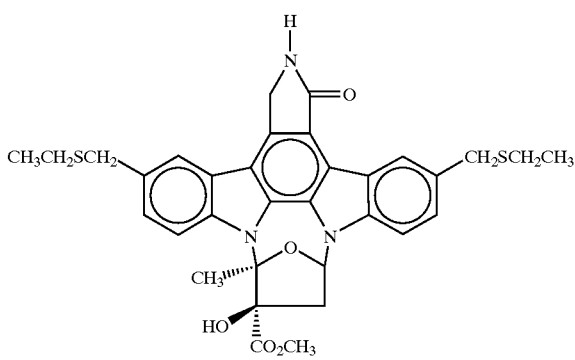

A further aspect of the present invention provides a method for preventing loss of sense of balance in a subject comprising administering to said subject an effective amount of the compound of Formula II as defined above.

A still further aspect of the present invention provides a method for preventing death of sensory hair cells in a subject comprising administering to said subject an effective amount of the compound of Formula II as defined above.

A further aspect of the present invention provides a method for preventing sudden sensorineural hearing loss in a subject due to death of sensory hair cells comprising administering to said subject an effective amount of the compound of Formula II as defined above.

A further aspect of the present invention provides a method for preserving function of sensory hair cells prior to or subsequent to trauma in a subject comprising administering to said subject an effective amount of the compound of Formula II as defined above.

A still further aspect of the present invention provides a method for preventing death of cochlear neurons in a subject comprising administering to said subject an effective amount of the compound of Formula II as defined above.

BRIEF DESCRIPTION OF THE DRAWINGS

FIGS. 2a and 2b depict treatment with the compound of Formula II. Treatment with the compound of Formula II preserved outer sensory hair cells throughout the organ of Corti. Cells were counted from one end of the organ in millimeters (X-axis) and the number of cells remaining after treatment are represented as a percentage of the total number originally present (sum of cells plus Deiters scars) on the Y-axis. FIG. 2a shows the number of OHCs in animals treated with the compound of Formula II, subject identification numbers (SIN) 13, 14, 19 and 20. FIG. 2b shows the number of OHCs present in control animals, SIN 15, 17 and 18. Three out of four compound of Formula II treated animals (SIN 13, 14 and 19) showed only a minor loss of sensory hair cells ranging from 1–3% (Table 2). The fourth animal (SIN 20) had a loss of 19%. In the three animals with almost complete sensory hair cell preservation, the small percentage of cells lost did not appear to localize to a particular site in the organ of Corti (FIG. 2a).

FIGS. 3a–f depict hair cell death in the guinea pig cochlea one day after noise exposure (120 dB, 4 kHz, 6 hr). The transverse (midmodiolar) paraffin section of the organ of Corti in the second cochlear turn is double stained with DAPI nuclear stain (FIG. 3a) and with TUNEL-method (FIG. 3b). The 3 outer hair cells (arrow) show distorted nuclei and are TUNEL-positive. Supporting cells, seen below the hair cells, are not TUNEL-labeled. FIG. 3c shows a TUNEL-labeled paraffin section and shows an outer hair cell nucleus with DNA fragmentation at high magnification. FIG. 3d depicts a toluidine blue-stained, resin-embedded semi-thin section of the organ of Corti in transverse plane and shows an inner hair cell (large arrow) and 3 rows of outer hair cells (OHCs, small arrows). Only OHC1 shows a fragmented nucleus (thick arrow). The section shown is from the area of scattered hair cell loss. (De=Deiter's cells.) FIG. 3e shows a toluidine blue-stained, resin-embedded semi-thin section in horizontal plane and at the level of hair cell nuclei. The section is from the region of maximal trauma. Most hair cells are lost, except one outer hair cell that shows a fragmented nucleus (thick arrow). FIG. 3f depicts a section, prepared as in FIG. 3e, from a nontraumatized region of the organ of Corti. Outer hair cells of the 3 rows are present and their nuclei are not fragmented. Scale bar represents 80 mm in FIGS. 3a and 3b, 10 mm in FIG. 3c, 18 mm in FIG. 3d, and 15 mm in FIGS. 3e and 3f.

FIG. 4a shows ABR threshold shifts 2 days after noise trauma. FIG. 4b shows ABR threshold shifts 6 days after noise trauma. FIG. 4c shows ABR shows ABR threshold shifts 14 days after noise trauma. Results show mean±SEM. Six and 14 days after exposure, the average threshold shifts of control animals are significantly greater than that of Formula II-treated animals. (*P<0.001; P<0.05; Student's t-test.)

FIGS. 5a and 5b depict the prevention of loss of sensory hair cells two weeks after traumatic noise exposure in animals treated with the compound of Formula II. Cochleograms of control (FIG. 5a, n=13) and Formula II-treated animals (FIG. 5b, n=12) revealed that a significantly lower percentage of sensory hair cells were lost in treated animals versus control animals. Results show mean±SEM.

Figure 7A:
FIGS. 7a–c depicts the prevention of hair cell loss in cochlear explants of neonatal rats exposed to neomycin for 48 hr. As shown in phalloidin-labeled confocal images.
Figure 7B:
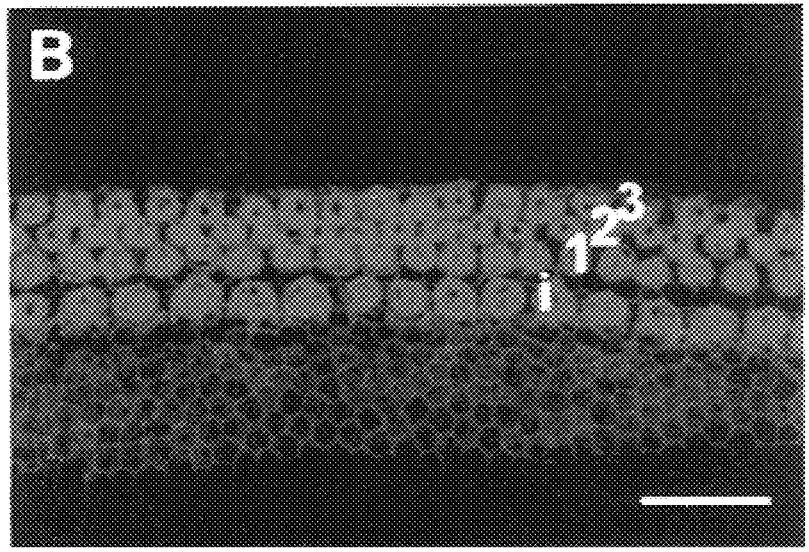

FIG. 7a shows the loss of hair cells caused by Neomycin. FIG. 7b shows the protective effect of Formula II in preventing hair cell loss in the basal turn of the cochlea. (i=inner hair cell; 1,2,3=rows of outer hair cells), and FIG. 7c shows the number of protected outer hair cells in basal and middle turns. Histograms and bars represent mean ± SEM for 3 experiments, each including 4 explants of both the control and Formula II-treated groups. The scale bar represents 50 mm in FIGS. 7a and 7b.

Figure 8:
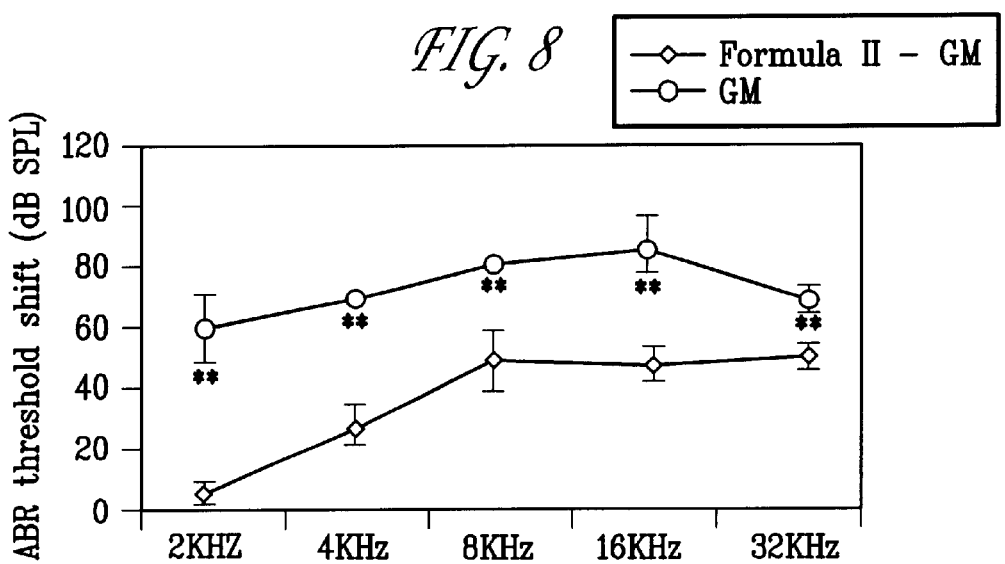

FIG. 8 shows the attenuation of gentamicin-induced hearing loss through administration of Formula II. Formula II treated cochleas showed statistically significantly less threshold shift at all frequencies tested than control cochleas.

Figure 9:
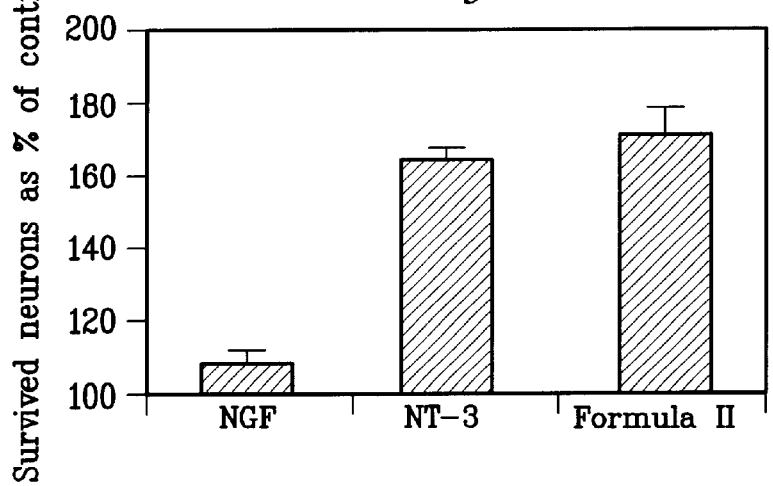

FIG. 9 shows the effects of Formula II (500 nM), neurotrophin-3 (2 ng/ml) and nerve growth factor (2 ng/ml) on the survival of neonatal cochlear neurons in vitro. Numbers of neurons in cultures with added compounds are expressed as percentage of the number of neurons in control cultures. Neurons were counted after 48 hr in culture. Values represent mean ± SEM from 3 separate experiments. Formula II was as efficacious as NT-3 in promoting survival of cochlear neurons. NGF served as a negative control.

Figure 10:
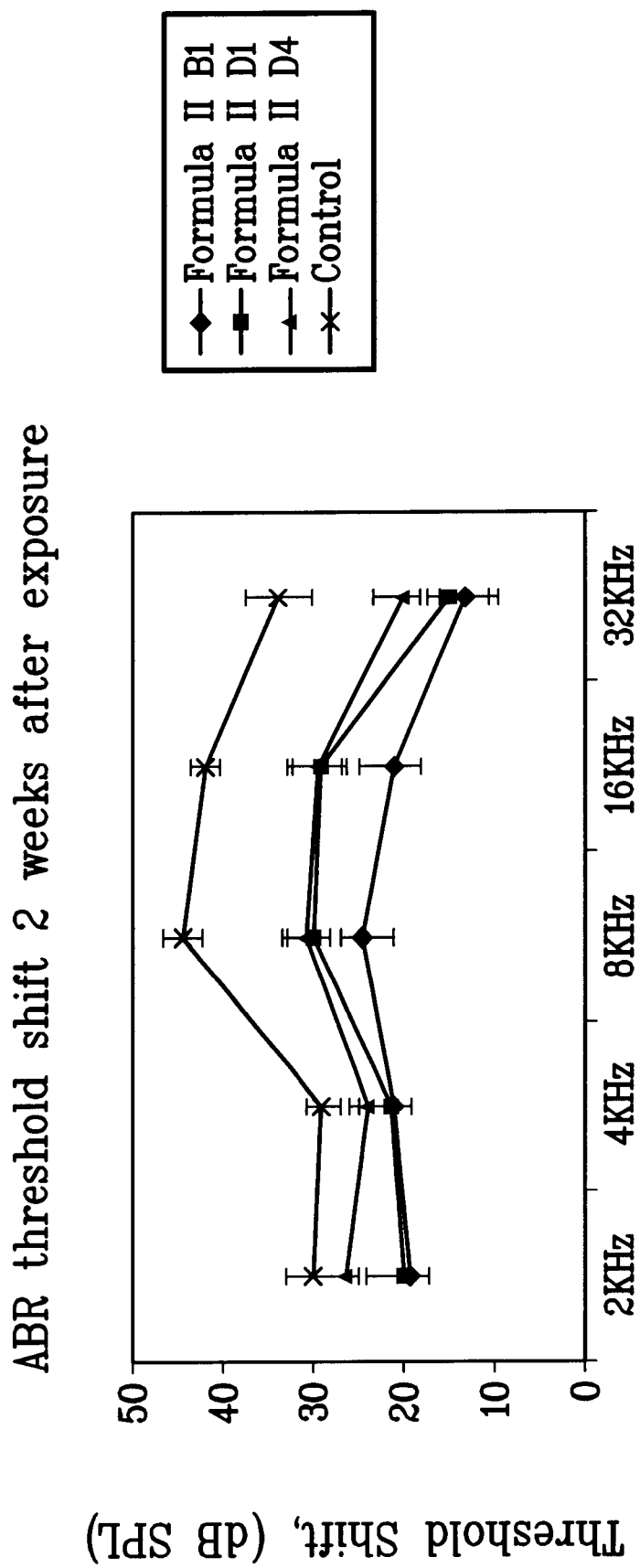
Figure 11A:
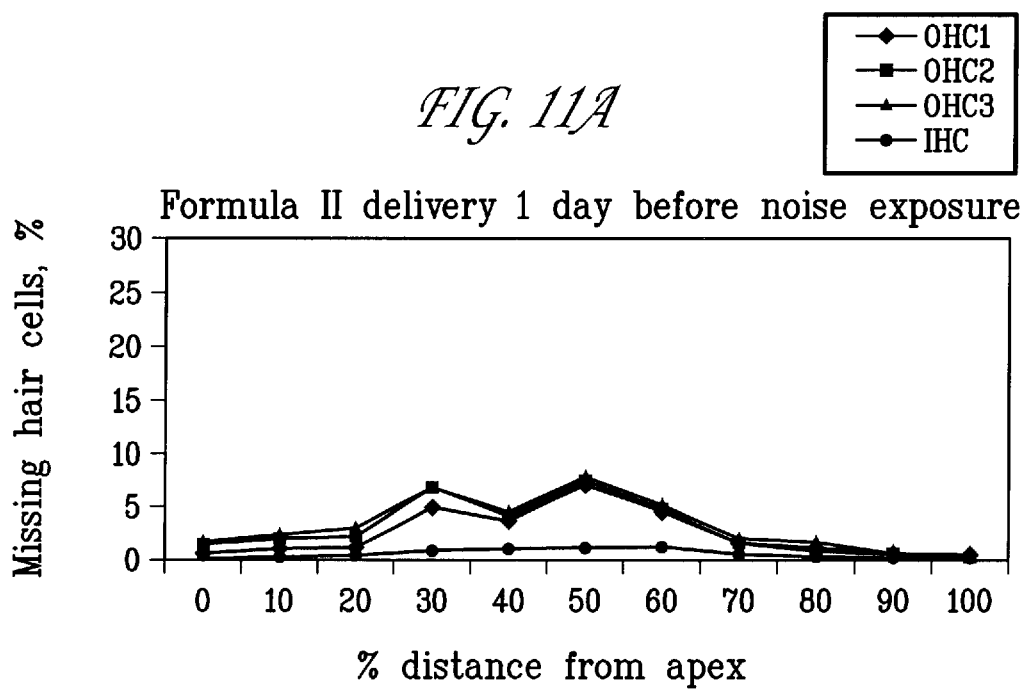
Figure 11B:
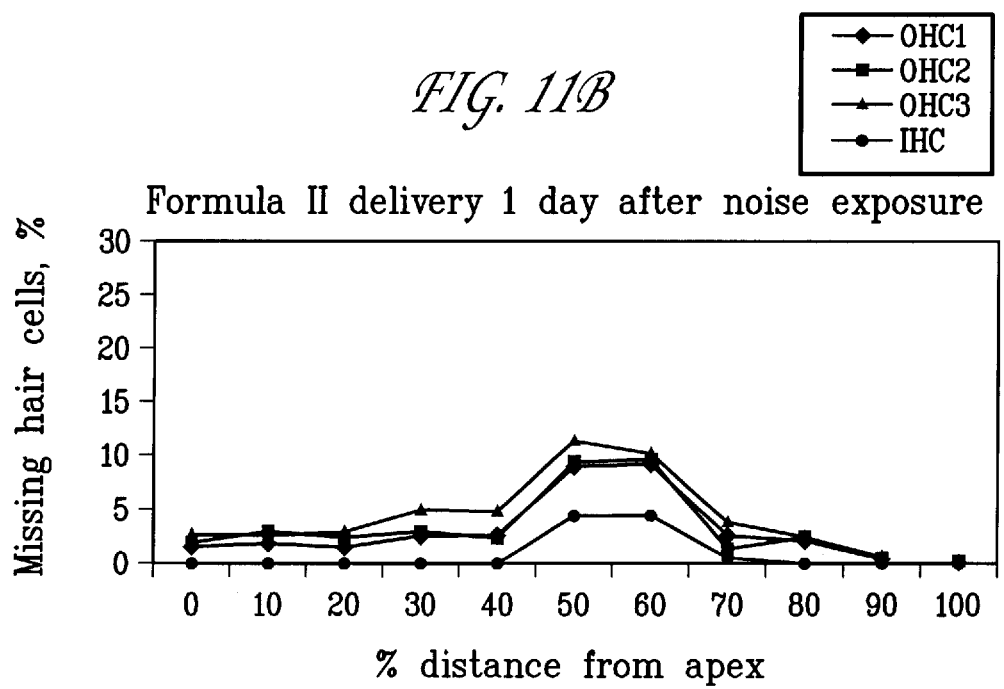
Figure 11C:
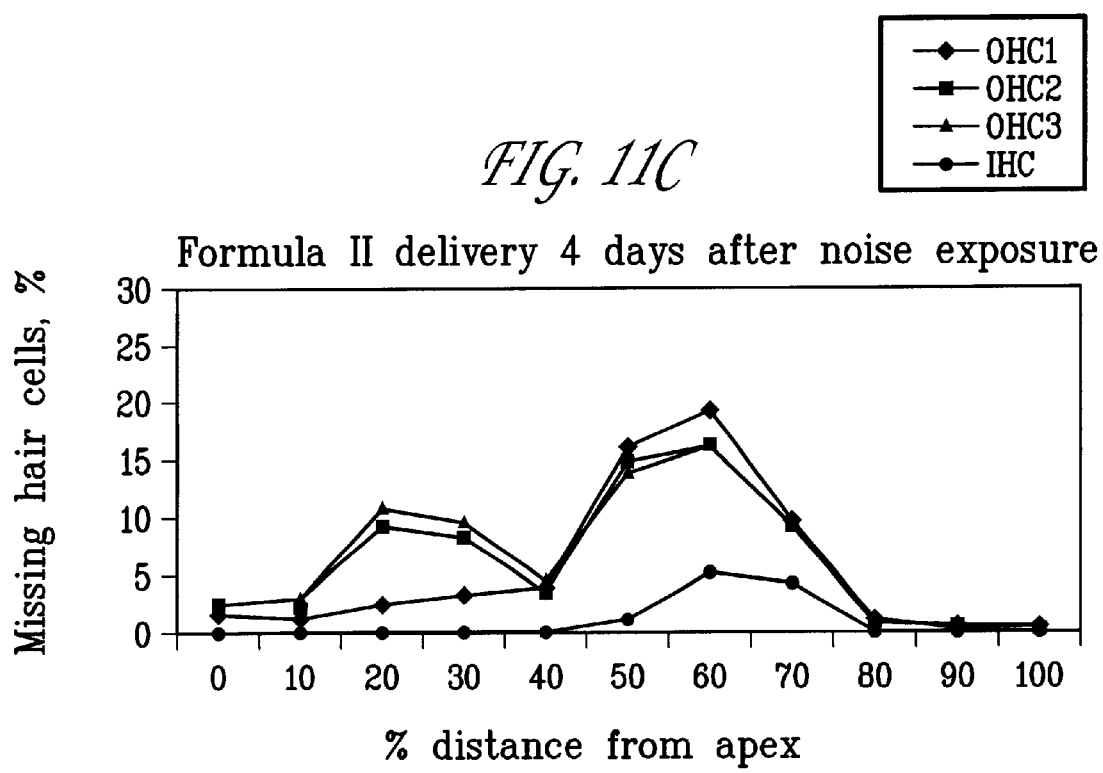
Figure 11D:
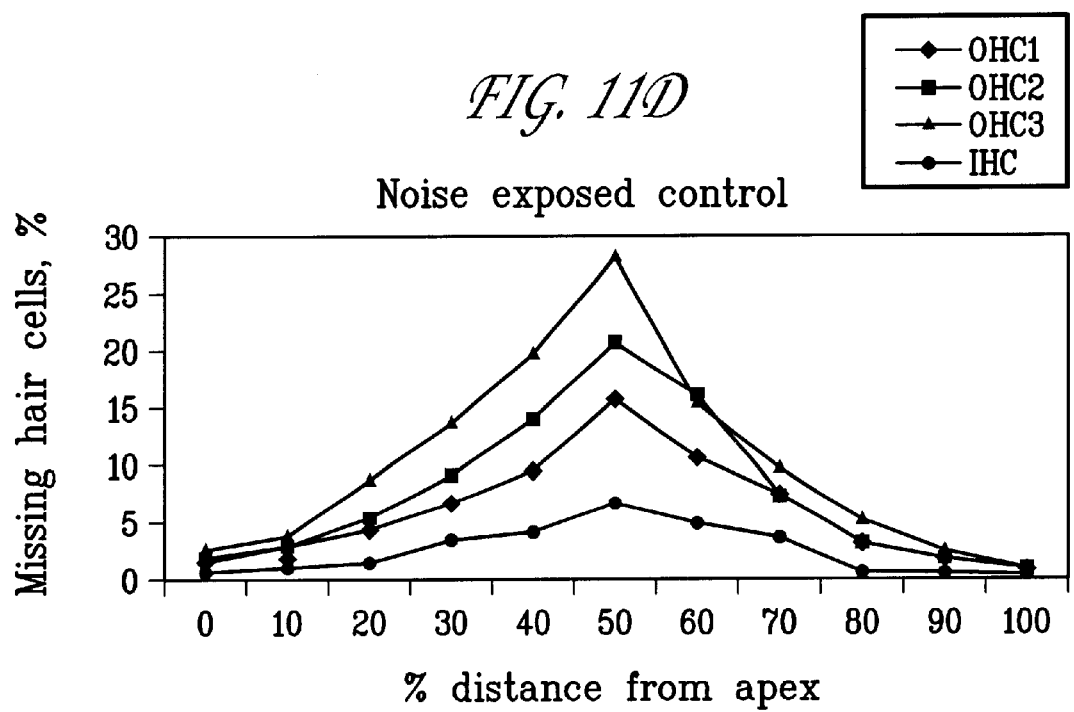

FIG. 10 depicts the effect of delayed dosing of Formula II following noise-induced hearing loss. Although attenuation of hearing loss is most effective following administration of Formula II prior to the noise lesion, administration of Formula II both 1 and 4 days subsequent to noise lesioning attenuates hearing loss compared to control.

FIGS. 11a–d depict the effect of delayed dosing of Formula II following noise-induced hearing loss. Cochleograms of Formula II-treated animals (FIGS. 11a–c, n=12) and control (FIG. 11d, n=13) revealed that a significantly lower percentage of sensory hair cells were lost in treated animals versus control animals.

Results show mean ± SEM.

Figure 12A:
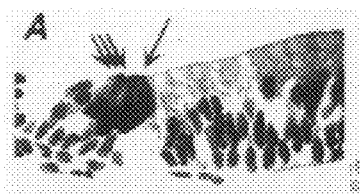
Figure 12B:
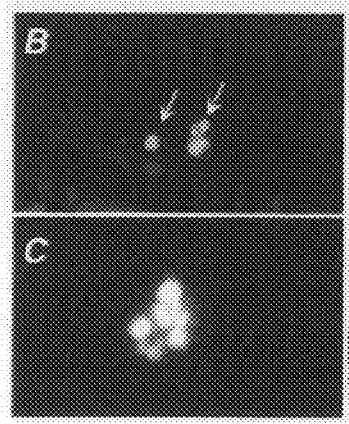
Figure 12C:
Figure 12D:
Figure 12E:
Figure 12F:

FIGS. 12a–f depict hair cell death, and JNK and c-Jun phosphorylation in neomycin-exposed (100 mM) cochlear explants of neonatal rats. The specimens were embedded in paraffin and cut in transverse (midmodiolar) plane. FIG. 12a shows one row of calbindin-immunoreactive inner hair cells and 3 rows of outer hair cells (arrows) are seen in nonexposed explants. FIG. 12b shows TUNEL-stained outer hair cell nuclei (arrows) are seen in cultures exposed to neomycin for 12 hr. FIG. 12c shows higher magnification of an outer hair cell nucleus showing TUNEL-positive DNA fragmentation. FIGS. 12d and 12e show that phospho-JNK and phospho-c-Jun immunolabeling, respectively, is found in the nuclei of hair cells (arrows) exposed to neomycin for 6 hr. FIG. 12f shows that phospho-c-Jun immunoreactive hair cells are not seen in cultures coincubated with neomycin and Formula II (500 nM) for 6 hr. Arrows point to hair cells. Scale bar represents 27 mm in FIGS. 12a, 12b, 12d, 12e, and 12f, 10 mm in FIG. 12c.

DETAILED DESCRIPTION OF THE INVENTION

As employed above and throughout our disclosure, the following terms, unless otherwise indicated, shall be understood to have the following meanings.

As used herein, the term "alkyl" means a straight-chain, cyclic, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, hexyl, octyl, cyclopropyl, and cyclopentyl. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons.

Alkyl groups and alkyl moieties contained within substituent groups such as aralkyl, alkoxy, arylalkoxy, hydroxyalkoxy, alkoxy-alkoxy, hydroxy-alkylthio, alkoxy-alkylthio, alkylcarbonyloxy, hydroxyalkyl and acyloxy groups may be substituted or unsubstituted. A substituted alkyl group has 1 to 3 independently-selected substituents, preferably hydroxy, lower alkoxy, lower alkoxy-alkoxy, substituted or unsubstituted arylalkoxy-lower alkoxy, substituted or unsubstituted heteroarylalkoxy-lower alkoxy, substituted or unsubstituted arylalkoxy, substituted or unsubstituted heterocycloalkoxy, halogen, carboxyl, lower alkoxycarbonyl, nitro, amino, mono- or di-lower alkylamino, dioxolane, dioxane, dithiolane, dithione, furan, lactone, or lactam.

As used herein, the term "alkenyl" is intended to include straight-chain, cyclic, or branched hydrocarbon chains having at least one carbon-carbon double bond. Examples of alkenyl groups include ethenyl, propenyl, 3-methylbutenyl, and cyclohexenyl groups. As used herein, the term "alkynyl" is intended to include straight-chain, cyclic, or branched hydrocarbon chains having at least one carbon-carbon triple bond. Examples of alkynyl groups include ethynyl, propynyl, 3-methylbutynyl, and cyclohexynyl groups.

As used herein, the "acyl" moiety of acyl-containing groups such as acyloxy groups is intended to include a straight-chain, branched, or cyclic alkanoyl group having 1 to 6 carbon atoms, such as formyl, acetyl, propanoyl, butyryl, valeryl, pivaloyl or hexanoyl.

As used herein, the term "carbocyclic" or "carbocyclyl" refers to cyclic groups in which the ring portion is composed solely of carbon atoms. These include, but are not limited to, cyclopropyl, cyclobutyl, cyclopentyl, cyclohexl, cycloheptyl, cyclooctyl. The term "carbocyclic aromatic ring" is intended to include carbocyclic rings which are also aryl rings. The terms "heterocyclo", "heterocyclic" and "heterocyclyl" refer to cyclic groups in which the ring portion includes at least one heteroatom such as O, N, or S. Heterocyclyl groups include heteroaryl and heteroalkyl groups.

As used herein the term "aryl" means an aromatic ring having 6 to 12 carbon atoms such as phenyl, biphenyl and naphthyl. Preferred aryl groups include unsubstituted or substituted phenyl and naphthyl groups. The term "heteroaryl" as used herein denotes an aryl group in which one or more ring carbon atoms is replaced by a hetero (i.e., non-carbon) atom such as O, N or S. Preferred heteroaryl groups include pyridyl, pyrimidyl, pyrrolyl, furyl, thienyl, imidazolyl, triazolyl, tetrazolyl, quinolyl, isoquinolyl, benzoimidazolyl, thiazolyl, pyrazolyl, and benzothiazolyl groups. The term "heteroalkyl" denotes a cycloalkyl group in which one or more ring carbon atoms is replaced by hetero atoms such as O, N, or S.

As used herein, the term "aralkyl" (or "arylalkyl") is intended to denote a group having from 7 to 15 carbons, consisting of an alkyl group that bears an aryl group. Examples of aralkyl groups include, but are not limited to, benzyl, phenethyl, benzhydryl and naphthylmethyl groups. Substituted aryl, substituted heterocyclic and substituted aralkyl groups each have 1 to 3 independently selected substituents that are preferably lower alkyl, hydroxy, lower alkoxy, carboxy, lower alkoxycarbonyl, nitro, amino, mono- or di-lower alkylamino, and halogen.

Preferred heterocyclic groups formed with a nitrogen atom include pyrrolidinyl, piperidinyl, piperidino, morpholinyl, morpholino, thiomorpholino, N-methylpiperazinyl, indolyl, isoindolyl, imidazole, imidazoline, oxazoline, oxazole, triazole, thiazoline, thiazole, isothiazole, thiadiazoles, triazines, isoxazole, oxindole, indoxyl, pyrazole, pyrazolone, pyrimidine, pyrazine, quinoline, iosquinoline, and tetrazole groups. Preferred heterocyclic groups formed with an oxygen atom include furan, tetrahydrofuran, pyran, benzofurans, isobenzofurans, and tetrahydropyran groups. Preferred heterocyclic groups formed with a sulfur atom include thiophene, thianaphthene, tetrahydrothiophene, tetrahydrothiapyran, and benzothiophenes.

As used herein, "hydroxyalkyl" groups are alkyl groups that have a hydroxyl group appended thereto. As used herein, "hydroxyalkoxy" groups are alkoxy groups that have a hydroxyl group appended thereto. As used herein, "halogen" refers to fluorine, chlorine, bromine and iodine.

As used herein, the term "heteroarylalkyl" means an arylalkyl group that contains a heteroatom in the aryl moiety. The term "oxy" denotes the presence of an oxygen atom. Thus, "alkoxy" groups are alkyl groups that are attached through an oxygen atom, and "carbonyloxy" groups are carbonyl groups that are attached through an oxygen atom.

As used herein, the terms "heterocycloalkyl" and "heterocycloalkoxy" mean an alkyl or an alkoxy group that has a heterocyclo group attached to the alkyl moiety thereof, and the term "arylalkoxy" means an alkoxy group that has an aryl group attached to the alkyl moiety thereof. As used herein, the term "alkylcarbonyloxy" means a group of formula —O—C(=O)—alkyl.

As used herein, the term "alkyloxy-alkoxy" denotes an alkoxy group that contains an alkyloxy substituent attached to its alkyl moiety. The term "alkoxy-alkylthio" means an alkylthio group (i.e., a group of formula —S—alkyl) that contains an alkoxy substituent attached to its alkyl moiety. The term "hydroxy-alkylthio" means an alkylthio group (i.e., a group of formula —S—alkyl) that contains a hydroxy substituent attached to its alkyl moiety.

As used herein, the term "monosaccharide" has its accustomed meaning as a simple sugar. As used herein, the term "amino acid" denotes a molecule containing both an amino group and a carboxyl group. Embodiments of amino acids include a-amino acids; i.e., carboxylic acids of general formula HOOC—CH(NH2)-(side chain). Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, *Biochemistry*, Second Edition, Worth Publishers, Inc, 1975, pages 73–75, incorporated by reference herein. In certain embodiments, substituent groups for the compounds described herein include the residue of an amino acid after removal of the hydroxyl moiety of the carboxyl group thereof; i.e., groups of Formula —C(=O)CH(NH$_2$)— (side chain).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The present invention is based upon the surprising discovery that compounds of Formula I are able to both prevent and treat damage to sensory hair cells. As shown herein, administration of the compound of Formula I prevents damage to sensory hair cells. Further, the compound of Formula I has been shown to effectively treat damage to sensory hair cells or cochlear neurons.

The present invention provides a method for preventing damage to sensory hair cells or cochlear neurons in a subject by administering an effective amount of the compound of Formula I. The present invention further provides a method for treating damage to sensory hair cells in a subject by administering a therapeutically effective amount of the compound of Formula I.

The present invention provides a method for preventing hearing loss in a subject comprising administering to said subject an effective amount of a fused pyrrolocarbazole of Formula I having the formula:

FORMULA I

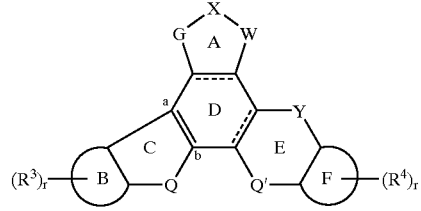

or a stereoisomer or pharmaceutically acceptable salt form thereof, wherein:

ring D is selected from phenyl and cyclohexene with double bond a–b;

ring B and ring F are independently selected from:
(a) a 6-membered carbocyclic ring in which from 1 to 3 carbon atoms may be replaced by heteroatoms;
(b) a 5-membered carbocyclic ring; and
(c) a 5-membered carbocyclic ring in which either:
(1) one carbon atom is replaced with an oxygen, nitrogen, or sulfur atom;
(2) two carbon atoms are replaced with a sulfur and a nitrogen atom, an oxygen and a nitrogen atom, or two nitrogen atoms; or
(3) three carbon atoms are replaced with three nitrogen atoms, one oxygen and two nitrogen atoms, or one sulfur and two nitrogen atoms;

G-X-W is selected from:
(a) $(Z^1Z^2)C$—$N(R^1)$—$C(Z^1Z^2)$;
(b) $CH(R^1)$—$C(=O)$—$N(R^1)$; and
(c) $N(R^1)$—$C(=O)$—$CH(R^1)$;

$Z^1$ and $Z^2$, at each occurrence, are independently selected from H, H; H, OR; H, SR; H, N(R)$_2$; and a group wherein $Z^1$ and $Z^2$ together form a moiety selected from =O, =S, and =NR; with the proviso that at least one of the pairs $Z^1$ and $Z^2$ forms =O;

R is independently selected from H, optionally substituted alkyl, OH, alkoxy, $OC(=O)R^{1a}$, $OC(=O)NR^{1c}R^{1d}$,$O(CH_2)_pNR^{1c}R^{1d}$, $O(CH_2)_pOR^{1b}$, optionally substituted arylalkyl and optionally substituted heteroarylalkyl;

$R^1$ is independently selected from:
(a) H, optionally substituted alkyl, optionally substituted aryl, optionally substituted arylalkyl, optionally substituted heteroaryl and optionally substituted heteroarylalkyl;
(b) $C(=O)R^{1a}$;
(c) $OR^{1b}$;
(d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$;

$R^{1a}$ is independently selected from optionally substituted alkyl, optionally substituted aryl and optionally substituted heteroaryl;

$R^{1b}$ is independently selected from H and optionally substituted alkyl;

$R^{1c}$ and $R_{1d}$ are each independently selected from H, optionally substituted alkyl and a linking group of the formula $(CH_2)_2$—$X^1$—$(CH_2)_2$;

$X^1$ is independently selected from O, S and $CH_2$;

Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^{2}$;

$R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;

$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;

$R^{2b}$ is selected from H and optionally substituted alkyl;

$R^{2c}$ and $R^{2d}$ are each independently selected from H and optionally substituted alkyl, or together form a linking group of the formula $(CH_2)_2$—$X^1$—$(CH_2)_2$;

$R^3$ and $R^4$ are each independently selected from:
(a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
(b) $CH_2OR^{14}$;
(c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
(d) $S(O)_yR^9$, $(CH_2)_pS(O)_yR^9$ and $CH_2S(O)_yR^{14}$;
(e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2$—$X^1$—$(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
(a) a direct bond;
(b) optionally substituted $CH_2$, $CH_2CH_2$ or $CH_2CH_2CH_2$, wherein said optional substituents are one to about three $R^{19}$ groups; and
(c) CH=CH, CH(OH)—CH(OH), O, S, $S(=O)$, $S(=O)_2$, $C(R^{18})_2$, $C=C(R^{19})_2$, $C(=O)$, $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2$—$X^1$—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
(a) a direct bond;
(b) $NR^6$;
(c) optionally substituted $CH_2$, $CH_2CH_2$ or $CH_2CH_2CH_2$;
(d) $CR^{22}R^{24}$; and
(e) CH=CH, CH(OH)CH(OH), O, S, $S(=O)$, $S(=O)_2$, $C(=O)$, $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, $Z'$—$CH_2$ and $CH_2Z'CH_2$;

$Z'$ is selected from $C(R^{11})(OR^{12})$, O, S, $C(=O)$, $C(=NOR^{11})$ and $NR^{11}$;

$R^6$ is selected from H, $SO_2R^{2a}$, $CO_2R^{2a}$, $C(=O)R^{2a}$, $C(=O)NR^{1c}$, $R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

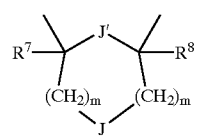

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2-X^3-CH_2$;

$X^3$ is a bond, O, S, or $NR^{10}$;

J is selected from a bond, O, CH=CH, S, C(=O), $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl—OH, alkoxy and $CO_2R^{10}$;

$R^{17}$ is selected from H, alkyl, aryl and heteroaryl;

$R^{22}$ is

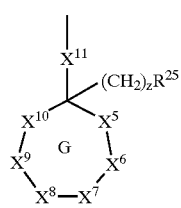

$X^5$ and $X^6$ are independently selected from O, N, S, $CHR^{26}$, $C(OH)R^{26}$, C(=O) and $CH_2=C$;

$X^7$ and $X^8$ are independently selected from a bond, O, N, S, $CHR^{26}$, $C(OH)R^{26}$, C(=O) and $CH_2=C$;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein
  (1) ring G contains 0 to about 3 ring heteroatoms;
  (2) any two adjacent hydroxyl groups of ring G can be joined to form a dioxolane ring;
  (3) any two adjacent ring carbon atoms of ring G can be joined to form a fused aryl or heteroaryl ring; with the provisos that:
    (a) when $X^{11}$ is a bond, ring G can be heteroaryl; and
    (b) ring G:
      (i) contains at least one carbon atom that is saturated;
      (ii) does not contain two adjacent ring 0 atoms;
      (iii) contains a maximum of two C(=O) groups;

$R^{27}$ is selected from H and alkyl;

$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;

$R^{29}$ is selected from alkyl, aryl and heteroaryl;

$R^{30}$ is selected from H, alkyl, acyl and $C(=O)NR^{11}R^{12}$;

m is independently selected from 0, 1, and 2;

p is independently selected from 1, 2, 3, and 4;

r is independently selected from 0, 1, and 2;

y is independently selected from 0, 1 and 2; and z is selected from 0, 1, 2, 3 and 4;

with the provisos that at least one of Y and Q' is a direct bond, when Y is a direct bond, Q' is other than a direct bond, when Q' is a direct bond, Y is other than a direct bond, and when rings B and F are phenyl, G-X-W is $CH_2NHC(=O)$, Y is a direct bond, Q is $NR^2$ and Q' is $NR^6$ where $R^6$ is joined with $R^2$ to form

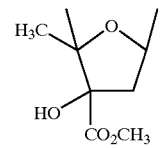

then $R^3$ is other than $CH_2SCH_2CH_3$ (in other words, the latter proviso is directed to the compound of Formula II).

In one preferred embodiment, Y is a direct bond and Q is $NR_2$. In a more preferred embodiment, ring B and ring F of the fused pyrrolocarbazole are phenyl, G-X-W is selected from $CH_2NR^1C(=O)$, $C(=O)NR^1CH_2$, and $C(=O)NR^1C(=O)$, and Q' is $NR^6$. In an even more preferred embodiment, the fused pyrrolocarbazole has the formula:

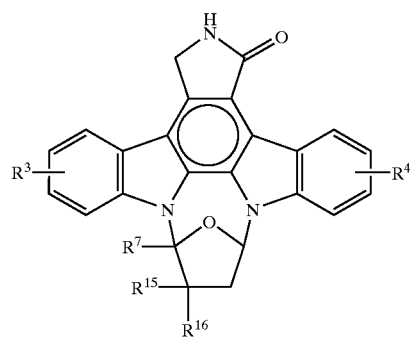

In an even more preferred embodiment, $R^3$ and $R^4$ of the fused pyrrolocarbazole are selected from H, alkyl, Cl, Br, $CH_2OH$, $CH_2SOCH_2CH_3$, $CH_2SO_2CH_2CH_3$, $NHCONHC_6H_5$, $CH_2SCH_2CH_3$, $CH_2S$-phenyl, $CH_2S$-pyridyl, $CH\ NHCO_2CH_3$, $CH_2OC(=O)NHCH_2CH_3$, $N(CH_3)_2$, CH=NNH, $CH_2N(CH_3)_2$, and $CH_2OCH_2CH_3$; $R^7$ is selected from H and alkyl; and $R^{15}$ and $R^{16}$ are independently selected from H, alkyl, OH, $CH_2OH$, alkoxy, and $CO_2$alkyl. In an even more preferred embodiment, the fused pyrrolocarbazole has the formula:

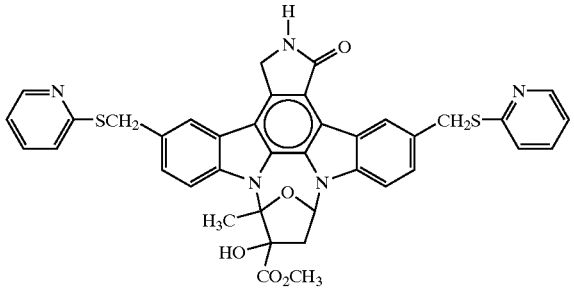

In another preferred embodiment, Q' is $CH_2$, $CH_2CH_2$, S or $CH(CH(CH_3)(OH))$. In a more preferred embodiment, ring B and ring F of the fused pyrrolocarbazole are phenyl and G-X-W is selected from $CH_2NR^1C(=O)$, $C(=O)$ NR¹CH₂. In an even more preferred embodiment, the fused pyrrolocarbazole has the formula

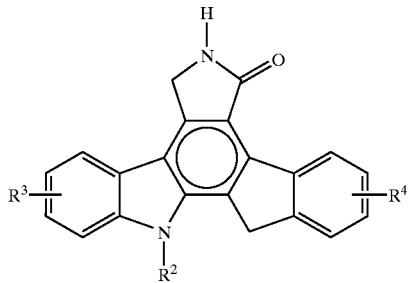

In a more preferred embodiment, $R^2$ is H, $CH_2CH_2OH$, $CH_2CH_2NHC(=O)$—$C_6H_5$—OH, $CH_2CH_2CH_2OH$, $R^3$ and $R^4$ of the fused pyrrolocarbazole are selected from H, alkyl, Cl, Br, alkoxy, $CH_2OH$, $CH_2SOCH_2CH_3$, $CH_2SO_2CH_2CH_3$, $NHCONHC_6H_5$, $CH_2SCH_2CH_3$, $CH_2S$-phenyl, $CH_2S$-pyridyl, $CHNHCO_2CH_3$, $CH_2OC(=O)NHCH_2CH_3$, $N(CH_3)_2$, CH=NNH, $CH_2N(CH_3)_2$, and $CH_2OCH_2CH_3$; $R^7$ is selected from H and alkyl; and $R^{15}$ and $R^{16}$ are independently selected from H, alkyl, OH, $CH_2OH$, alkoxy, and $CO_2$alkyl. In a more preffered embodiment, the fused pyrrolocarbazole has the formula:

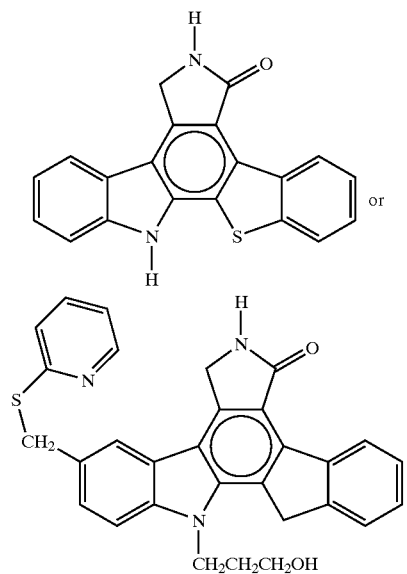

In another preferred embodiment, the fused pyrrolocarbazole has the formula:

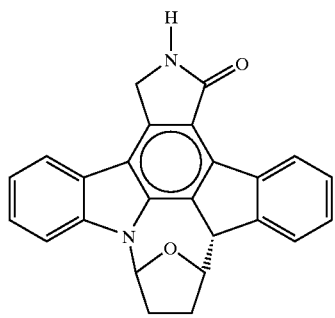

As used herein, the term "preventing", in the context of preventing hearing loss, loss of sense of balance, death of sensory hair cells or cochlear neurons, sensorineural hearing loss, or damage to sensory hair cells or cochlear neurons and the like, refers to reducing, minimizing, or completely eliminating such loss or damage. As used herein, "preventing" may include, for example, at least about a 15% reduction of loss or damage, more preferably at least about 25%, more preferably at least about 50%, even more preferably at least about 75%, even more preferably at least about 80%, even more preferably at least about 85%, even more preferably at least about 90%, even more preferably at least about 95%, and most preferably about 100%. As used herein, the term "sensory hair cells" refers to the hair cells present in vertebrates, including the auditory sensory hair cells present in the Organ of Corti, and the vestibular sensory hair cells present in the semicircular canals and maculae of the inner ear.

As used herein, the term "subject" refers to mammals including but not limited to humans and primates; avians; domestic household, sport or farm animals including dogs, cats, sheep, goats, cows, horses and pigs; lab animals including rats, mice, rabbits and guinea pigs; fish; reptiles; zoo and wild animals.

As used herein, the term "hearing loss" refers to an inability to perceive auditory stimuli that are perceivable by a normally functioning subject.

As used herein, the term "loss of sense of balance" refers to a deficit in the vestibular system of an animal compared to the vestibular system of a normally functioning subject.

As used herein, the term "death of sensory hair cells" refers to a cessation of the ability of one or more sensory hair cells in perceiving and/or transducing sensory stimuli.

The term "administration" includes but is not limited to, oral, subbuccal, transdermal, parenteral, subcutaneous and topical. A common requirement for these routes of administration is efficient and easy delivery of the compound of Formula I to the target.

One mode of administration contemplated by the present invention is topical. The compound of Formula I may be administered topically in a number of ways, including, as a cream, a lotion, an ointment, as aerosol sprays, or as drops, including but not limited to eardrops and nosedrops.

Another mode of administration of the compound of Formula I to the subject is subbuccal through the use of tablets.

Yet another mode of administration of the compound of Formula I is subcutaneous administration.

Another mode of administration of the compound of Formula I is oral. The compound of Formula I may be administered orally to a subject in a number of ways, including, but not limited to tablets, capsules and caplets.

A preferred mode of topical administration is through the use of eardrops. The formulation and administration of eardrops is well within the skill of the art. In a preferred embodiment, eardrops may be composed of from 0.1% to 20% by weight of the compound of Formula I in a suitable carrier. Two to four drops may be administered to a patient every four to eight hours.

A more preferred mode of administration is the direct administration of the compound of Formula I in situ to the Round window via a catheter. Such administration may permit the use of lower dosages (Korver et al., 21$^{st}$ Midwinter Research Meeting of ARO, St. Petersburg Beach, Fla., Feb. 15–19, 1998, Abstract No. 536, page 135).

The nature of the pharmaceutical composition for the administration is dependent on the mode of administration and can readily be determined by one of ordinary skill in the art. For example, for oral administration, pharmaceutical compositions may contain, in addition to the compound of Formula I, pharmaceutically acceptable carriers, vehicles, buffers and excipients.

As used herein, the term "effective amount," refers to the amount of the compounds of Formula I and Formula II required to achieve an intended purpose for both prophylaxis or treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: *Remington's Pharmaceutical Sciences,* 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3 In: *Goodman & Gilman's The Pharmacological Basis of Therapeutics,* 9th Ed., Hardman et al., eds., McGraw-Hill, New York, N.Y., 1996).

According to the present invention, the compound of Formula I is administered to subjects at a dose ranging from about 0.1 µg/kg/day to about 100 mg/kg/day, preferably at a dose from about 1 µg/kg/day to about 25 mg/kg/day, and more preferably at a dose of about 5 mg/kg/day. Generally, lower dosages of the compound of Formula I will be initially administered to a patient. Dosages may be incrementally increased until the desired level is achieved. It is contemplated that the compound of Formula I can be administered topically onto the eardrum using eardrops. Also, the compound of Formula I can be administered directly to the Round window using a catheter (Leary, New York Times, Health, Sep. 1, 1998).

The present invention also provides methods for preventing loss of sense of balance in a subject comprising administering to said subject an effective amount of a fused pyrrolocarbazole of Formula I having the formula:

FORMULA I

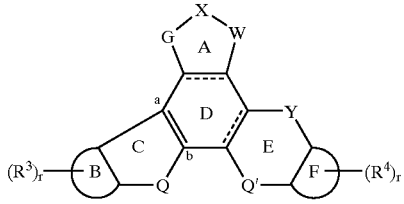

or a stereoisomer or pharmaceutically acceptable salt form thereof, wherein:
  ring D is selected from phenyl and cyclohexene with double bond a-b;
  ring B and ring F are independently selected from:
    (a) a 6-membered carbocyclic ring in which from 1 to 3 carbon atoms may be replaced by heteroatoms;
    (b) a 5-membered carbocyclic ring; and
    (c) a 5-membered carbocyclic ring in which either:
      (1) one carbon atom is replaced with an oxygen, nitrogen, or sulfur atom;
      (2) two carbon atoms are replaced with a sulfur and a nitrogen atom, an oxygen and a nitrogen atom, or two nitrogen atoms; or
      (3) three carbon atoms are replaced with three nitrogen atoms, one oxygen and two nitrogen atoms, or one sulfur and two nitrogen atoms;

G-X-W is selected from:
  (a) $(Z^1Z^2)C-N(R^1)-C(Z^1Z^2)$;
  (b) $CH(R^1)-C(=O)-N(R^1)$; and
  (c) $N(R^1)-C(=O)-CH(R^1)$;
$Z^1$ and $Z^2$, at each occurrence, are independently selected from H, H; H, OR; H, SR; H, $N(R)_2$; and a group wherein $Z^1$ and $Z^2$ together form a moiety selected from $=O$, $=S$, and $=NR$; with the proviso that at least one of the pairs $Z^1$ and $Z^2$ forms $=O$;
R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR^{1b}$, optionally substituted arylalkyl and optionally substituted heteroarylalkyl;
$R^1$ is independently selected from:
  (a) H, optionally substituted alkyl, optionally substituted aryl, optionally substituted arylalkyl, optionally substituted heteroaryl and optionally substituted heteroarylalkyl;
  (b) $C(=O)R^{1a}$;
  (c) $OR^{1b}$;
  (d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$;
$R^{1a}$ is independently selected from optionally substituted alkyl, optionally substituted aryl and optionally substituted heteroaryl;
$R^{1b}$ is independently selected from H and optionally substituted alkyl;
$R^{1c}$ and $R^{1d}$ are each independently selected from H, optionally substituted alkyl and a linking group of the formula $(CH_2)_2-X^1-(CH_2)_2$;
$X^1$ is independently selected from O, S and $CH_2$;
Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;
$R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;
$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;
$R^{2b}$ is selected from H and optionally substituted alkyl;
$R^{2c}$ and $R^{2d}$ are each independently selected from H and optionally substituted alkyl, or together form a linking group of the formula $(CH_2)_2-X^1-(CH_2)_2$;
$R^3$ and $R^4$ are each independently selected from:
  (a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
  (b) $CH_2OR^{14}$;
  (c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
  (d) $S(O)_yR^9$, $(CH_2)_pS(O)_yR^9$ and $CH_2S(O)_yR^{14}$;
  (e) optionally substituted alkyl, optionally substituted alkenyl and optionally substituted alkynyl, wherein said optional substituents are one to about three $R^5$ groups;
$R^9$ is selected from alkyl, $(CH_2)_r$aryl and $(CH_2)_r$heteroaryl;

$R^{10}$ is selected from H, alkyl, $(CH_2)_p$aryl and $(CH_2)_p$heteroaryl;

$R^{11}$ and $R^{12}$ are independently selected from H and optionally substituted alkyl, or together form a linking group of the formula $(CH_2)_2$—$X^1$—$(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
(a) a direct bond;
(b) optionally substituted $CH_2$, $CH_2CH_2$ or $CH_2CH_2CH_2$, wherein said optional substituents are one to about three $R^{19}$ groups; and
(c) CH=CH, CH(OH)—CH(OH), O, S, S(=O), $S(=O)_2$, $C(R^{18})_2$, $C=C(R^{19})_2$, C(=O), $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2$—$X^1$—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is selected from H and alkyl;

Q' is selected from:
(a) a direct bond;
(b) $NR^6$;
(c) optionally substituted $CH_2$, $CH_2CH_2$ or $CH_2CH_2CH_2$;
(d) $CR^{22}R^{24}$; and
(e) CH=CH, CH(OH)CH(OH), O, S, S(=O), $S(=O)_2$, C(=O), $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, $Z'$—$CH_2$ and $CH_2Z'CH_2$;

Z' is selected from $C(R^{11})(OR^{12})$, O, S, C(=O), $C(=NOR^{11})$ and $NR^{11}$;

$R^6$ is selected from H, $SO_2R^{2a}$, $CO_2R^{2a}$, $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

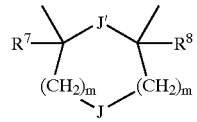

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2$—$X^3$—$CH_2$;

$X^3$ is a bond, O, S, or $NR^{10}$;

J is selected from a bond, O, CH=CH, S, C(=O), $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

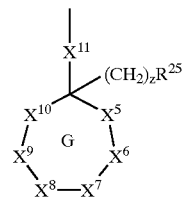

$X^5$ and $X^6$ are independently selected from O, N, S, $CHR^{26}$, $C(OH)R^{26}$, C(=O) and $CH_2$=C;

$X^7$ and $X^8$ are independently selected from a bond, O, N, S, $CHR^{26}$, $C(OH)R^{26}$, C(=O) and $CH_2$=C;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein
(1) ring G contains 0 to about 3 ring heteroatoms;
(2) any two adjacent hydroxyl groups of ring G can be joined to form a dioxolane ring;

(3) any two adjacent ring carbon atoms of ring G can be joined to form a fused aryl or heteroaryl ring; with the provisos that:
(a) when $X^{11}$ is a bond, ring G can be heteroaryl; and
(b) ring G:
(i) contains at least one carbon atom that is saturated;
(ii) does not contain two adjacent ring O atoms;
(iii) contains a maximum of two C(=O) groups;
$R^{27}$ is selected from H and alkyl;
$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;
$R^{29}$ is selected from alkyl, aryl and heteroaryl;
$R^{30}$ is selected from H, alkyl, acyl and $C(=O)NR^{11}R^{12}$;
m is independently selected from 0, 1, and 2;
p is independently selected from 1, 2, 3, and 4;
r is independently selected from 0, 1, and 2;
y is independently selected from 0, 1 and 2; and
z is selected from 0, 1, 2, 3 and 4;
with the provisos that at least one of Y and Q' is a direct bond, when Y is a direct bond, Q' is other than a direct bond, when Q' is a direct bond, Y is other than a direct bond, and when rings B and F are phenyl, G-X-W is $CH_2NHC(=O)$, Y is a direct bond, Q is $NR^2$ and Q' is $NR^6$ where $R^6$ is joined with $R^2$ to form

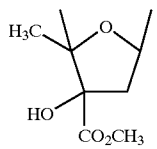

then $R^3$ is other than $CH_2SCH_2CH_3$.

The present invention also provides methods for preventing death of sensory hair cells in a subject, said method comprising administering to said subject an effective amount of a fused pyrrolocarbazole of Formula I having the formula:

FORMULA I

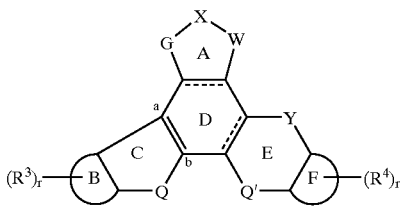

or a stereoisomer or pharmaceutically acceptable salt form thereof, wherein:
ring D is selected from phenyl and cyclohexene with double bond a-b;
ring B and ring F are independently selected from:
(a) a 6-membered carbocyclic ring in which from 1 to 3 carbon atoms may be replaced by heteroatoms;
(b) a 5-membered carbocyclic ring; and
(c) a 5-membered carbocyclic ring in which either:
(1) one carbon atom is replaced with an oxygen, nitrogen, or sulfur atom;
(2) two carbon atoms are replaced with a sulfur and a nitrogen atom, an oxygen and a nitrogen atom, or two nitrogen atoms; or
(3) three carbon atoms are replaced with three nitrogen atoms, one oxygen and two nitrogen atoms, or one sulfur and two nitrogen atoms;

G-X-W is selected from:
(a) $(Z^1Z^2)C$—$N(R^1)$—$C(Z^1Z^2)$;
(b) $CH(R^1)$—$C(=O)$—$N(R^1)$; and
(c) $N(R^1)$—$C(=O)$—$CH(R^1)$;
$Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;
R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR^{1b}$, optionally substituted arylalkyl and optionally substituted heteroarylalkyl;
$R^1$ is independently selected from:
(a) H, optionally substituted alkyl, optionally substituted aryl, optionally substituted arylalkyl, optionally substituted heteroaryl and optionally substituted heteroarylalkyl;
(b) $C(=O)R^{1a}$;
(c) $OR^{1b}$;
(d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$;
$R^{1a}$ is independently selected from optionally substituted alkyl, optionally substituted aryl and optionally substituted heteroaryl;
$R^{1b}$ is independently selected from H and optionally substituted alkyl;
$R^{1c}$ and $R^{1d}$ are each independently selected from H, optionally substituted alkyl and a linking group of the formula $(CH_2)_2$—$X^1$—$(CH_2)_2$;
$X^1$ is independently selected from O, S and $CH_2$;
Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;
$R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;
$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;
$R^{2b}$ is selected from H and optionally substituted alkyl;
$R^{2c}$ and $R^{2d}$ are each independently selected from H and optionally substituted alkyl, or together form a linking group of the formula $(CH_2)_2$—$X^1$—$(CH_2)_2$;
$R^3$ and $R^4$ are each independently selected from:
(a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
(b) $CH_2OR^{14}$;
(c) $NR^{10}C(=O)NR^{11}R^{12}$, $CO_2R^{10}$, $C(=O)R^9$, $C(=O)NR^{11}R^{12}$, CH=$NOR^{10}$, CH=$NR^{10}$, $(CH_2)_pNR^{11}R^{12}$, $(CH_2)_pNHR^{14}$ and CH=$NNR^{11}R^{12}$;
(d) $S(O)_yR^9$, $(CH_2)_pS(O)_yR^9$ and $CH_2S(O)_yR^{14}$;
(e) optionally substituted alkyl, optionally substituted alkenyl and optionally substituted alkynyl, wherein said optional substituents are one to about three $R^5$ groups;
$R^9$ is selected from alkyl, $(CH_2)_r$aryl and $(CH_2)_r$heteroaryl;

$R^{10}$ is selected from H, alkyl, $(CH_2)_p$aryl and $(CH_2)_p$heteroaryl;

$R^{11}$ and $R^{12}$ are independently selected from H and optionally substituted alkyl, or together form a linking group of the formula $(CH_2)_2$—$X^1$—$(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
(a) a direct bond;
(b) optionally substituted $CH_2$, $CH_2CH_2$ or $CH_2CH_2CH_2$, wherein said optional substituents are one to about three $R^{19}$ groups; and
(c) CH=CH, CH(OH)—CH(OH), O, S, S(=O), $S(=O)_2$, $C(R^{18})_2$, $C=C(R^{19})_2$, $C(=O)$, $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$ $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2$—$X^1$—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, OC(=S)$NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is selected from H and alkyl;

Q' is selected from:
(a) a direct bond;
(b) $NR^6$;
(c) optionally substituted $CH_2$, $CH_2CH_2$ or $CH_2CH_2CH_2$;
(d) $CR^{22}R^{24}$; and
(e) CH=CH, CH(OH)CH(OH), O, S, S(=O), $S(=O)_2$, C(=O), $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, Z'—$CH_2$ and $CH_2Z'CH_2$;

Z' is selected from $C(R^{11})(OR^{12})$, O, S, C(=O), $C(=NOR^{11})$ and $NR^{11}$;

$R^6$ is selected from H, $SO_2R^{2a}$, $CO_2R^{2a}$, $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

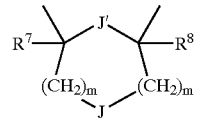

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2$—$X^3$—$CH_2$;

$X^3$ is a bond, O, S, or $NR^{10}$;

J is selected from a bond, O, CH=CH, S, C(=O), $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

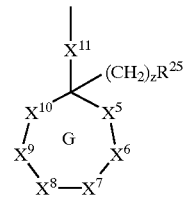

$X^5$ and $X^6$ are independently selected from O, N, S, $CHR^{26}$, $C(OH)R^{26}$, C(=O) and $CH_2=C$;

$X^7$ and $X^8$ are independently selected from a bond, O, N, S, $CHR^{26}$, $C(OH)R^{26}$, C(=O) and $CH_2=C$;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein
(1) ring G contains 0 to about 3 ring heteroatoms;
(2) any two adjacent hydroxyl groups of ring G can be joined to form a dioxolane ring;

(3) any two adjacent ring carbon atoms of ring G can be joined to form a fused aryl or heteroaryl ring; with the provisos that:
(a) when $X^{11}$ is a bond, ring G can be heteroaryl; and
(b) ring G:
(i) contains at least one carbon atom that is saturated;
(ii) does not contain two adjacent ring O atoms;
(iii) contains a maximum of two C(=O) groups;
$R^{27}$ is selected from H and alkyl;
$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;
$R^{29}$ is selected from alkyl, aryl and heteroaryl;
$R^{30}$ is selected from H, alkyl, acyl and $C(=O)NR^{11}R^{12}$;
m is independently selected from 0, 1, and 2;
p is independently selected from 1, 2, 3, and 4;
r is independently selected from 0, 1, and 2;
y is independently selected from 0, 1 and 2; and
z is selected from 0, 1, 2, 3 and 4;
with the provisos that at least one of Y and Q' is a direct bond, when Y is a direct bond, Q' is other than a direct bond, when Q' is a direct bond, Y is other than a direct bond, and when rings B and F are phenyl, G-X-W is $CH_2NHC(=O)$, Y is a direct bond, Q is $NR^2$ and Q' is $NR^6$ where $R^6$ is joined with $R^2$ to form

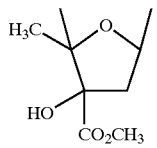

then $R^3$ is other than $CH_2SCH_2CH_3$.

The present invention also provides methods for preventing sudden sensorineural hearing loss in a subject due to death of sensory hair cells comprising administering to said subject an effective amount of a fused pyrrolocarbazole of Formula I having the formula:

FORMULA I

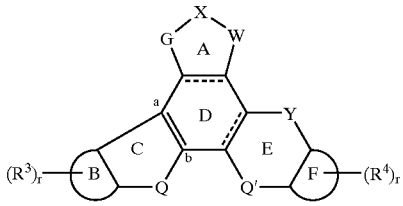

or a stereoisomer or pharmaceutically acceptable salt form thereof, wherein:
ring D is selected from phenyl and cyclohexene with double bond a-b;
ring B and ring F are independently selected from:
(a) a 6-membered carbocyclic ring in which from 1 to 3 carbon atoms may be replaced by heteroatoms;
(b) a 5-membered carbocyclic ring; and
(c) a 5-membered carbocyclic ring in which either:
(1) one carbon atom is replaced with an oxygen, nitrogen, or sulfur atom;
(2) two carbon atoms are replaced with a sulfur and a nitrogen atom, an oxygen and a nitrogen atom, or two nitrogen atoms; or
(3) three carbon atoms are replaced with three nitrogen atoms, one oxygen and two nitrogen atoms, or one sulfur and two nitrogen atoms;
G-X-W is selected from:
(a) $(Z^1Z^2)C—N(R^1)—C(Z^1Z^2)$;
(b) $CH(R^1)—C(=O)—N(R^1)$; and
(c) $N(R^1)—C(=O)—CH(R^1)$;
$Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;
R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR^{1b}$, optionally substituted arylalkyl and optionally substituted heteroarylalkyl;
$R^1$ is independently selected from:
(a) H, optionally substituted alkyl, optionally substituted aryl, optionally substituted arylalkyl, optionally substituted heteroaryl and optionally substituted heteroarylalkyl;
(b) $C(=O)R^{1a}$;
(c) $OR^{1b}$;
(d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$;
$R^{1a}$ is independently selected from optionally substituted alkyl, optionally substituted aryl and optionally substituted heteroaryl;
$R^{1b}$ is independently selected from H and optionally substituted alkyl;
$R^{1c}$ and $R^{1d}$ are each independently selected from H, optionally substituted alkyl and a linking group of the formula $(CH_2)_2—X^1—(CH_2)_2$;
$X^1$ is independently selected from O, S and $CH_2$;
Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;
$R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;
$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;
$R^{2b}$ is selected from H and optionally substituted alkyl;
$R^{2c}$ and $R^{2d}$ are each independently selected from H and optionally substituted alkyl, or together form a linking group of the formula $(CH_2)_2—X^1—(CH_2)_2$;
$R^3$ and $R^4$ are each independently selected from:
(a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
(b) $CH_2OR^{14}$;
(c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
(d) $S(O)_yR^9$, $(CH_2)_pS(O)_yR^9$ and $CH_2S(O)_yR^{14}$;
(e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2-X^1-(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
(a) a direct bond;
(b) optionally substituted $CH_2$, $CH_2CH_2$ or $CH_2CH_2CH_2$, wherein said optional substituents are one to about three $R^{19}$ groups; and
(c) $CH=CH$, $CH(OH)-CH(OH)$, O, S, $S(=O)$, $S(=O)_2$, $C(R^{18})_2$, $C=C(R^{19})_2$, $C(=O)$, $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2-X^1-(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
(a) a direct bond;
(b) $NR^6$;
(c) optionally substituted $CH_2$, $CH_2CH_2$ or $CH_2CH_2CH_2$;
(d) $CR^{22}R^{24}$; and
(e) $CH=CH$, $CH(OH)CH(OH)$, O, S, $S(=O)$, $S(=O)_2$, $C(=O)$, $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, $Z'-CH_2$ and $CH_2Z'CH_2$;

Z' is selected from $C(R^{11})(OR^{12})$, O, S, $C(=O)$, $C(=NOR^{11})$ and $NR^{11}$;

$R^6$ is selected from H, $SO_2R^{2a}$, $CO_2R^{2a}$, $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

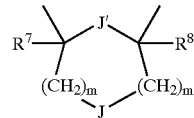

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2-X^3-CH_2$;

$X^3$ is a bond, O, S, or $NR^{10}$;

J is selected from a bond, O, $CH=CH$, S, $C(=O)$, $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, $CH(OH)CH(OH)$ and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

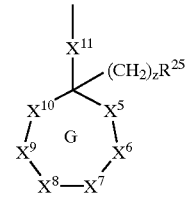

$X^5$ and $X^6$ are independently selected from O, N, S, $CHR^{26}$, $C(OH)R^{26}$, $C(=O)$ and $CH_2=C$;

$X^7$ and $X^8$ are independently selected from a bond, O, N, S, $CHR^{26}$, $C(OH)R^{26}$, $C(=O)$ and $CH_2=C$;

$X^9$ and $X^{10}$ are independently selected from a bond, O, N, S, $C(=O)$ and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein
(1) ring G contains 0 to about 3 ring heteroatoms;
(2) any two adjacent hydroxyl groups of ring G can be joined to form a dioxolane ring;

(3) any two adjacent ring carbon atoms of ring G can be joined to form a fused aryl or heteroaryl ring; with the provisos that:
(a) when $X^{11}$ is a bond, ring G can be heteroaryl; and
(b) ring G:
(i) contains at least one carbon atom that is saturated;
(ii) does not contain two adjacent ring O atoms;
(iii) contains a maximum of two C(=O) groups;

$R^{27}$ is selected from H and alkyl;
$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;
$R^{29}$ is selected from alkyl, aryl and heteroaryl;
$R^{30}$ is selected from H, alkyl, acyl and $C(=O)NR^{11}R^{12}$;
m is independently selected from 0, 1, and 2;
p is independently selected from 1, 2, 3, and 4;
r is independently selected from 0, 1, and 2;
y is independently selected from 0, 1 and 2; and
z is selected from 0, 1, 2, 3 and 4;
with the provisos that at least one of Y and Q' is a direct bond, when Y is a direct bond, Q' is other than a direct bond, when Q' is a direct bond, Y is other than a direct bond, and when rings B and F are phenyl, G-X-W is $CH_2NHC(=O)$, Y is a direct bond, Q is $NR^2$ and Q' is $NR^6$ where $R^6$ is joined with $R^2$ to form

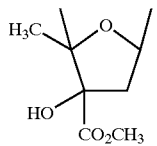

then $R^3$ is other than $CH_2SCH_2CH_3$.

As used herein, the term "sudden sensorineural hearing loss" refers to hearing loss developed as a result of idiopathic factors.

The present invention also provides methods for preserving function of sensory hair cells prior to or subsequent to trauma in a subject comprising administering to said subject an effective amount of a fused pyrrolocarbazole of Formula I having the formula:

FORMULA I

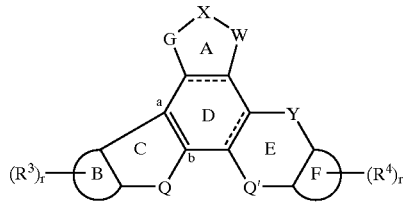

or a stereoisomer or pharmaceutically acceptable salt form thereof, wherein:
ring D is selected from phenyl and cyclohexene with double bond a-b;
ring B and ring F are independently selected from:
(a) a 6-membered carbocyclic ring in which from 1 to 3 carbon atoms may be replaced by heteroatoms;
(b) a 5-membered carbocyclic ring; and
(c) a 5-membered carbocyclic ring in which either:
(1) one carbon atom is replaced with an oxygen, nitrogen, or sulfur atom;
(2) two carbon atoms are replaced with a sulfur and a nitrogen atom, an oxygen and a nitrogen atom, or two nitrogen atoms; or
(3) three carbon atoms are replaced with three nitrogen atoms, one oxygen and two nitrogen atoms, or one sulfur and two nitrogen atoms;

G-X-W is selected from:
(a) $(Z^1Z^2)C-N(R^1)-C(Z^1Z^2)$;
(b) $CH(R^1)-C(=O)-N(R^1)$; and
(c) $N(R^1)-C(=O)-CH(R^1)$;

$Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;

R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR^{1b}$, optionally substituted arylalkyl and optionally substituted heteroarylalkyl;

$R^1$ is independently selected from:
(a) H, optionally substituted alkyl, optionally substituted aryl, optionally substituted arylalkyl, optionally substituted heteroaryl and optionally substituted heteroarylalkyl;
(b) $C(=O)R^{1a}$;
(c) $OR^{1b}$;
(d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$;

$R^{1a}$ is independently selected from optionally substituted alkyl, optionally substituted aryl and optionally substituted heteroaryl;
$R^{1b}$ is independently selected from H and optionally substituted alkyl;
$R^{1c}$ and $R^{1d}$ are each independently selected from H, optionally substituted alkyl and a linking group of the formula $(CH_2)_2-X^1-(CH_2)_2$;
$X^1$ is independently selected from O, S and $CH_2$;
Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;
$R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;
$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;
$R^{2b}$ is selected from H and optionally substituted alkyl;
$R^{2c}$ and $R^{2d}$ are each independently selected from H and optionally substituted alkyl, or together form a linking group of the formula $(CH_2)_2-X^1-(CH_2)_2$;
$R^3$ and $R^4$ are each independently selected from:
(a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
(b) $CH_2OR^{14}$;
(c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
(d) $S(O)_yR^9$, $(CH_2)_pS(O)_yR^9$ and $CH_2S(O)_yR^{14}$;

(e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2$—$X^1$—$(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
(a) a direct bond;
(b) optionally substituted $CH_2$, $CH_2CH_2$ or $CH_2CH_2CH_2$, wherein said optional substituents are one to about three $R^{19}$ groups; and
(c) CH=CH, CH(OH)—CH(OH), O, S, S(=O), $S(=O)_2$, $C(R^{18})_2$, $C=C(R^{19})_2$, $C(=O)$, $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2$—$X^1$—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
(a) a direct bond;
(b) $NR^6$;
(c) optionally substituted $CH_2$, $CH_2CH_2$ or $CH_2CH_2CH_2$;

(d) $CR^{22}R^{24}$; and
(e) CH=CH, CH(OH)CH(OH), O, S, S(=O), $S(=O)_2$, $C(=O)$, $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, Z'—$CH_2$ and $CH_2Z'CH_2$;

$Z^1$ is selected from $C(R^{11})(OR^{12})$, O, S, C(=O), $C(=NOR^{11})$ and $NR^{11}$;

$R^6$ is selected from H, $SO_2R^{2a}$, $CO_2R^{2a}$, $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

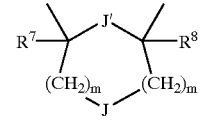

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2$—$X^3$—$CH_2$;

$X^3$ is a bond, O, S, or $NR^{10}$;

J is selected from a bond, O, CH=CH, S, C(=O), $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

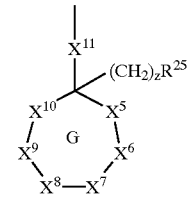

$X^5$ and $X^6$ are independently selected from O, N, S, $CHR^{26}$, $C(OH)R^{26}$, C(=O) and $CH_2$=C;

$X^7$ and $X^8$ are independently selected from a bond, O, N, S, $CHR^{26}$, $C(OH)R^{26}$, C(=O) and $CH_2$=C;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}CR^{1d}$;

$R^{26}$ is selected from H, optionally substituted alkyl and optionally substituted alkoxy, wherein
  (1) ring G contains 0 to about 3 ring heteroatoms;
  (2) any two adjacent hydroxyl groups of ring G can be joined to form a dioxolane ring;
  (3) any two adjacent ring carbon atoms of ring G can be joined to form a fused aryl or heteroaryl ring; with the provisos that:
    (a) when $X^{11}$ is a bond, ring G can be heteroaryl; and
    (b) ring G:
      (i) contains at least one carbon atom that is saturated;
      (ii) does not contain two adjacent ring O atoms;
      (iii) contains a maximum of two C(=O) groups;

$R^{27}$ is selected from H and alkyl;

$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;
  $R^{29}$ is selected from alkyl, aryl and heteroaryl;
  $R^{30}$ is selected from H, alkyl, acyl and $C(=O)NR^{11}R^{12}$;
  m is independently selected from 0, 1, and 2;
  p is independently selected from 1, 2, 3, and 4;
  r is independently selected from 0, 1, and 2;
  y is independently selected from 0, 1 and 2; and
  z is selected from 0, 1, 2, 3 and 4;

with the provisos that at least one of Y and Q' is a direct bond, when Y is a direct bond, Q' is other than a direct bond, when Q' is a direct bond, Y is other than a direct bond, and when rings B and F are phenyl, G-X-W is $CH_2NHC(=O)$, Y is a direct bond, Q is $NR^2$ and Q' is $NR^6$ where $R^6$ is joined with $R^2$ to form

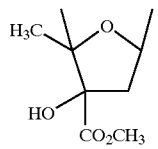

then $R^3$ is other than $CH_2SCH_2CH_3$.

As used herein, the term "preserving", in the context of preserving hair cell function and the like, refers to maintaining the normal function of one or more hair cells. As used herein, "preserving" may include, for example, maintaining at least about 50% of the function of a normal hair cell, more preferably at least about 75%, even more preferably at least about 80%, even more preferably at least about 85%, even more preferably at least about 90%, even more preferably at least about 95%, and most preferably about 100% of the normal function of the hair cell.

The present invention also provides methods for treating sensory hair cells that have been damaged comprising administering to said subject an effective amount of a fused pyrrolocarbazole of Formula I having the formula:

FORMULA I

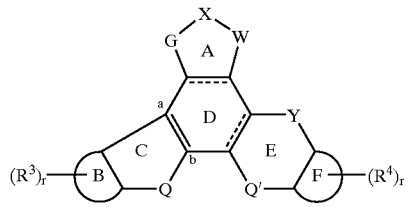

or a stereoisomer or pharmaceutically acceptable salt form thereof, wherein:
  ring D is selected from phenyl and cyclohexene with double bond a-b;
  ring B and ring F are independently selected from:
    (a) a 6-membered carbocyclic ring in which from 1 to 3 carbon atoms may be replaced by heteroatoms;
    (b) a 5-membered carbocyclic ring; and
    (c) a 5-membered carbocyclic ring in which either:
      (1) one carbon atom is replaced with an oxygen, nitrogen, or sulfur atom;
      (2) two carbon atoms are replaced with a sulfur and a nitrogen atom, an oxygen and a nitrogen atom, or two nitrogen atoms; or
      (3) three carbon atoms are replaced with three nitrogen atoms, one oxygen and two nitrogen atoms, or one sulfur and two nitrogen atoms;
  G-X-W is selected from:
    (a) $(Z^1Z^2)C-N(R^1)-C(Z^1Z^2)$;
    (b) $CH(R^1)-C(=O)-N(R^1)$; and
    (c) $N(R^1)-C(=O)-CH(R^1)$;
  $Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;
  R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR^{1b}$, optionally substituted arylalkyl and optionally substituted heteroarylalkyl;
  $R^1$ is independently selected from:
    (a) H, optionally substituted alkyl, optionally substituted aryl, optionally substituted arylalkyl, optionally substituted heteroaryl and optionally substituted heteroarylalkyl;
    (b) $C(=O)R^{1a}$;
    (c) $OR^{1b}$;
    (d) $C(=O)NHR^{1b}$, $NR^{1c}R^{1d}$, $(CH_2)_pNR^{1c}R^{1d}$, $(CH_2)_pOR^{1b}$, $O(CH_2)_pOR^{1b}$ and $O(CH_2)_pNR^{1c}R^{1d}$;
  $R^{1a}$ is independently selected from optionally substituted alkyl, optionally substituted aryl and optionally substituted heteroaryl;
  $R^{1b}$ is independently selected from H and optionally substituted alkyl;
  $R^{1c}$ and $R^{1d}$ are each independently selected from H, optionally substituted alkyl and a linking group of the formula $(CH_2)_2-X^1-(CH_2)_2$;
  $X^1$ is independently selected from O, S and $CH_2$;
  Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;
  $R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;

$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;

$R^{2b}$ is selected from H and optionally substituted alkyl;

$R^{2c}$ and $R^{2d}$ are each independently selected from H and optionally substituted alkyl, or together form a linking group of the formula $(CH_2)_2—X^1—(CH_2)_2$;

$R^3$ and $R^4$ are each independently selected from:
(a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
(b) $CH_2OR^{14}$;
(c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
(d) $S(O)_yR^9$, $(CH_2)_pS(O)_yR^9$ and $CH_2S(O)_yR^{14}$;
(e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2—X^1—(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
(a) a direct bond;
(b) optionally substituted $CH_2$, $CH_2CH_2$ or $CH_2CH_2CH_2$, wherein said optional substituents are one to about three $R^{19}$ groups; and
(c) CH=CH, CH(OH)—CH(OH), O, S, S(=O), $S(=O)_2$, $C(R^{18})_2$, $C=C(R^{19})_2$, C(=O), $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2—X^1—(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
(a) a direct bond;
(b) $NR^6$;
(c) optionally substituted $CH_2$, $CH_2CH_2$ or $CH_2CH_2CH_2$;
(d) $CR^{22}R^{24}$; and
(e) CH=CH, CH(OH)CH(OH), O, S, S(=O), $S(=O)_2$, C(=O), $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, $Z'—CH_2$ and $CH_2Z'CH_2$;

Z' is selected from $C(R^{11})(OR^{12})$, O, S, C(=O), $C(=NOR^{11})$ and $NR^{11}$;

$R^6$ is selected from H, $SO_2R^{2a}$, $CO_2R^{2a}$, $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

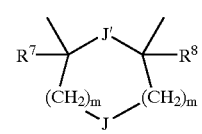

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2—X^3—CH_2$;

$X^3$ is a bond, O, S, or $NR^{10}$;

J is selected from a bond, O, CH=CH, S, C(=O), $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

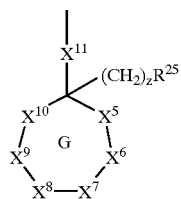

$X^5$ and $X^6$ are independently selected from O, N, S, $CHR^{26}$, $C(OH)R^{26}$, $C(=O)$ and $CH_2=C$;

$X^7$ and $X^8$ are independently selected from a bond, O, N, S, $CHR^{26}$, $C(OH)R^{26}$, $C(=O)$ and $CH_2=C$;

$X^9$ and $X^{10}$ are independently selected from a bond, O, N, S, $C(=O)$ and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein
(1) ring G contains 0 to about 3 ring heteroatoms;
(2) any two adjacent hydroxyl groups of ring G can be joined to form a dioxolane ring;
(3) any two adjacent ring carbon atoms of ring G can be joined to form a fused aryl or heteroaryl ring; with the provisos that:
(a) when $X^{11}$ is a bond, ring G can be heteroaryl; and
(b) ring G:
(i) contains at least one carbon atom that is saturated;
(ii) does not contain two adjacent ring O atoms;
(iii) contains a maximum of two $C(=O)$ groups;

$R^{27}$ is selected from H and alkyl;

$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;

$R^{29}$ is selected from alkyl, aryl and heteroaryl;

$R^{30}$ is selected from H, alkyl, acyl and $C(=O)NR^{11}R^{12}$;

m is independently selected from 0, 1, and 2;

p is independently selected from 1, 2, 3, and 4;

r is independently selected from 0, 1, and 2;

y is independently selected from 0, 1 and 2; and z is selected from 0, 1, 2, 3 and 4;

with the provisos that at least one of Y and Q' is a direct bond, when Y is a direct bond, Q' is other than a direct bond, when Q' is a direct bond, Y is other than a direct bond, and when rings B and F are phenyl, G—X—W is $CH_2NHC(=O)$, Y is a direct bond, Q is $NR^2$ and Q' is $NR^6$ where $R^6$ is joined with $R^2$ to form

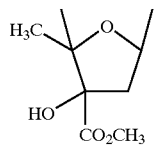

then $R^3$ is other than $CH_2SCH_2CH_3$.

As used herein, the term "treating", in the context of treating damaged sensory hair cells, refers to the restoration or recovery of the ability to perceive and/or transduce sensory stimuli of at least some of the hair cells damaged due to a trauma. As used herein, "treating" may include recovering at least about 15%, more preferably at least about 25%, even more preferably at least about 50%, even more preferably at least about 75%, even more preferably at least about 80%, even more preferably at least about 85%, even more preferably at least about 90%, even more preferably at least about 95%, and most preferably about 100% of the ability of a normal hair cell to perceive and/or transduce sensory stimuli of at least some of the hair cells damaged due to a trauma.

As used herein, the term "damaged" refers to one or more sensory hairs cell that, due to a trauma, is less able to perceive and/or transduce an external stimuli than a normal sensory hair cell.

As used herein, the term "trauma" includes, but is not limited to noise, infection, drug toxicity, aging, disease and idiopathic effects.

The present invention also provides methods for treating sensory hair cells that have been damaged comprising administering to said subject an effective amount of a fused pyrrolocarbazole of Formula I having the formula:

FORMULA I

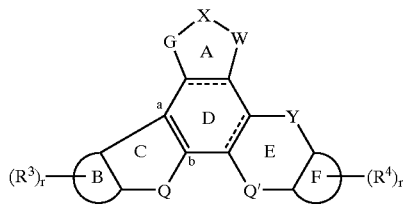

or a stereoisomer or pharmaceutically acceptable salt form thereof, wherein:

ring D is selected from phenyl and cyclohexene with double bond a–b;

ring B and ring F are independently selected from:
(a) a 6-membered carbocyclic ring in which from 1 to 3 carbon atoms may be replaced by heteroatoms;
(b) a 5-membered carbocyclic ring; and
(c) a 5-membered carbocyclic ring in which either:
(1) one carbon atom is replaced with an oxygen, nitrogen, or sulfur atom;
(2) two carbon atoms are replaced with a sulfur and a nitrogen atom, an oxygen and a nitrogen atom, or two nitrogen atoms; or
(3) three carbon atoms are replaced with three nitrogen atoms, one oxygen and two nitrogen atoms, or one sulfur and two nitrogen atoms;

G—X—W is selected from:
(a) $(Z^1Z^2)C—N(R^1)—C(Z^1Z^2)$;
(b) $CH(R^1)—C(=O)—N(R^1)$; and
(c) $N(R^1)—C(=O)—CH(R^1)$;

$Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;

R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR^{1b}$, optionally substituted arylalkyl and optionally substituted heteroarylalkyl;

$R^1$ is independently selected from:
  (a) H, optionally substituted alkyl, optionally substituted aryl, optionally substituted arylalkyl, optionally substituted heteroaryl and optionally substituted heteroarylalkyl;
  (b) $C(=O)R^{1a}$;
  (c) $OR^{1b}$;
  (d) $C(=O)NHR^{1b}, NR^{1c}R^{1d}$, $(CH_2)_pNR^{1c}R^{1d}$, $(CH_2)_pOR^{1b}$, $O(CH_2)_pOR_{1b}$ and $O(CH_2)_pNR^{1c}R^{1d}$;

$R^{1a}$ is independently selected from optionally substituted alkyl, optionally substituted aryl and optionally substituted heteroaryl;

$R_{1b}$ is independently selected from H and optionally substituted alkyl;

$R^{1c}$ and $R^{1d}$ are each independently selected from H, optionally substituted alkyl and a linking group of the formula $(CH_2)_2$—$X^1$—$(CH_2)_2$;

$X^1$ is independently selected from O, S and $CH_2$;

Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;

$R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three R' groups;

$R^{2a}$, is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;

$R^{2b}$ is selected from H and optionally substituted alkyl;

$R^{2c}$ and $R^{2d}$ are each independently selected from H and optionally substituted alkyl, or together form a linking group of the formula $(CH_2)_2$—$X^1$—$(CH_2)_2$;

$R^3$ and $R^4$ are each independently selected from:
  (a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
  (b) $CH_2OR^{14}$;
  (c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
  (d) $S(O)_yR^9$, $(CH_2)_pS(O)_yR^9$ and $CH_2S(O)_yR^{14}$;
  (e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2$—$X^1$—$(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
  (a) a direct bond;
  (b) optionally substituted $CH_2$, $CH_2CH_2$ or $CH_2CH_2CH_2$, wherein said optional substituents are one to about three $R^{19}$ groups; and
  (c) $CH=CH$, $CH(OH)$—$CH(OH)$, O, S, $S(=O)$, $S(=O)_2$, $C(R^{18})_2$, $C=C(R^{19})_2$, $C(=O)$, $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2$—$X^1$—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
  (a) a direct bond;
  (b) $NR^6$;
  (c) optionally substituted $CH_2$, $CH_2CH_2$ or $CH_2CH_2CH_2$;
  (d) $CR^{22}R^{24}$; and
  (e) $CH=CH$, $CH(OH)CH(OH)$, O, S, $S(=O)$, $S(=O)_2$, $C(=O)$, $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, $Z'$—$CH_2$ and $CH_2Z'CH_2$;

$Z'$ is selected from $C(R^{11})(OR^{12})$, O, S, $C(=O)$, $C(=NOR^{11})$ and $NR^{11}$;

$R^6$ is selected from H, $SO_2R^{2a}$, $CO_2R^{2a}$, $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

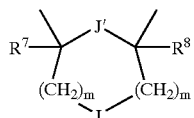

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2-X^3-CH_2$;

$X^3$ is a bond, O, S, or $NR^{10}$;

J is selected from a bond, O, CH=CH, S, C(=O), $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

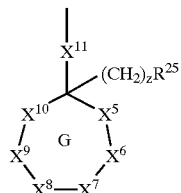

$X^5$ and $X^6$ are independently selected from O, N, S, $CHR^{26}$, $C(OH)R^{26}$, C(=O) and $CH_2=C$;

$X^7$ and $X^8$ are independently selected from a bond, O, N, S, $CHR^{26}$, $C(OH)R^{26}$, C(=O) and $CH_2=C$;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein
  (1) ring G contains 0 to about 3 ring heteroatoms;
  (2) any two adjacent hydroxyl groups of ring G can be joined to form a dioxolane ring;
  (3) any two adjacent ring carbon atoms of ring G can be joined to form a fused aryl or heteroaryl ring; with the provisos that:
    (a) when $X^{11}$ is a bond, ring G can be heteroaryl; and
    (b) ring G:
      (i) contains at least one carbon atom that is saturated;
      (ii) does not contain two adjacent ring O atoms;
      (iii) contains a maximum of two C(=O) groups;

$R^{27}$ is selected from H and alkyl;

$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;

$R^{29}$ is selected from alkyl, aryl and heteroaryl;

$R^{30}$ is selected from H, alkyl, acyl and $C(=O)NR^{11}R^{12}$;

m is independently selected from 0, 1, and 2;

p is independently selected from 1, 2, 3, and 4;

r is independently selected from 0, 1, and 2;

y is independently selected from 0, 1 and 2; and z is selected from 0, 1, 2, 3 and 4;

with the provisos that at least one of Y and Q' is a direct bond, when Y is a direct bond, Q' is other than a direct bond, when Q' is a direct bond, Y is other than a direct bond, and when rings B and F are phenyl, G—X—W is $CH_2NHC(=O)$, Y is a direct bond, Q is $NR^2$ and Q' is $NR^6$ where $R^6$ is joined with $R^2$ to form

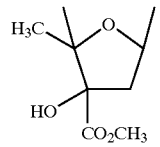

then $R^3$ is other than $CH_2SCH_2CH_3$.

The present invention also provides methods for preventing death of cochlear neurons in a subject comprising administering to said subject an effective amount of a fused pyrrolocarbazole of Formula I having the formula:

FORMULA I

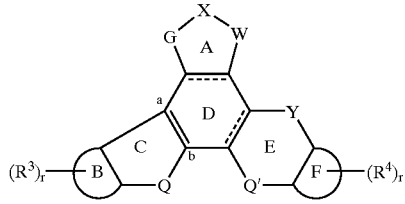

or a stereoisomer or pharmaceutically acceptable salt form thereof, wherein:

ring D is selected from phenyl and cyclohexene with double bond a–b; ring B and ring F are independently selected from:
  (a) a 6-membered carbocyclic ring in which from 1 to 3 carbon atoms may be replaced by heteroatoms;
  (b) a 5-membered carbocyclic ring; and
  (c) a 5-membered carbocyclic ring in which either:
    (1) one carbon atom is replaced with an oxygen, nitrogen, or sulfur atom;
    (2) two carbon atoms are replaced with a sulfur and a nitrogen atom, an oxygen and a nitrogen atom, or two nitrogen atoms; or
    (3) three carbon atoms are replaced with three nitrogen atoms, one oxygen and two nitrogen atoms, or one sulfur and two nitrogen atoms;

G—X—W is selected from:
  (a) $(Z^1Z^2)C-N(R^1)-C(Z^1Z^2)$;
  (b) $CH(R^1)-C(=O)-N(R^1)$; and
  (c) $N(R^1)-C(=O)-CH(R^1)$;

$Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;

R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR^{1b}$, optionally substituted arylalkyl and optionally substituted heteroarylalkyl;

$R^1$ is independently selected from:
  (a) H, optionally substituted alkyl, optionally substituted aryl, optionally substituted arylalkyl, optionally substituted heteroaryl and optionally substituted heteroarylalkyl;
  (b) $C(=O)R^{1a}$;
  (c) $OR^{1b}$;
  (d) $C(=O)NHR^{1b}$, $NR^{1c}R^{1d}$, $(CH_2)_pNR^{1c}R^{1d}$, $(CH_2)_pOR^{1b}$, $O(CH_2)_pOR_{1b}$ and $O(CH_2)_pNR^{1c}R^{1d}$;

$R^{1a}$ is independently selected from optionally substituted alkyl, optionally substituted aryl and optionally substituted heteroaryl;

$R_{1b}$ is independently selected from H and optionally substituted alkyl;

$R^{1c}$ and $R^{1d}$ are each independently selected from H, optionally substituted alkyl and a linking group of the formula $(CH_2)_2$—$X^1$—$(CH_2)_2$;

$X^1$ is independently selected from O, S and $CH_2$;

Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;

$R^2$ is selected from H, $SO_2R^{2a}$, $CO_2R^{2a}$, $C(=O)R^{2a}$, $C(=O)NR^{2c}R^{2d}$ optionally substituted alkyl, optionally substituted alkenyl and optionally substituted alkynyl, wherein said optional substituents are one to about three $R^5$ groups;

$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;

$R^{2b}$ is selected from H and optionally substituted alkyl;

$R^{2c}$ and $R^{2d}$ are each independently selected from H and optionally substituted alkyl, or together form a linking group of the formula $(CH_2)_2$—$X^1$—$(CH_2)_2$;

$R^3$ and $R^4$ are each independently selected from:
  (a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
  (b) $CH_2OR^{14}$;
  (c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
  (d) $S(O)_yR^9$, $(CH_2)_pS(O)_yR^9$ and $CH_2S(O)_yR^{14}$;
  (e) optionally substituted alkyl, optionally substituted alkenyl and optionally substituted alkynyl, wherein said optional substituents are one to about three $R^5$ groups;

$R^9$ is selected from alkyl, $(CH_2)_raryl$ and $(CH_2)_rheteroaryl$;

$R^{10}$ is selected from H, alkyl, $(CH_2)_raryl$ and $(CH_2)_rheteroaryl$;

$R^{11}$ and $R^{12}$ are independently selected from H and optionally substituted alkyl, or together form a linking group of the formula $(CH_2)_2$—$X^1$—$(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
  (a) a direct bond;
  (b) optionally substituted $CH_2$, $CH_2CH_2$ or $CH_2CH_2CH_2$, wherein said optional substituents are one to about three $R^{19}$ groups; and
  (c) $CH=CH$, $CH(OH)$—$CH(OH)$, O, S, $S(=O)$, $S(=O)_2$, $C(R^{18})_2$, $C=C(R^{19})_2$, $C(=O)$, $C(=NOR^{20})$, $C(OR^{20})R^{20}$, $C(=O)CH(R^{18})$, $CH(R^{18})C(=O)$, $C(=NOR^{20})CH(R^{18})$, $CHR21C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR^{18c}R^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2$—$X^1$—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
  (a) a direct bond;
  (b) $NR^6$;
  (c) optionally substituted $CH_2$, $CH_2CH_2$ or $CH_2CH_2CH_2$;
  (d) $CR^{22}R^{24}$; and
  (e) $CH=CH$, $CH(OH)CH(OH)$, O, S, $S(=O)$, $S(=O)_2$, $C(=O)$, $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, $Z'$-$CH_2$ and $CH_2Z'CH_2$;

$Z^1$ is selected from $C(R^{11})(OR^{12})$, O, S, $C(=O)$, $C(=NOR^{11})$ and $NR^{11}$;

$R^6$ is selected from H, $SO_2R^{2a}$, $CO_2R^{2a}$, $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

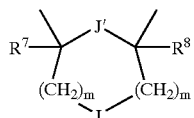

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2-X^3-CH_2$;

$X^3$ is a bond, O, S, or $NR^{10}$;

J is selected from a bond, O, CH=CH, S, C(=O), $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

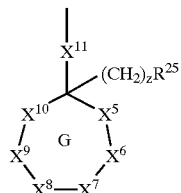

$X^5$ and $X^6$ are independently selected from O, N, S, $CHR^{26}$, $C(OH)R^{26}$, C(=O) and $CH_2=C$;

$X^7$ and $X^8$ are independently selected from a bond, O, N, S, $CHR^{26}$, $C(OH)R^{26}$, C(=O) and $CH_2=C$;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein
(1) ring G contains 0 to about 3 ring heteroatoms;
(2) any two adjacent hydroxyl groups of ring G can be joined to form a dioxolane ring;
(3) any two adjacent ring carbon atoms of ring G can be joined to form a fused aryl or heteroaryl ring; with the provisos that:
  (a) when $X^{11}$ is a bond, ring G can be heteroaryl; and
  (b) ring G:
    (i) contains at least one carbon atom that is saturated;
    (ii) does not contain two adjacent ring O atoms;
    (iii) contains a maximum of two C(=O) groups;

$R^{27}$ is selected from H and alkyl;

$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;

$R^{29}$ is selected from alkyl, aryl and heteroaryl;

$R^{30}$ is selected from H, alkyl, acyl and $C(=O)NR^{11}R^{12}$;

m is independently selected from 0, 1, and 2;

p is independently selected from 1, 2, 3, and 4;

r is independently selected from 0, 1, and 2;

y is independently selected from 0, 1 and 2; and z is selected from 0, 1, 2, 3 and 4;

with the provisos that at least one of Y and Q' is a direct bond, when Y is a direct bond, Q' is other than a direct bond, when Q' is a direct bond, Y is other than a direct bond, and when rings B and F are phenyl, G—X—W is $CH_2NHC(=O)$, Y is a direct bond, Q is $NR^2$ and Q' is $NR^6$ where $R^6$ is joined with $R^2$ to form

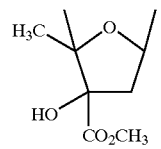

then $R^3$ is other than $CH_2SCH_2CH_3$.

As used herein, the term "death of cochlear neurons" refers to a cessation of the ability of a neuron to transmit impulses from its input source to a final destination, as compared with a normally functioning neuron.

The present invention also provides methods for preventing death of cochlear neurons in a subject comprising administering to said subject an effective amount of a fused pyrrolocarbazole of Formula 1 having the formula:

FORMULA I

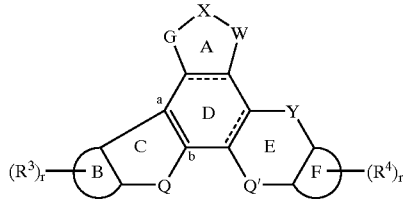

or a stereoisomer or pharmaceutically acceptable salt form thereof, wherein:

ring D is selected from phenyl and cyclohexene with double bond a–b;

ring B and ring F are independently selected from:
(a) a 6-membered carbocyclic ring in which from 1 to 3 carbon atoms may be replaced by heteroatoms;
(b) a 5-membered carbocyclic ring; and
(c) a 5-membered carbocyclic ring in which either:
  (1) one carbon atom is replaced with an oxygen, nitrogen, or sulfur atom;
  (2) two carbon atoms are replaced with a sulfur and a nitrogen atom, an oxygen and a nitrogen atom, or two nitrogen atoms; or
  (3) three carbon atoms are replaced with three nitrogen atoms, one oxygen and two nitrogen atoms, or one sulfur and two nitrogen atoms;

G—X—W is selected from:
   (a) $(Z^1Z^2)C$—$N(R^1)$—$C(Z^1Z^2)$;
   (b) $CH(R^1)$—$C(=O)$—$N(R^1)$; and
   (c) $N(R^1)$—$C(=O)$—$CH(R^1)$;

$Z^1$ and $Z^2$, at each occurrence, are independently selected from H, H; H, OR; H, SR; H, $N(R)_2$; and a group wherein $Z^1$ and $Z^2$ together form a moiety selected from =O, =S, and =NR; with the proviso that at least one of the pairs $Z^1$ and $Z^2$ forms =O;

R is independently selected from H, optionally substituted alkyl, OH, alkoxy, $OC(=O)R^{1a}$, $OC(=O)NR^{1c}R^{1d}$, $O(CH_2)_pNR^{1c}R^{1d}$, $O(CH_2)_pOR$ optionally substituted arylalkyl and optionally substituted heteroarylalkyl;

$R^1$ is independently selected from:
   (a) H, optionally substituted alkyl, optionally substituted aryl, optionally substituted arylalkyl, optionally substituted heteroaryl and optionally substituted heteroarylalkyl;
   (b) $C(=O)R^{1a}$;
   (c) OR;
   (d) $C(=O)NHR^{1b}$, $NR^{1c}R^{1d}$, $(CH_2)_pNR^{1c}R^{1d}$, $(CH_2)_pOR^{1b}$, $O(CH_2)_pOR_{1b}$ and $O(CH_2)_pNR^{1c}R^{1d}$;

$R^{1a}$ is independently selected from optionally substituted alkyl, optionally substituted aryl and optionally substituted heteroaryl;

$R^{1b}$ is independently selected from H and optionally substituted alkyl;

$R^{1c}$ and $R^{1d}$ are each independently selected from H, optionally substituted alkyl and a linking group of the formula $(CH_2)_2$—$X^1$—$(CH_2)_2$;

$X^1$ is independently selected from O, S and $CH_2$;

Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;

$R^2$ is selected from H, $SO_2R^{2a}$, $CO_2R^{2a}$, $C(=O)R^{2a}$, $C(=O)NR^{2c}R^{2d}$, optionally substituted alkyl, optionally substituted alkenyl and optionally substituted alkynyl, wherein said optional substituents are one to about three $R^5$ groups;

$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;

$R^{2b}$ is selected from H and optionally substituted alkyl;

$R^{2c}$ and $R^{2d}$ are each independently selected from H and optionally substituted alkyl, or together form a linking group of the formula $(CH_2)_2$—$X^1$—$(CH_2)_2$;

$R^3$ and $R^4$ are each independently selected from:
   (a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{10}$, $CH_2OR^{10}$, $NR^{11}R^{12}$, $NR^{10}S(=O)_2R^9$ and $NR^{10}C(=O)R^9$;
   (b) $CH_2OR^{14}$;
   (c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
   (d) $S(O)_yR^9$, $(CH_2)_pS(O)_yR^9$ and $CH_2S(O)_yR^{14}$;
   (e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2$—$X^1$—$(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{11})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
   (a) a direct bond;
   (b) optionally substituted $CH_2$, $CH_2CH_2$ or $CH_2CH_2CH_2$, wherein said optional substituents are one to about three $R^{19}$ groups; and
   (c) CH=CH, CH(OH)—CH(OH), O, S, $S(=O)$, $S(=O)_2$, $C(R^{18})_2$, $C=C(R^{19})_2$, $C(=O)$, $C(=NOR^{20})$ $C(OR^{20})R^{20}$, $C(=O)CH(R^{18})$, $CH(R^{18})C(=O)$, $C(=NOR^{20})CH(R^{18})$, $CHR^{20}$ $C(=NOR^{20})$, $C(=O)N(R^{21})$, $N(R^{21})C(=O)$, $CH_2Z$, $ZCH_2$ and $CH_2ZCH_2$, where Z is selected from $C(R^{20})_2$, O, S, $CO_2R^{20}$, $C(=NOR^{20})$ and $N(R^{20})$;

$R^{18}$ is independently selected from H, $SO_2R^{18a}$, $CO_2R^{18}$, $C(=O)R^{18a}$ $C(=O)NR^{18}CR^{18d}$, optionally substituted alkyl, optionally substituted alkenyl, and optionally substituted alkynyl;

$R^{18a}$ is independently selected from optionally substituted alkyl, optionally substituted aryl, optionally substituted carbocyclyl and optionally substituted heterocyclyl;

$R^{18c}$ and $R^{18d}$ are each independently selected from H and optionally substituted alkyl, or together form a linking group of the formula $(CH_2)_2$—$X^1$—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
   (a) a direct bond;
   (b) $NR^6$;
   (c) optionally substituted $CH_2$, $CH_2CH_2$ or $CH_2CH_2CH_2$;
   (d) $CR^{22}R^{24}$; and
   (e) CH=CH, CH(OH)CH(OH), O, S, $S(=O)$, $S(=O)_2$, $C(=O)$, $C(=NOR^{11})$, $C(OR^{11})(R^{12})$, $C(=O)CH(R^{13})$, $CH(R^{13})C(=O)$, $C(R^{10})_2$, $C(=NOR^{11})CH(R^{13})$, $CH(R^{13})C(=NOR^{11})$, $CH_2Z'$, $Z'$—$CH_2$ and $CH_2Z'CH_2$;

Z' is selected from $C(R^{11})(OR^{12})$, O, S, $C(=O)$, $C(=NOR^{11})$ and $NR^{11}$;

$R^6$ is selected from H, $SO_2R^{2a}$, $CO_2R^{2a}$, $C(=O)R^{2a}$, $C(=O)NR^{1c}R^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or $C(R^{10})_2$, $R^2$ and $R^6$ or one of $R^{10}$ are joined together to form:

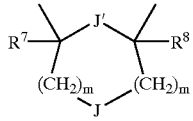

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2-X^3-CH_2$; $X^3$ is a bond, O, S, or $NR^{10}$;

J is selected from a bond, O, CH=CH, S, C(=O), $CH(OR^{10})$, $N(R^{10})$, $N(OR^{10})$, $CH(NR^{11}R^{12})$, $C(=O)N(R^{17})$, $N(R^{17})C(=O)$, $N(S(O)_yR^9)$, $N(S(O)_yNR^{11}R^{12})$, $N(C(=O)R^{17})$, $C(R^{15}R^{16})$, $N^+(O^-)(R^{10})$, CH(OH)CH(OH) and $CH(O(C=O)R^9)CH(OC(=O)R^9)$;

J' is selected from O, S, $N(R^{10})$, $N^+(O^-)(R^{10})$, $N(OR^{10})$ and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, $C(=O)R^{10}$, $O(C=O)R^9$, alkyl-OH, alkoxy and $CO_2R^{10}$;

$R^{17}$ is selected from H, alkyl, aryl and heteroaryl;

$R^{22}$ is

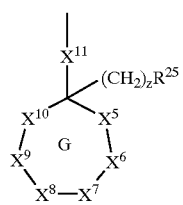

$X^5$ and $X^6$ are independently selected from O, N, S, $CHR^{26}$, $C(OH)R^{26}$, C(=O) and $CH_2=C$;

$X^7$ and $X^8$ are independently selected from a bond, O, N, S, $CHR^{26}$, $C(OH)R^{26}$, C(=O) and $CH_2=C$;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and $OC(=O)NR^{1c}R^{1d}$;

$R^{26}$ is selected from H, optionally substituted alkyl and optionally substituted alkoxy, wherein (1) ring G contains 0 to about 3 ring heteroatoms;
(2) any two adjacent hydroxyl groups of ring G can be joined to form a dioxolane ring;
(3) any two adjacent ring carbon atoms of ring G can be joined to form a fused aryl or heteroaryl ring; with the provisos that:

(a) when $X^{11}$ is a bond, ring G can be heteroaryl; and
(b) ring G:
   (i) contains at least one carbon atom that is saturated;
   (ii) does not contain two adjacent ring O atoms;
   (iii) contains a maximum of two C(=O) groups;

$R^{27}$ is selected from H and alkyl;

$R^{28}$ is selected from aryl, arylalkyl, $SO_2R^{29}$, $CO_2R^{29}$, $C(=O)R^{29}$, optionally substituted alkyl, optionally substituted alkenyl and optionally substituted alkynyl;

$R^{29}$ is selected from alkyl, aryl and heteroaryl;

$R^{30}$ is selected from H, alkyl, acyl and $C(=O)NR^{11}R^{12}$;

m is independently selected from 0, 1, and 2;

p is independently selected from 1, 2, 3, and 4;

r is independently selected from 0, 1, and 2;

y is independently selected from 0, 1 and 2; and z is selected from 0, 1, 2, 3 and 4;

with the provisos that at least one of Y and Q' is a direct bond, when Y is a direct bond, Q' is other than a direct bond, when Q' is a direct bond, Y is other than a direct bond, and when rings B and F are phenyl, G—X—W is $CH_2NHC(=O)$, Y is a direct bond, Q is $NR^2$ and Q' is $NR^6$ where $R^6$ is joined with $R^2$ to form

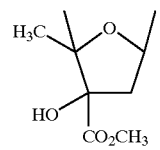

then $R^3$ is other than $CH_2SCH_2CH_3$.

In an alternative embodiment, the methods of the present invention may involve a compound of Formula II which is a small organic molecule that is a derivative of the indolocarbazole K-252a. The compound of Formula II has been shown to prevent death of motorneurons in vitro by inhibiting the JNK signaling pathway associated with stress and injury (Maroney et al., J. Neuroscience, 18(1), 104–111, 1998).

The compound of Formula II is a bis-thioethylmethyl analog of K-252a. Modifications of Formula II which retain functional activity are also contemplated. As used herein, the term "functional activity" refers to the ability of the composition to prevent hearing loss, prevent loss of sense of balance, prevent the death of sensory hair cells, prevent sudden sensorineural hearing loss due to the loss of sensory hair cells, preserve function of sensory hair cells prior to or subsequent to trauma, treat damaged sensory hair cells, prevent death of cochlear neurons. The compound of Formula II has an indolocarbazole skeleton and the structure shown below.

FORMULA II

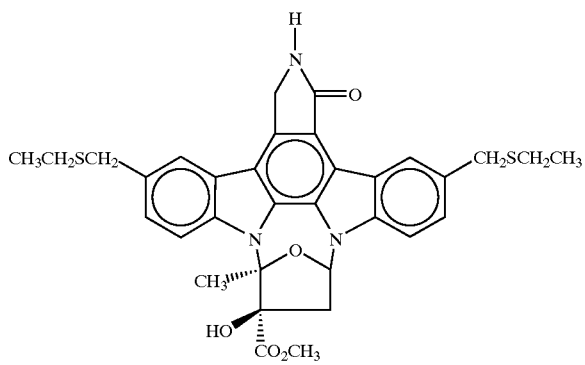

The present invention also provides methods for preventing hearing loss in a subject comprising administering to said subject an effective amount of the compound of Formula II;

FORMULA II

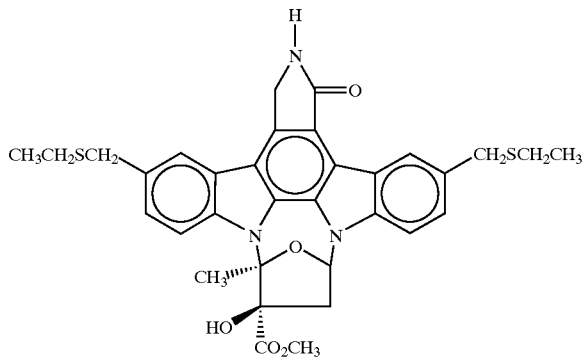

The present invention further provides methods for preventing loss of sense of balance in a subject comprising administering to said subject an effective amount of the compound of Formula II;

FORMULA II

The present invention further provides methods for preventing death of sensory hair cells in a subject comprising administering to said subject an effective amount of the compound of Formula II;

FORMULA II

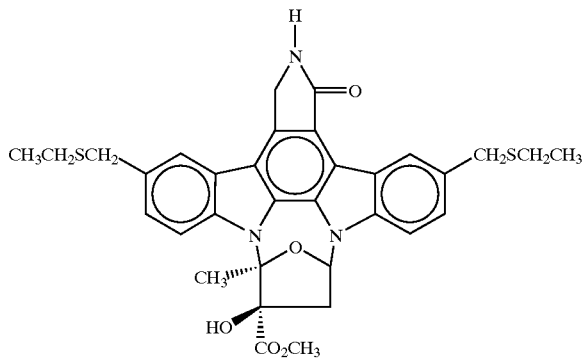

The present invention further provides methods for preventing sudden sensorineural hearing loss in a subject due to death of sensory hair cells comprising administering to said subject an effective amount of the compound of Formula II, defined above.

The present invention also provides methods for preserving function of sensory hair cells prior to or subsequent to trauma in a subject comprising administering to said subject an effective amount of the compound of Formula II, defined above.

The present invention further provides methods for preventing death of cochlear neurons in a subject comprising administering to said subject a therapeutically effective amount of the compound of Formula II, defined above.

Indolocarbazoles are generally lypophilic and, therefore, are able to cross biological membranes much more readily than proteins. Further, indolocarbazoles can have much longer half lives in vivo than do polypeptides.

K-252a derivatives have promise for disorders such as Alzheimer's disease, motor neuron disease, Parkinson's disease, Huntington's disease and epilepsy (See, for example, U.S. Pat. No. 5,461,146, issued Oct. 24, 1995; U.S. Pat. No. 5,621,100, issued Apr. 15, 1997).

The compounds of Formula I and Formula II may also be useful in the treatment of peripheral or central nerve disorders, and cytokine overproduction (See PCT/WO97/49406, International Publication Date Dec. 31, 1997, the disclosures of which are hereby incorporated herein by reference, in their entirety).

In another alternate embodiment, the methods of the present invention may involve compounds which are intermediates in the preparation of the compounds of Formulas I and II. Examplary of such intermediate compounds include, for example, the compounds identified as 5 in Example 11, and 1, 2, 3, 4, 5, 6, 7, and 8 in Example 12. A particularly preferred intermediate compound is compound 7 in Example 12.

The cochlea is an useful biological model system for studies on the protective therapeutic potential of various substances on sensory hair cells. The function of the cochlea can be accurately monitored at two levels; at the level of the organ of Corti by measuring cochlear microphonic potentials and otoacoustic emissions, and at the level of the cochlear nerve by measuring compound action potentials, summating potentials, or auditory brainstem responses, ABRs. Additionally, the quantity of sensory hair cells and cochlear neurons in the Organ of Corti is well known and trauma-induced changes can be accurately evaluated by morphometric methods including cytocochleograms and neuronal counts. Following experimentally-induced lesions, the pattern of degeneration and the sequence of events in the mammalian auditory organ are well known. The sensory hair cells are the primary targets of noise and ototoxic drugs. We know today what kind of noise or dosage of ototoxic drugs induces destruction of sensory hair cells at locations in the inner ear. When the sensory hair cells are destroyed, the innervating cochlear neurons degenerate secondarily.

The fused pyrrolocarbazoles of the present invention may exist in prodrug form. As used herein, the term "prodrug" is intended to include any covalently bonded carriers which release the active parent drug according to Formulas I and/or II or other formulas or compounds of the present invention in vivo when such prodrug is administered to a mammalian subject. Since prodrugs are known to enhance numerous desirable qualities of pharmaceuticals (e.g., solubility, bioavailability, manufacturing, etc.), the compounds of the present invention may be delivered in prodrug form. Thus, the present invention contemplates prodrugs of the claimed compounds, compositions containing the same, and methods of delivering the same. Prodrugs of a compound of the present invention, for example Formulas I and II, may be prepared by modifying functional groups present in the compound in such a way that the modifications are cleaved, either in routine manipulation or in vivo, to the parent compound.

Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. For example, amino acid side chain substituents of the present compounds may be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., *Protective Groups in Organic Synthesis* 2d. Ed., Wiley & Sons, 1991.

Fused pyrrolocarbazoles, such as indolocarbazoles may be synthesized by methods taught, for example, in U.S. Pat. Nos. 4,923,986; 4,877,776; 5,093,330; 5,461,146; 5,468,872; 5,621,100; 5,621,101; 5,516,771; and 5,599,808; and PCT publication Nos. WO 93/08809 and WO 97/46565, the discloses of which are hereby incorporated herein by reference, in their entireties. Additional methods of preparation are set forth in Moody et al., *J. Org. Chem.* 57:2105–2114 (1992), also incorporated herein by reference.

Fused pyrrolocarbazoles, such as indenocarbazoles, as well as additional compounds wherein Q' is not a single nitrogen, may be synthesized by methods taught, for example, in U.S. Pat. Nos. 5,475110; 5,591,855; 5,594,009; 5,705,511; 5,616,724; and 5,801,190; the disclosures of which are hereby incorporated herein by reference in their entireties.

Fused pyrrolocarbazoles, such as bridged indenocarbazoles, may be prepared by methods taught, for example, in copending U.S. patent application Ser. No. 09/325,140, the disclosure of which is hereby incorporated herein by reference in its entirety.

Fused pyrrolocarbazoles, such as cyclic substituted pyrrolocarbazoles and isoindolones, may be prepared by methods taught, for example, in copending U.S. Provisional Application Ser. No. 60/119,834, the disclosures of which are hereby incorporated by reference, in their entireties.

The invention is set forth in more detail in the examples below. The following examples are meant to illustrate the invention and are not to be construed to limit the invention in any way. Those skilled in the art will recognize modifications that are within the spirit and scope of the invention. All references cited herein are hereby incorporated by reference in their entirety.

EXAMPLE 1

Prevention of Hearing Impairment/Cell Death

Baseline hearing of 8 pigmented guinea pigs (200–300 g) was tested by ABR as described below. ABR is a measure of hearing function. Four animals were treated with daily subcutaneous (s.c.) injections of the compound of Formula II, 1 mg/kg, starting 24 hours prior to noise trauma and lasting until 21 days after exposure to the noise trauma. Four animals served as controls and received only vehicle (the fourth animal died under anaesthesia). All the animals were exposed to traumatic octave band noise, center frequency 4.0 kHz, 125 dB SPL (sound pressure level) for 105 min.

ABR thresholds were again determined 21 days after exposure to the noise trauma. ABR thresholds were measured with System II hardware and BioSig software (Tucker Davis Technology). Stimulus with 1 ms cos2 rise and fall and 18 ms plateau was presented with Beyer earphone connected to speculum (placed in the meatus of the external ear canal) at a rate of 20 Hz. Stimulus was calibrated against a Bruel & Kjaer 4134 microphone connected to a Bruel & Kjaer 2203 sound level meter. A Grass P15 preamplifier and custom amplifier provided gain of $10^5$ and filtering of 0.3 to 3.0 kHz. Two responses were obtained at each intensity level. Thresholds were determined for the frequencies 2, 4, 8, 16 and 32 kHz from a set of responses at varying intensities with 5 dB intervals and 1000 sweeps near threshold.

After the treatment period of 21 days and measurement of ABRs, the animals were sacrificed and the temporal bones fixed by 4% PFA (paraformaldehyde) through perilymphatic perfusion. The left cochleas were dissected for surface specimens and the number of sensory hair cells in each auditory organ was evaluated by cytocochleograms. The upper halves of the cochleas were processed for cytocochleograms without embedding by staining cochlear whole mounts with rhodamine phalloidine (Molecular Probes, Eugene, Ore.) in PBS containing 0.25% Triton X-100 overnight at 4° C and mounted in Vectashield (Vector). Phalloidin is a specific marker for cellular F-actin. Basal halves of the cochleas were embedded in Epon and processed for cytocochleograms. Selected sections of Epon-embedded cochlear turns were processed for fine structural study by electron microscopy.

Results

Figure 1:
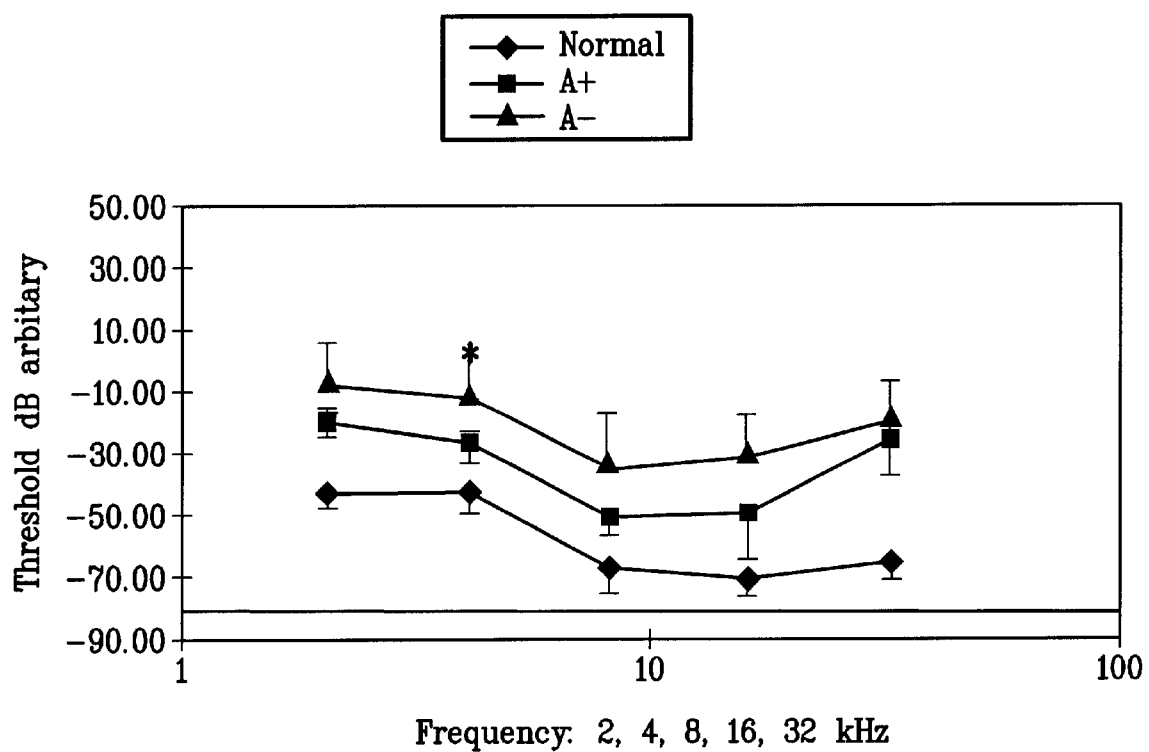
FIG. 1 depicts ABR (auditory brainstem response) measurements and demonstrates that the compound of Formula I prevents noise-induced sensory hair cell loss. ABR measurements were made at 2, 4, 8, 16 and 32 kHz prior to noise-induced lesion (filled diamond). Four animals were given the compound of Formula II (1 mg/kg, s.c.) followed by noise trauma 24 hours later. Animals were maintained for 21 days; treated animals were dosed once per day with the compound of Formula II at 1 mg/kg. ABR measurements were again taken at the end of 21 days. Lesion controls are shown as filled triangles; the compound of Formula II treated animals are shown as filled squares.

Noise exposure caused a hearing loss in all guinea pigs (four in each group) as measured by ABR (FIG. 1). At all frequencies except 32 kHz, the treated animals had an intermediate shift in their ABR measurement. The threshold shift was 40–60 dB SPL across the test frequencies in control (vehicle-treated, noise exposed) animals but only 20–40 dB in animals receiving the compound of Formula II.

Before noise lesioning, the total number of OHCs (or Deiters scars, the sites where OHCs had been located) was equivalent in control and treatment groups. The total number of OHCs ranged from about 6000 to 7000, averaging 6583+/−203 sensory hair cells in the control group and 6445+/−234 sensory hair cells in the treated group. In all noise-lesioned, control cochleas, the organ of Corti showed extensive degeneration of outer sensory hair cells throughout the cochlea, with 17–84% of the cells lost (Table 2). The most affected area was between 11 mm and 7 mm from the Round Window (RW) located in the middle turn and upper basal turn. Within this region, hair cells were absent over a distance of about 1.5–3.0 mm (FIG. 2b).

Figure 2A:
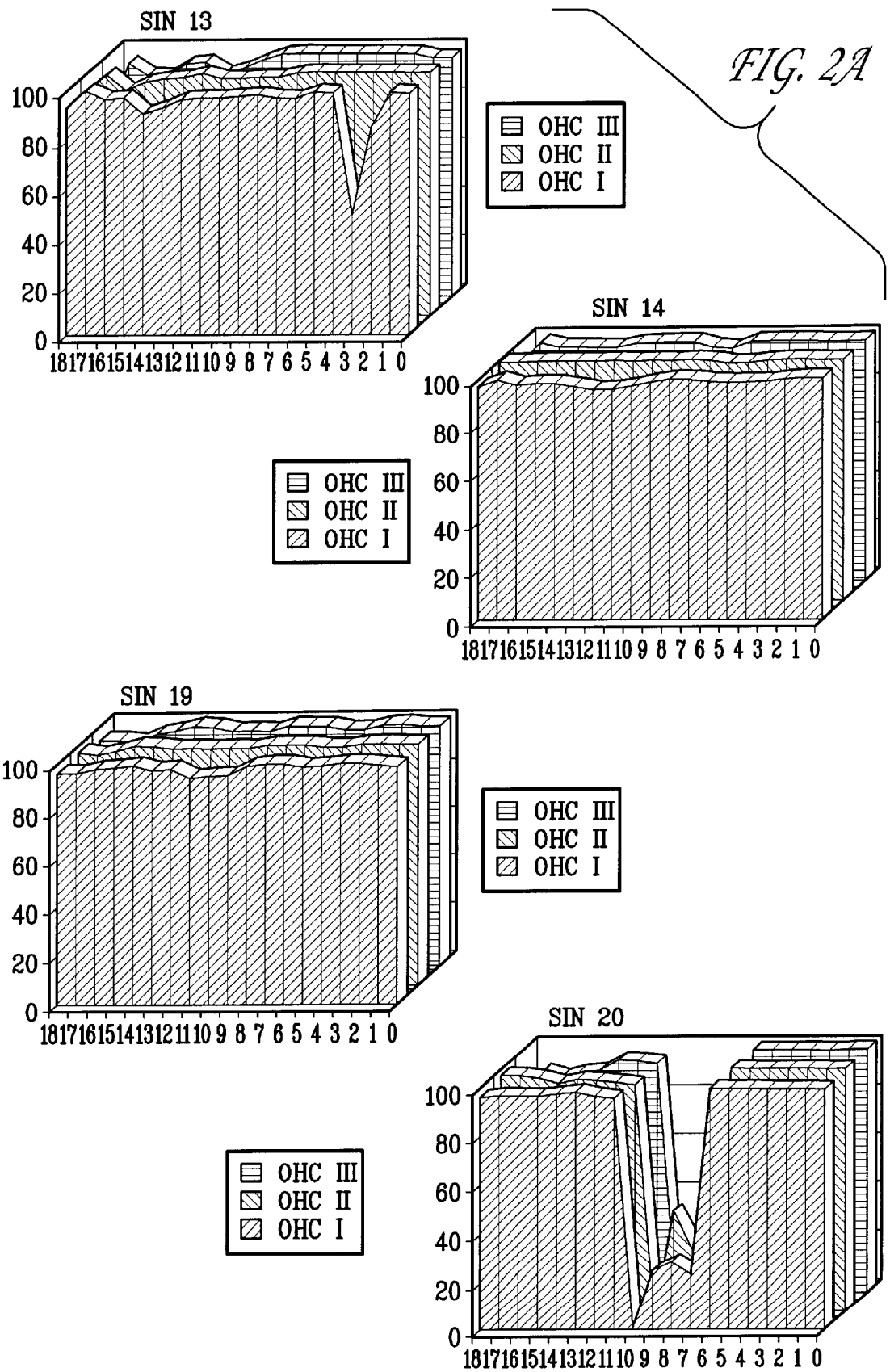

In contrast, three out of four compound of Formula II treated animals showed only a minor loss of sensory hair cells ranging from 1–3% (Table 2). The fourth animal had a loss of 19%. In the three animals with almost complete sensory hair cell preservation, the small percentage of cells lost did not appear to localize to a particular site in the organ of Corti (FIG. 2a). The light microscope morphology of the preserved sensory hair cells in the treated animals appeared normal and showed only minor changes by electron microscopy.

In this noise-trauma model, both the functional measure of the ABR and the actual cell counting suggest that the compound of Formula II was effective in preserving both the outer sensory hair cells themselves and their functional abilities.

TABLE 2

| Treatment | Animal ID# | Total OHC | LOST OUTER SENSORY CELLS (OHC) | | | | |
|---|---|---|---|---|---|---|---|
| | | | OCH1 | OCH2 | OCH3 | TOTAL OHC LOST | % OHC LOST |
| Formula II | 13 | 6036 | 90 | 25 | 71 | 186 | 3.1% |
| Formula II | 14 | 6477 | 19 | 3 | 27 | 49 | 0.8% |
| Formula II | 19 | 6990 | 36 | 18 | 46 | 100 | 1.4% |
| Formula II | 20 | 6276 | 356 | 381 | 428 | 1195 | 19.0% |
| MEAN | | 6445 | 133 | 107 | 143 | 383 | 6.1% |
| SD | | 234 | 99 | 106 | 110 | 314 | 5.0% |
| CONTROL | 15 | 6855 | 635 | 712 | 760 | 2107 | 30.7% |
| CONTROL | 17 | 6282 | 1554 | 1832 | 1863 | 5249 | 83.6% |
| CONTROL | 18 | 6612 | 351 | 341 | 411 | 1103 | 16.7% |
| MEAN | | 6583 | 547 | 962 | 1011 | 2820 | 43.7% |
| SD | | 203 | 445 | 549 | 536 | 1529 | 24.9% |

EXAMPLE 2

Prevention of Hearing Impairment/Apoptosis

Noise lesioning.

Adult Dunkin-Hartley female guinea pigs (weight 300–500 g) were exposed, 4 animals at a time, to octave band noise, with a center frequency of 4.0 kHz, 120 dB SPL for 6 hr as described in Example 1. Fragmented hair cell nuclei were assessed from noise-exposed cochleas immediately and 1, 2, 4, 6, 8 and 14 days after noise exposure. Noise-exposed and nonexposed guinea pigs were decapitated under deep anesthesia and inner ears were perilymphatically perfused with 4% paraformaldehyde in PBS, and processed for 5-mm-thick paraffin-embedded sections (Ylikoski et al., Hear Res 65:69–78, 1993; Ylikoski et al., Hear Res 124:17–26, 1998). TUNEL-staining was performed as described below. DNA fragmentation was also verified by DAPI nuclear counterstain (see below). Further, trauma-induced nuclear fragmentation was verified by morphological analysis of contralateral cochleas that were perilymphatically fixed with 2.5% glutaraldehyde in 0.1M phosphate buffer, pH 7.4, postfixed with 1% osmium tetroxide, embedded in epoxy resin, and prepared for surface preparations (see below). Selected cochlear segments were then cut in transverse and horizontal planes to semi-thin (1.0 mm) sections that were stained with 1% toluidine blue. Analysis was done under an Olympus Provis microscope equipped with Nomarski optics.

Test-substance delivery.

Formula II was injected subcutaneously to noise-exposed guinea pigs at the dose of 1 mg/kg, starting 2 hr before noise exposure and continuing daily for 2 weeks. Formula II was dissolved in 5% Solutol (BASF Corp., Parsippany, N.J.) in PBS, pH 7.4. The 1 mg/kg dose of the compound of Formula II was prepared daily from a 10 mg/ml stock in 25% Solutol that was stored at 4° C. Noise-exposed control guinea pigs received the vehicle alone.

Hearing tests.

Auditory brainstem responses (ABRs) were measured 2 days before noise exposure, and 2, 6 and 14 days after exposure under anesthesia (xylazine 10 mg/kg and ketamine 40 mg/kg). One ms hanning windowed binaural stimuli with 0.5 ms rise and fall of frequencies 2, 4, 6, 8, 16 and 32 kHz were presented at a rate of 10 Hz. Preamplifier and custom data acquisition provided a gain of 80000, with filtering of 0.3 to 10 kHz. Two responses summed from 1000 trials were obtained at each intensity level. Hearing threshold was determined from a set of responses at varying intensities. The threshold was defined as the last appearance of peak 3 or 4 in the ABR waveforms. Testing was performed in a sound attenuated box and animal temperature was kept at 37° C.

Cytocochleograms.

Two weeks after noise exposure, control and Formula II-treated guinea pigs were decapitated under deep anesthesia and inner ears were perilymphatically perfused with 2.5% glutaraldehyde in 0.1M phosphate buffer, pH 7.4, postfixed with 1% osmium tetroxide, embedded in epoxy resin and processed for surface preparations as earlier described in detail (Ylikoski, Acta Otolaryngol (Stockh) Suppl 326:5–20, 1974). Briefly, segments of the cochlear duct were dissected free from the modiolus, trimmed and re-embedded in resin. The re-embedded cochlear segments were studied as surface preparations under an Olympus Provis microscope equipped with Nomarski optics. Hair cells were characterized as missing if both no cuticular plate and stereocilia in the appropriate location was observed. For cell counting, a 10×10 square eye reticular and a 40×objective lens were used. The percentage of missing hair cells was plotted as a function of the percentage length of the organ of Corti.

Results

Hair cells die by apoptosis after noise trauma

Noise trauma induced maximal damage to hair cells of the organ of Corti at the 9 mm region from the round window (second cochlear turn. Noise-exposed (n=16) and nonexposed (n=3) cochleas were cut in transverse (midmodiolar) plane, and double stained with the DAPI counterstain (FIG. 3a) and with TUNEL-method (FIGS. 3b,c). In addition, resin-embedded organ of Corti's of noise-exposed cochleas (n=6) were cut in transverse (FIG. 3d) or horizontal plane (FIGS. 3e,f), and stained with toluidine blue. Most of the TUNEL-labeled cells were located in the area of maximal lesion, the second cochlear turn (FIG. 3e). During the study period, the first 2 weeks after noise exposure, TUNEL-labeling was not detected in the supporting cells of the organ of Corti (FIGS. 3a,b) or in the cochlear neurons. In nonexposed cochleas, cells of the organ of Corti as well as neurons were not TUNEL-labeled. Two weeks after noise exposure, no TUNEL-labeled sensory hair cells could be found in control or treated cochleas.

In control cochleas, the main part of hair cell apoptosis occurred during the first 6 days after noise exposure. The apoptotic profiles concentrated to the upper basal and lower middle coil, in accordance with the results of cytocochleograms showing that sensory hair cell loss was concentrated to this area (about 50% distance from the apex). The amount of apoptotic hair cell loss was less in Formula II-treated cochlea, these results being in agreement with the ABR-measurements showing a statistically significant difference in hearing function between the two group at this postexposure time point.

Formula II attenuates noise-induced hearing loss in vivo

Figure 4A:
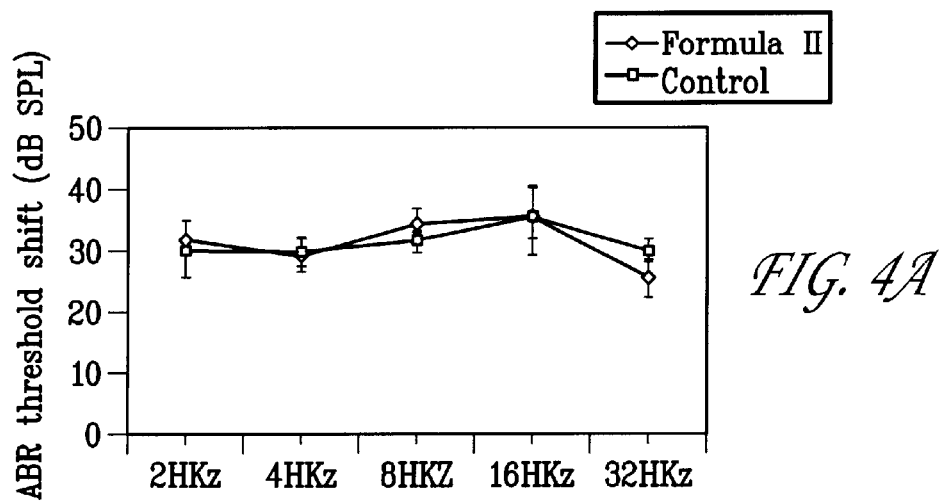
FIGS. 4a–c depict the protection against permanent hearing loss after treatment with the compound of compound of Formula II measured by ABR.
Figure 4B:
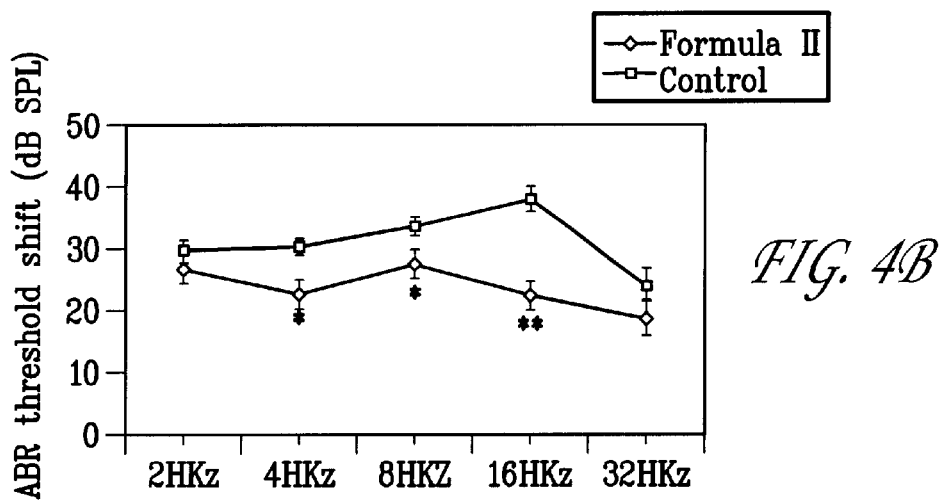
Figure 4C:
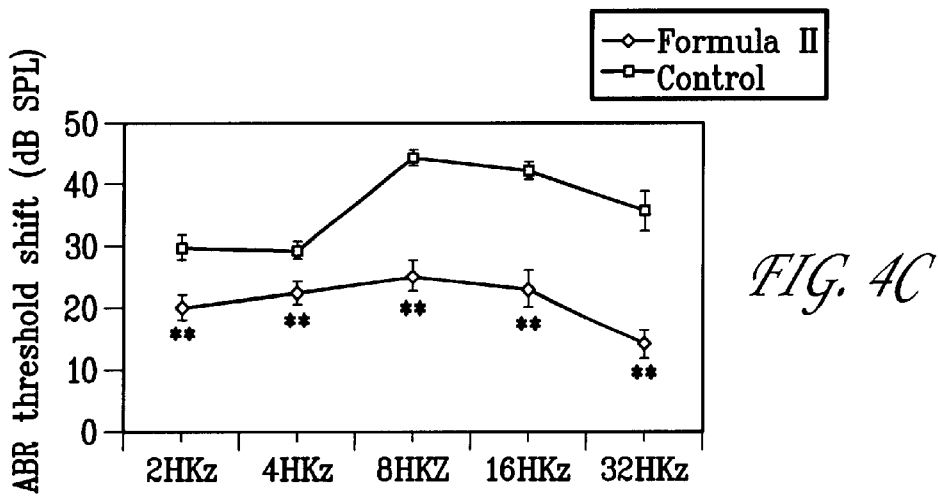

Hearing thresholds measured 2 days before noise exposure (baseline values) showed no significant difference between the noise-exposed control and treated group. Noise exposure caused threshold shifts in all guinea pigs as seen 2 days after the exposure (noise-exposed control n=4, Formula II-treated n=5) (FIG. 4a). By day 6 postexposure, threshold shifts were significantly less in the Formula II group (n=11) than in the noise-exposed control group (n=8, P<0.05 at 4 and 8 kHz, P<0.01 at 16 kHz) (FIG. 4b). By 2 weeks postexposure, the difference between the 2 groups became even more pronounced (noise-exposed control n=17, Formula II-treated n=17) (FIG. 4c). At this stage, ABR threshold shifts ranged from 28 to 45 dB SPL in noise-exposed controls, and from 12 to 22 dB SPL in Formula II-treated animals (P<0.01 at all frequencies).

Formula II attenuates noise-induced hair cell loss

Two weeks after noise exposure and after final ABR recordings had been performed, the numbers of preserved and missing hair cells were assessed in resin-embedded cochlear surface preparations. Total number of OHCs per guinea pig cochlea (lost plus preserved hair cells) ranged from 6240 to 6897 (Table 3). There was a large variation in the amount of hair cell damage in noise-exposed control cochleas in which the extent of lost hair cells ranged from 305 to 1266 (n=13). In Formula II treated cochleas, the number of missing hair cells ranged from 106 to 632 (n=13) (Table 3). This difference is statistically significant (P<0.01).

TABLE 3

| Sample I.D. | OHCs total | Lost IHC | hair OHC1 | cells OHC2 | ORC3 | ORC loss total (%) |
|---|---|---|---|---|---|---|
| Formula II-1 | 6897 | 1 | 40 | 27 | 38 | 105 (1.5) |
| Formula II-2 | 6672 | 7 | 72 | 62 | 63 | 197 (3.0) |
| Formula II-3 | 6699 | 24 | 20 | 38 | 47 | 105 (1.6) |
| Formula II-4 | 6573 | 28 | 42 | 67 | 74 | 183 (2.8) |
| Formula II-5 | 6585 | 19 | 53 | 37 | 64 | 154 (2.3) |
| Formula II-6 | 6666 | 17 | 41 | 50 | 54 | 145 (2.2) |
| Formula II-7 | 6846 | 14 | 61 | 53 | 76 | 190 (2.8) |
| Formula II-8 | 6723 | 17 | 64 | 66 | 80 | 210 (3.1) |
| Formula II-9 | 6795 | 24 | 57 | 60 | 93 | 210 (3.1) |
| Formula II-10 | 6748 | 9 | 38 | 45 | 58 | 141 (2.1) |
| Formula II-11 | 6387 | 6 | 74 | 74 | 56 | 204 (3.2) |
| Formula II-12 | 6240 | 2 | 59 | 69 | 161 | 289 (4.7) |
| Formula II-13 | 6454 | 25 | 180 | 198 | 229 | 607 (9.4) |
| Control-1 | 6621 | 7 | 96 | 156 | 255 | 507 (7.7) |
| Control-2 | 6421 | 33 | 77 | 109 | 178 | 364 (5.7) |
| Control-3 | 6480 | 77 | 89 | 136 | 141 | 366 (5.6) |
| Control-4 | 6690 | 56 | 118 | 119 | 225 | 462 (6.9) |
| Control-5 | 6687 | 23 | 95 | 92 | 95 | 282 (4.2) |
| Control-6 | 6630 | 43 | 125 | 111 | 139 | 375 (5.7) |
| Control-7 | 6897 | 56 | 102 | 139 | 184 | 425 (6.2) |
| Control-8 | 6882 | 78 | 156 | 222 | 341 | 719 (10.4) |
| Control-9 | 6507 | 77 | 205 | 117 | 184 | 506 (7.8) |

TABLE 3-continued

| Sample I.D. | OHCs total | Lost IHC | hair OHC1 | cells OHC2 | ORC3 | ORC loss total (%) |
|---|---|---|---|---|---|---|
| Control-10 | 6690 | 117 | 222 | 413 | 514 | 1149 (17.2) |
| Control-11 | 6621 | 7 | 96 | 156 | 255 | 507 (7.7) |
| Control-12 | 6423 | 2 | 65 | 149 | 114 | 328 (5.1) |
| Control-13 | 6849 | 11 | 161 | 209 | 281 | 648 (7.6) |

In vehicle-treated, noise-exposed control cochleas, in addition to missing hair cells, there were several distorted OHCs with irregular configuration and disarrayed stereocilia, but a preserved cuticular plate and nucleus in regions adjacent to the site of maximal damage. Most of the noise-exposed control cochleas showed a relatively well demarcated area of maximal damage, extending over 0.5 to 1.0 mm in the region of about 9 mm from the round window. In addition, scattered OHC loss was found particularly along the entire upper half of the cochlea. Formula II treated cochleas showed some destruction of the organ of Corti, but usually in an area extending over 0.1–0.2 mm only. Also scattered OHC loss was less than in noise-exposed control cochleas. The cytocochleograms (FIGS. 5a,b) illustrate the average percentages of missing IHCs and OHCs along the length of the organ of Corti in noise-exposed control (n=13) and Formula II treated (n=13) cochleas. These results indicate that, in our intense noise paradigm, Formula II rescues IHCs as well as OHCs of each of the 3 rows.

EXAMPLE 3

Protective Effect of the Compound of Formula II Against Neomycin in Neonatal Rat Cochlear Explants The compound of Formula II attenuated neomycin-induced cochlear sensory hair cell loss in vitro. The effect of the compound of Formula II on neomycin-induced hair cell degeneration was determined in organotypic cultures of the neonatal organ of Corti.

Cochlear cultures.

The basal half of cochleas containing the basal and middle turns were dissected from postnatal day 2 Wistar rats. The cultures were maintained on Nuclepore filters (pore size 0.1 mm; Pleasanton, Calif.) placed on a metal grid in F12 medium (Life Technologies, Gaithersburg, Md.) containing 15% fetal bovine serum (Life Technologies). After a 2-hour-long stabilization period, explants were exposed to 100 mM neomycin sulfate (Sigma, St Louis, Mo.) for 48 hr. Formula II (500 nM) was added at the time of initiation of the cultures and every 12 hr thereafter.

Hair cell counts in cochlear cultures.

Explants were fixed with 4% paraformaldehyde/0.5% glutaraldehyde in phosphate buffered saline (PBS), pH 7.4, for 30 min and dissected for surface preparations. They were stained with a 1:100 dilution of rhodamine-phalloidin in PBS containing 0.25% Triton X-1 00 overnight at 4° C. and mounted in Vectashield (Vector). Outer hair cell (OHC) numbers were quantified with a Zeiss Axiovert 100/135 epifluorescent microscope (Germany) connected to a Bio-Rad MRC-1024 confocal laser scanning system (Richmond, Calif.). Hair cells were characterized as missing if no stereocilia and cuticular plate were observed. Numbers of OHCs were evaluated using a 40×objective lens and an ocular grid. Nine to 1 fields filled by 30 OHCs in each of the 3 rows (when all of them were present) were studied from each explant. Basal and middle coils were analyzed separately. Three separate experiments, each including 4 explants of both conditions (neomycin and neomycin plus Formula II) were analyzed.

Results

Figures 6A, 6B:
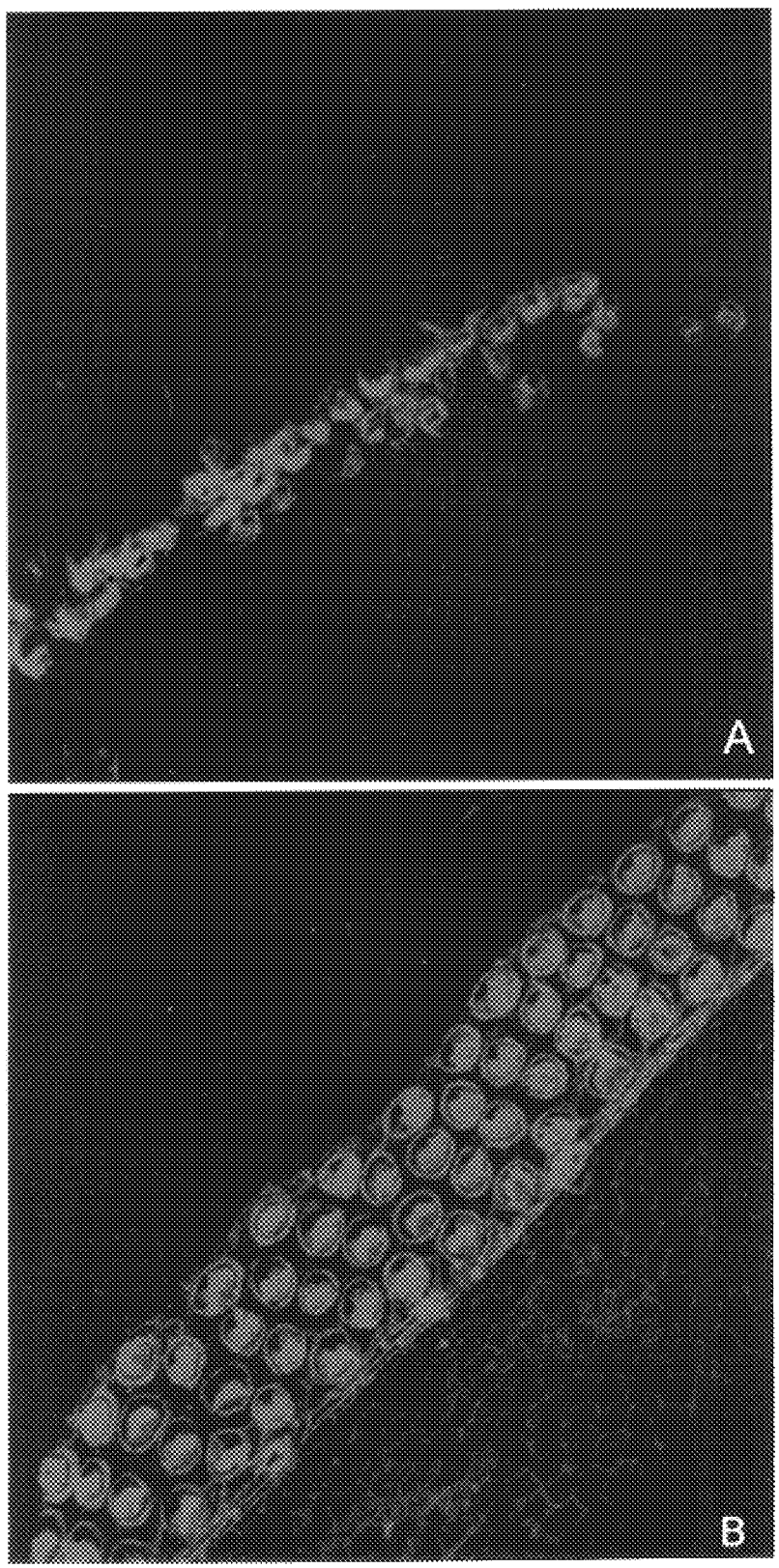
FIGS. 6a and 6b depict the preservation of sensory hair cells following neomycin treatment due to treatment with the compound of Formula II. Organ of Corti explants of neonatal rats were dissected for surface preparations, treated with 100 $\mu$M neomycin alone or in conjunction with the compound of Formula II (500 nM) for 48 hours, stained with phalloidin, and imaged by laser confocal microscope (FIG. 6a). Neomycin causes degeneration of a large number of hair cells (FIG. 6b). The compound of Formula II protects hair cells from neomycin induced cell death.

When the cultures were treated with 100 $\mu$M neomycin, many sensory hair cells were lost within 48 hours, especially in the basal half of the cochlea. 100 $\mu$M neomycin caused the loss of most basally located sensory hair cells, as detected in surface preparations of the cultures using F-actin (phalloidin) as a sensory hair cell marker (FIG. 6a). These results are in accordance with earlier data showing that sensory hair cells situated in the basal part of the cochlea are more sensitive to antibiotics than the apically located ones. When 500 nM of the compound of Formula II was added to the cultures together with neomycin, sensory hair cell degeneration was reduced (FIG. 6b).

Figure 7C:
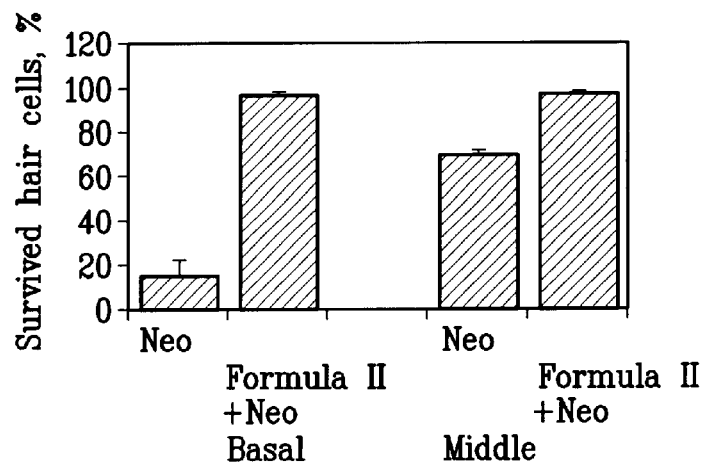

In explants exposed to 100 mM neomycin for 48 hr (n=12), severe hair cell degeneration occurred in the basal turn of the cochlea (FIG. 7a), as shown in phalloidin-labeled confocal images. Formula II prevented hair cell loss in the basal turn of the cochlea (FIG. 7b). Approximately 90% of OHCs in the basal turn and 25% of OHCs in the middle turn were lost (FIG. 7c). In cultures co-incubated with 500 nM Formula II and neomycin for 48 hr (n=12), about 90% of OHCs in the basal turn were preserved.

EXAMPLE 4

Protective Effect of the Compound of Formula II Against Gentamicin Toxicity in Cochlear and Vestibular Hair Cells Animals, tissues, lesioning and test drug delivery.

Adult Dunkin-Hartley female guinea pigs (weight 300–400 g) were used. They were given free access to water and a regular guinea pig diet. The animals were given 1 week of adjustment before baseline ABR recordings and gentamicin (GM) treatment.

Two experimental groups were formed. Group 1 guinea pigs served as control and were treated with gentamicin only. The animals were injected s.c. with gentamicin at 120 mg/kg body weight, once daily for 14 days. Three guinea pigs (yielding a total of 6 inner ears) were included in this group. The animals were decapitated 30 days after the start of the injections.

Group 2 guinea pigs were treated with gentamicin plus Formula II. The animals were injected s.c. with GM at 120 mg/kg body weight, plus Formula II at 1 mg/kg, once daily for 14 days. Formula II treatment started 1 day before GM injections. Formula II treatment was continued for 28 or 29 days. Four guinea pigs (8 inner ears) were included in this group. The animals were decapitated 30 days after the start of GM injections.

In addition to the animals of groups 1 and 2, two guinea pigs that received only GM and two guinea pigs that received GM plus Formula II were decapitated at day 14. These inner ears were used for the documentation of apoptosis. A large number of apoptotic vestibular and cochlear hair cells were found in only GM-treated inner ears (TUNEL-staining) .

Evaluation of auditory function.

ABRs were determined 1 day before GM injections (baseline values) and at day 30 after the start of the GM injections. Threshold shift shows the difference between the baseline and the final threshold. Thresholds were determined at frequencies 2, 4, 8, 16 and 32 kHz from a set of responses at varying intensities with 5 dB intervals and 1000 sweeps near the threshold. ABRs were measured with System II hardware and BioSig software. Ketamine (40 mg/kg) and xylazine (10 mg/kg) were used for anaesthesia.

Processing of the inner ears for morphometric analyses.

Guinea pigs were decapitated under deep anaesthesia and the inner ears were perilymphatically fixed and immersed with 2.5% glutaraldehyde in 0.1 M phosphate buffer (pH 7.4), postfixed with 1% osmium tetroxide, and embedded in Epon. Cochleas were processed for cytocochleograms (Ylikoski, Acta Otolaryngol (Stockh) Suppl 326:5–20, 1975). The separately dissected and Epon-embedded vestibular organs were cut for 1 μm-thick sections. Every 25th section was collected onto slides and stained with 1% toluidine blue. The quantity of hair cell loss in vestibular organs was evaluated by counting hair cells in at least 10 corresponding transverse sections of the horizontal or superior ampullary cristae. Two control (GM-treated) and 3 Formula II plus GM-treated ampullae were used for analysis. The presence of cell nuclei in the sensory layer (upper half) of the sensory epithelium was regarded as the presence of hair cells. Supporting cell nuclei were clearly distinguished from hair cells by their position (lower part) in the epithelium and by toluidine blue that stains the hair cells weaker than the supporting cells. Hair cell loss was measured by comparing the number of hair cell nuclei in the sensory layer to the number of hair cell nuclei in the basal cell layer.

Results

Formula II attenuates gentamicin-induced hearing loss.

Compared to control cochleas (GM only, n=6), Formula II treated cochleas (n=8) showed less threshold shift at all frequencies tested. The difference was statistically significant at all frequencies tested (P<0.01). The average threshold shifts are shown in FIG. 8.

Formula II attenuates hair cell loss in the vestibular end organs after gentamicin intoxication.

Compared to control (GM only) ampullae (n=2), Formula II treated ampullae (n=3) showed less hair cell loss, as revealed by the analysis of relative hair cell loss (Table 4). The protective effect of Formula II in the ampullae was 70%.

TABLE 4

Relative numbers of preserved hair cells in GM and GM + Formula II treated cochleas

| Sample | Number of sections | Relative length of sensory epithelium (frames) | Total number of hair cells | Hair cells per frame |
|---|---|---|---|---|
| Control | 11 | 169 | 199 | 1,2 |
| Control | 16 | 245 | 270 | 1,1 |
| Formula II | 17 | 276 | 518 | 1,9 |
| Formula II | 10 | 174 | 328 | 1,9 |
| Formula II | 23 | 287 | 620 | 2,2 |

EXAMPLE 5

Protective Effect of the Compound of Formula II Against Death of Cochlear Neurons in Vitro Dissociated neuronal cultures.

Neuronal enriched cultures from embryonic day 21 (E21) rat cochlear ganglia were prepared as previously described (Ylikoski et al., Hear. Res., 1998, 124:17–26). The cultures were maintained in F14 medium (Life Technologies, Gaithesburg, Md.) containing 10% horse serum (Life Technologies). Formula II (500 nM), neurotrophin-3 (NT-3; 2 ng/ml, Promega, Madison, Wisc.) or nerve growth factor (NGF; 2 ng/ml, Promega) was added at the beginning and after each 12 hr to the medium. After 48 hr, cultures were fixed with 4% paraformaldehyde and responses were assessed under a phase contrast microscope. Surviving neurons were distinguished by a phase-bright cell body and definite neurites.

Results

Formula II attenuated the death of cochlear neurons in vitro. NT-3 is the most potent neurotrophic factor promoting survival of dissociated cochlear neurons of the perinatal rat, and NGF does not have any effect or its effect is very weak (Ylikoski et al., 1998). As assessed in parallel cultures, Formula II was as efficacious as NT-3 in promoting survival of cochlear neurons. NGF served as a negative control (FIG. 9).

EXAMPLE 6

Delayed Administration of Formula II After Noise Trauma

Guinea pigs were exposed to 120 dB, 4 kHz noise for 6 hr. The compound of Formula II was administered beginning 2 hours to 1 day prior to noise trauma, or 1 day after noise trauma, or 4 days after noise trauma. Dosing continued for 2 weeks after noise exposure. As described above, cochleas were prepared and numbers of preserved and lost inner hair cells (IHCs) and outer hair cells of different rows (OHC1, OHC2, OHC3) were counted 2 weeks post noise trauma.

Evaluation of auditory function.

ABRs were determined 1 day before noise trauma (baseline values) and 2 weeks post noise trauma. Threshold shift shows the difference between the baseline and the final threshold. Thresholds were determined at frequencies 2, 4, 8, 16 and 32 kHz from a set of responses at varying intensities with 5 dB intervals and 1000 sweeps near the threshold. ABRs were measured with System II hardware and BioSig software. Ketamine (40 mg/kg) and xylazine (10 mg/kg) were used for anaesthesia.

Results

Formula II-treated animals showed less threshold shift at all frequencies tested than did vehicle-treated, noise-exposed controls. The average threshold shift of control animals is 20–40 dB greater than that of animals treated with Formula II beginning prior to the lesion. These data are presented in FIG. 10 and also, separately, as FIG. 4c. Decreased threshold shifts are also noted if administration of CEP-1347 is begun 1 or 4 days after exposure to noise. These data are presented in FIG. 10.

Compared to control cochleas, Formula II-treated cochleas showed less loss of hair cells following exposure to noise. The effect of delayed dosing of Formula II on hair cell loss is shown in FIG. 11; the top and bottom graphs were presented separately as FIG. 5. A statistical difference existed in hair cell loss between the 1 day delayed group (n=6) and noise-treated control group (n=13) P<0.01. A statistical difference existed between the 4 day delayed group (n=1 1) and noise-treated control group (n=13); P<0.05. Results are set forth in Table 5.

TABLE 5

| Sample | OHCs total | Lost IHC | hair OHC1 | cells OHC2 | OHC3 | OHC loss total (%) |
|---|---|---|---|---|---|---|
| 1 day delayed | 6900 | 0 | 35 | 46 | 58 | 139 (2.0) |
| 1 day delayed | 6528 | 54 | 129 | 116 | 106 | 351 (5.4) |
| 1 day delayed | 6708 | 1 | 44 | 33 | 8247 | 159 (2.4) |
| 1 day delayed | 6744 | 32 | 115 | 117 | 200 | 432 (6.4) |
| 1 day delayed | 6864 | 46 | 82 | 105 | 67 | 254 (3.7) |
| 1 day delayed | 6864 | 0 | 30 | 13 | 42 | 85 (1.2) |
| 4 days delayed | 6843 | 34 | 259 | 300 | 327 | 886 (12.9) |
| 4 days delayed | 6312 | 56 | 177 | 247 | 205 | 629 (10.0) |
| 4 days delayed | 6606 | 0 | 30 | 22 | 60 | 112 (1.8) |
| 4 days delayed | 6732 | 54 | 173 | 167 | 272 | 612 (9.1) |
| 4 days delayed | 6531 | 36 | 73 | 105 | 141 | 319 (4.9) |
| 4 days delayed | 6792 | 3 | 72 | 15 | 25 | 112 (1.6) |
| 4 days delayed | 6225 | 2 | 62 | 45 | 36 | 143 (2.3) |
| 4 days delayed | 6936 | 44 | 124 | 111 | 117 | 352 (5.2) |
| 4 days delayed | 6777 | 7 | 287 | 172 | 283 | 742 (10.9) |
| 4 days delayed | 6555 | 54 | 175 | 170 | 245 | 590 (9.0) |
| 4 days delayed | 6441 | 10 | 120 | 97 | 225 | 442 (6.9) |

Compared to control cochleas, Formula 11-treated cochleas showed less threshold shift at all frequencies tested than did control. The average threshold shifts are shown in FIG. 10. The most significant difference from control was exhibited by the group of animals which were administered Formula II before noise trauma. Both 1 day and 4 day delayed adminsitration of Formula exhibited less threshold shift than did the control group. Compared to control cochleas, Formula II-treated cochleas showed less hair cell loss. The effect of delayed dosing of Formula II on hair cell loss is shown in FIG. 11.

EXAMPLE 7

Assessment of Hair Cell Death and Immunohistochemistry in Cochlear Cultures

Six, 12 and 24 hr after adding 100 $\mu$M neomycin to the medium, cochlear cultures were fixed with 4% paraformaldehyde in PBS for 30 min. The specimens were prepared for 5 um-thick paraffin sections. They were stained with a TUNEL-kit, mounted in Vectashield containing DAPI nuclear counterstain (Vector, Burlingame, Calif.), and viewed under an Olympus Provis microscope (Tokyo, Japan) using epifluorescence. In addition to TUNEL-staining, DNA fragmentation was verified under UV illumination using DAPI counterstain.

Adjacent sections were immunostained with a polyclonal phospho-c-Jun antibody (Ser73, 1:500; New England Biolabs, Beverly, Mass.) and a polyclonal phospho-JNK antibody (Thr183/Tyr185, 1:250 dilution; New England Biolabs). The phospho-JNK antibody detects the dually phosphorylated isoforms of JNK 1, 2 and 3. The specificity of the phospho-specific antibodies was verified by Western blotting using sorbitol-treated PC 12 cells. Phospho-JNK antibody recognized the phosphorylated p54/p46 JNK and phospho-c-Jun antibody the phosphorylated p46 c-Jun in sorbitol-treated, but not in untreated PC 12 cells. For immunohistochemical detection, the avidin-biotin-peroxidase method (Elite ABC Kit; Vector) and diaminobenzidine were used. Stainings were amplified using tyramide signal amplification (TSA-Indirect Kit, NEN Life Science Products, Boston, Mass.) according to Brady et al. (1999), J. Neurosci., 19:2131–2142). No counterstaining was used in conjuction with the phospho-specific antibodies. In addition, a polyclonal calbindin antibody (1:10000 dilution; Swant, Switzerland) was used as a marker for hair cells. Calbindin immunoreaction was detected using the ABC method and diaminobenzidine without tyramide signal amplification, and the sections were lightly counterstained with 1% toluidine blue. Analysis was done under Olympus Provis microscope and bright-field optics.

Results

Formula II is effective in blocking JNK activation in stressed hair cells

Hair cell death and involvement of the JNK signaling cascade in organotypic cochlear explants of neonatal rats was examined. In paraffin sections of normal (nontreated) explants, the normal cellular architecture of the organ of Corti, one row of IHCs and 3 rows of OHCs could be seen using a calbindin-antibody that labels hair cells (FIG. 12a). Cellular death was studied in paraffin sections stained by the TUNEL-method that labels fragmented DNA. Further, when TUNEL-positive cells were found, DNA fragmentation was verified by using the DAPI counterstain. TUNEL-labeled hair cells were not found in normal explants (n=5). In contrast, in explants (n=15) exposed to 100 $\mu$M neomycin for 6, 12, 24 and 48 hr, TUNEL-positive hair cells were found, most of them at the first 2 time points studied (FIG. 12b,c). The majority of labeled hair cells were located in the basal cochlear turn where hair cells are most sensitive to ototoxic antibiotics. TUNEL-positive hair cell nuclei were found within the epithelium (FIG. 12b,c), and, in addition, hair cells that had been extruded from the epithelium in the cultures showed nuclear fragmentation.

In cochlear explants (n=10) exposed to 100 $\mu$M neomycin for 6 and 12 hr, phospho-JNK (FIG. 12d) and phospho-c-Jun (FIG. 12e) immunoreactive hair cells were found in the lesioned regions, in the basal and upper middle cochlear turns. Only the nuclei of hair cells were stained by these phospho-specific antibodies. Hair cells situated in the apical, nonlesioned areas did not show phospho-JNK or phospho-c-Jun immunolabeling, suggesting that the JNK pathway is involved in hair-cell stress responses. Formula II has been shown to attenuate neuronal apoptosis by blocking activation of JNK (Maroney et al., 1998). When cochlear explants (n=5) were coincubated with 500 nM Formula II and neomycin, both TUNEL-labeling and induction of JNK and c-Jun phosphorylation (FIG. 12b,c) were prevented in hair cells. These data indicate that Formula II is effective in blocking JNK activation in stressed hair cells.

EXAMPLE 8

Preparation of 6H,12H,13H-Indeno[2,3-a]pyrrolo[3,4-c]carbazole-5,7(5H, 7H)-dione Step A: Preparation of 2-(2(2-Hydroxy)indanyl)indole n-BuLi (107.5 mmol, 43 mL of 2.5M solution in hexanes) was added dropwise (15 min) to a solution (12.0 g, 102.4 mmol) of indole in dry THF (400 $\mu$L) at −78° C. (nitrogen atmosphere). The solution was stirred for 30 min, then $CO_2$ (g) was passed through the solution for 10 min. The clear solution was allowed to warm to ambient temperature, then it was concentrated to half the original volume at reduced pressure. THF (200 mL) was added and the solution re-cooled to −78° C. At this point, t-BuLi (102 mmol, 60 mL of 1.7M solution in hexanes) was added dropwise (45 min). The resulting yellow solution was allowed to stir for 2 h at −78° C. Next, 2-Indanone (15.0 g, 112.6 mmol) in THF (100 mL) was added dropwise (30 min) and the mixture stirred for 1 hour. The reaction was quenched by addition of water (5 mL); the resulting mixture was poured into saturated $NH_4Cl$ solution (250 mL), and then extracted with ether (1×mL). The ether layer was washed with 100 mL saturated $NH_4Cl$, dried ($MgSO_4$), and concentrated at reduced pressure to give an oily product. The product (V) was recrystallized from $Et_2O$-hexane to give 10.5 g of a tan powder with a m.p. of 244°–245° C. The following NMR data were obtained: $^1H$ NMR ($CDCl_3$): δ2.4 (bs, 1H), 3.3 (d, 2H), 3.6 (d, 2H), 6.4 (s, 1H), 7.1–7.4 (m, 7H), 7.6 (d, 1H), 8.6 (bs, 1H). Anal. calc. $C_{17}H_{15}NO$; C, 81.90; H, 6.06; N, 5.62. Found C, 82.16; H, 6.03; N, 5.58.

The mother liquor was concentrated to yield an oily product. Column chromatography (silica gel, EtOAc:hexane 1.2) yielded an additional 2.1 g of product for a total yield of 12.6 g (49%).

Step B: Preparation of 2-(2-Indenyl)indole

To a stirred solution of 2-(2-(2-hydroxy)indanyl)indole (4.0 g, 16.1 mmol) in acetone (30 mL) was added 2N HCl (10 mL). The mixture was stirred at ambient temperature for 1 hour. About 20 mL of water were added and the precipitate collected by filtration. The filtrate was washed well with water and dried to give 3.6 g (98%) of a white solid product with a m.p. of 273°–274° C. (MeOH). The following NMR data were obtained: $^1H$ NMR ($CDCl_3$): 63.9 (s, 2H), 6.7 (s, 1H), 7.0–7.6 (m, 9H), 8.3 (bs, 1H). Anal.calc. $C_{17}H_{13}N$, C, 88.28; H, 5.67; N, 6.06. Found C, 88.11; H, 5.60; N, 5.98.

Step C: Preparation of 4c,7a,7b,12a-Tetrahydro-6H, 1 2H 1 3H-indeno[2,3-a]pyrrolo [3,4-c]carbazole-5,7-(5H, 7H)dione A mixture of 2-(2-indenyl)indole (1.0 g, 4.3 mmol) and maleimide (525 mg, 5.41 mmol) in a 10 cm sealed reaction vial was heated at 180°–190° C. for 30 min. After cooling the reaction to ambient temperature, MeOH (5 mL) was added. The product was collected to give 880 mg (62%) of a white solid product with a m.p. of 254°–255° C. (MeOH). The following NMR data were obtained: $^1H$ NMR (DMSO-$d_6$, 300 MHz): 63.1–3.4 (m, 2H), 3.8 (m, 2H), 3.95 (t, 1H), 4.35 (d, 1H), 6.9–7.4 (m, 7H), 7.75 (d, 1H), 11.05 (s, 1H), 11.25 (s, 1H).

Step D: Preparation of 6H,12H,13H-Indeno[2,3-a]pyrrolo[3,4-c]carbazole-5,7(5H, 7H)-dione 4c,7a,7b, 1 2a-Tetrahydro-6H, 12H, I 3H-indeno[2,3-a]pyrrolo [3,4-c]carbazole-5,7-(5H, 7H)dione (800 mg, 2.44 mmol) was dissolved in toluene (60 mL). Solid 2,3-dichloro-5,6-dicyano-1,4-benzoquinone (1.4 g, 6.1 mmol) was added to the toluene solution in one portion.

The solution was maintained at 60°–65° C. for 6 hours. After cooling on an ice bath, the solid product was collected by filtration, resuspended in MeOH (20 mL) and collected by filtration.

The product was recrystallized from acetone-MeOH to yield 710 mg (90%) of a yellow solid product with a m.p. greater than 330° C. The following NMR data were obtained: $^1H$ NMR (DMSO-$d_6$, 300 MHz): δ4.3 (s, 2H), 7.35 (t, 1H), 7.45–7.65 (m, 4H), 7.75 (d, 1H), 8.95 (d, 1H), 9.1 (d, 1H), 11.15 (s, 1H), 12.3 (s, 1H). MS(FAB): m/e 325 (m+1)$^+$. Anal. calc. for $C_{21}H_{12}N_2O_2$. 0.75 $H_2O$: C, 74.65; H, 4.03; N, 8.29. Found; C, 74.40; H, 3.75; N, 8.26.

EXAMPLE 9

Preparation of 13-(2-Hydroxyethyl):5H;6H,12H, 13H-indeno[2,3-a]pyrrolo [3,4-c] carbazole-7(7H) one Step A: Preparation of 5H,6H,12H,13 H-Indeno[2,3-a]pyrrolo[3,4-c]carbazole-7(7H)one A stirred suspension of Zn dust (5 g) and mercuric chloride (1 g) was made in 10 mL water. Concentrated hydrochloric acid (2 mL) was added dropwise. After 10 min, the aqueous layer was decanted and removed. The zinc amalgam obtained was first washed with water, then repeatedly with EtOH. The zinc amalgam was suspended in EtOH (75 mL). Next, solid 6H,12H,13H-Indeno[2,3-a]pyrrolo[3,4-c]carbazole-5,7(5H,7H)-dione (500 mg, 1.5 mmol) was added in one portion. HCl(g) was passed through as the mixture was maintained at reflux for 2 hours. After cooling to ambient temperature, the solution was concentrated at reduced pressure to yield an oily product. THF-EtOAc (200 mL, 1:1) was added to the oily product and the mixture was extracted with a saturated $NaHCO_3$ solution (3×100 mL), saturated NaCl solution (3×100 mL) and the resulting solution dried ($MgSO_4$). The drying agent was removed, and the solvent was concentrated at reduced pressure to give a crude solid. Purification by column chromatography (silica gel, 95:5, EtOAc:MeOH) yielded 240 mg (50%) of a 1:4 mixture of 5H,6H,12H,13H-indeno[2,3 -a]pyrrolo[3,4-c]carbazole-7(7H)one and 6H,7H,12H,13H-indeno[2,3-a]pyrrolo[3,4-c]carbazole-5(5H)one. The following NMR data were obtained: $^1H$ NMR (DMSO-$d_6$, 300 MHz): 64.15 (s, 1.6H), 4.25 (s, 0.4H), 4.9 (s, 0.4H), 4.95 (s, 1.6H), 7.2–7.8 (m, 6H), 8.0 (d, 1H), 8.6 (s, 0.8H), 8.8 (s, 0.2H), 9.2 (d, 0.2H), 9.4 (d, 0.8H), 11.8 (s, 0.2H), 11.95 (s, 0.8H). MS(m/e 311 (m+l )$^+$.

Step B: Preparation of 13-(2-Hydroxyethyl):5H;6H, 12H.1 3H-indeno[2,3-a]pyrrolo[3,4-c]carbazole-7(7H) one 5H,6H,12H,13H-indeno[2,3-a]pyrrolo[3,4-c]carbazole-7(7H)one (200 mg, 0.65 mmol) was added to a stirred solution of NaH (25 mg of 60% oil dispersion, 0.65 mmol) in dry DMF (10 mL) under a nitrogen atmosphere. The dark mixture was stirred at ambient temperature for 1 hour. Ethyl bromoacetate (120 mg, 0.08 mL, 0.72) was added dropwise and the mixture was stirred 12 hours. The resulting yellow solution was concentrated at reduced pressure to give a crude yellow solid. The product was dissolved in dry THF (10 mL) and lithium aluminium hydride (1 mL of 1M solution in ether) was added dropwise. The solution was stirred 6 hours at room temperature, then the reaction was quenched by the addition of $H_2O$ (1 mL). The mixture was filtered and concentrated at reduced pressure. THF was added to the residue and the product was collected to give 30 mg(17%) of 13-(2-Hydroxyethyl):5H;6H, 12H, 13H-indeno[2,3-a]pyrrolo[3,4-c]carbazole-7(7H)one as a white solid. The melting point was greater than 300° C. The following NMR data were obtained: $^1H$ NMR (DMSO-$d_6$, 300 MHz): δ3.8–3.9 (b, 2H), 4.55 (s, 2H), 4.77 (t, 2H), 4.9 (s, 2H), 5.0 (1H, $D_2O$ exchange), 7.3–7.45 (m, 3H), 7.5–7.57 (t, 1H), 7.67 (d, 1H, J=6 Hz), 7.5 (d, 1H, J=6 Hz), 8.0 (d, 1H, J=6 Hz); 8.57 (s, 1H), 9.5 (d, 1H, J=7 Hz). MS(FAB): m/e 355 (M+1)$^+$.

EXAMPLE 10

Preparation of 6H,12-Benzo[b]thieno[2,3-pyrrolo[3, 4-c]carbazole-5,7(5H, 7H)dione A solution of 2-(2-benzo[b]thienyl)indole, maleimide (120 mg, 1.2 mmol) and trifluoroacetic acid (1 mL) in dry toluene (75 mL) was stirred at reflux for 12 hours. The solution was cooled to ambient temperature and concentrated at reduced pressure to yield a crude solid. The solid was dissolved in glacial HOAc (40 mL), 5% Pd(OAc)$_2$ was added and the mixture maintained at reflux for 12 hours. The solution was cooled to ambient temperature, filtered through Celite™, then concentrated at reduced pressure. MeOH was added to the residue and the product collected (80 mg, 23%). The product was further purified by column chromatography (EtOAc:Hexane 2:1 R$_f$=0.5) to give 6H,12-Benzo[b]thieno[2,3-pyrrolo[3,4-c]carbazole-5,7(5H, 7H)dione. The melting point was greater than 300° C. The following NMR data were obtained: $^1$H NMR (DMSO-d$_6$, 300 MHz) δ7.4 (t, 1H), 7.55–7.75 (m, 4H), 8.25 (m, 1H), 9.05 (d, 1H), 9.8 (m, 1H), 11.4 (s, 1H), 12.8 (s, 1H). MS(FAB): m/e=343 (M+1)$^+$. Anal. calc. for: C$_{20}$H$_{10}$N$_2$OS. 0.5 H$_2$O; C, 67.49; H, 3.26; N, 7.87. Found: C, 67.50; H, 3.07; N, 7.51.

EXAMPLE 11

Preparation of the Following Fused Pyrrolocarbazole

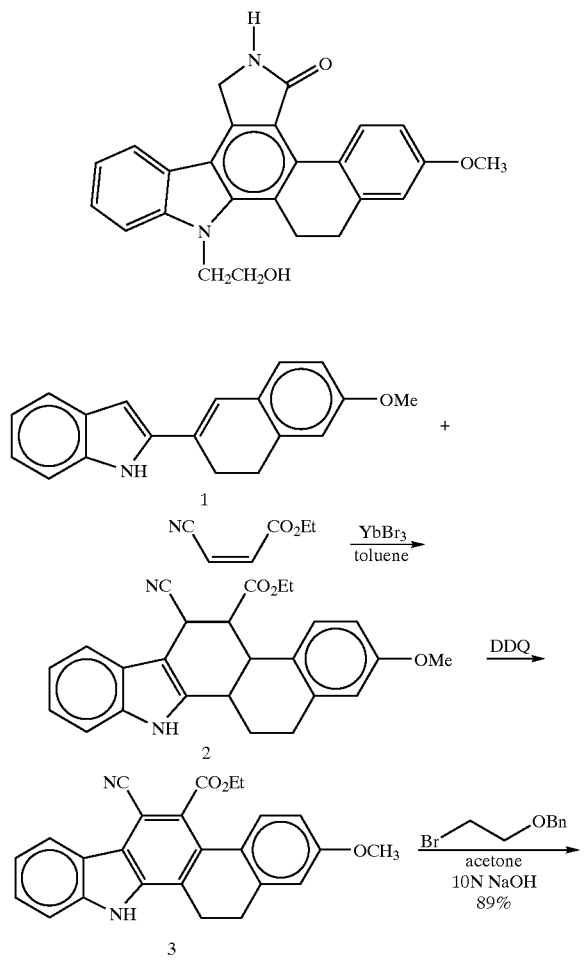

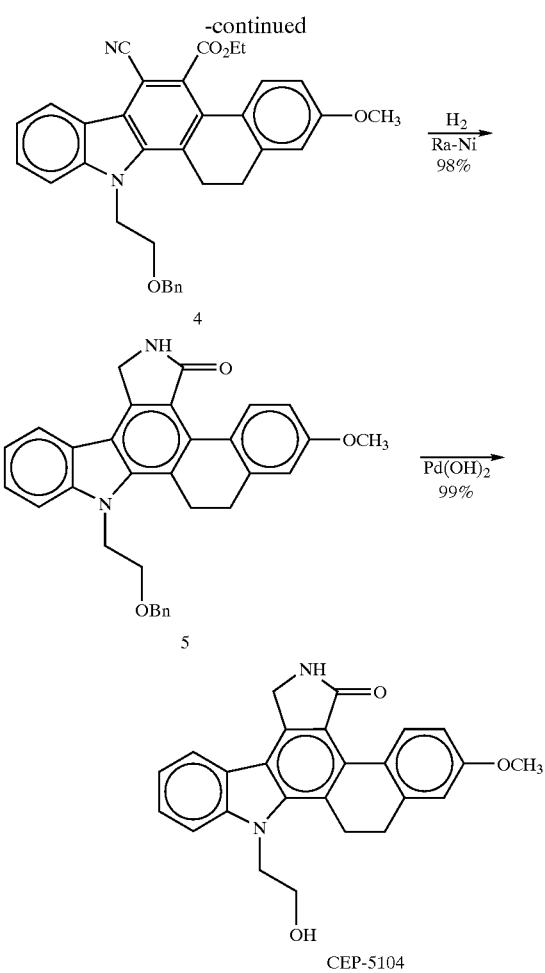

Preparation of 2:

The diene 1 (50 mg, 0.182 mmol), 7.5 mg (0.018 mmol) of ytterbium bromide and 68 mg (3 eq) of ethyl cyanoacrylate in 1 mL of toluene was heated under reflux for 3.5 hr. The product precipitated when the mixture was allowed to cool to room tempratture. The solid was filtered, washed with toluene to give 48 mg (66% theory) of the product 2 as off white solid. It was shown to be homogeneous by hplc. $^1$H NMR (DMSO-d6, 300 MHz): d 11.2 (s, 1H), 7.55 (bq, 1H), 7.35 (d, 1H), 7.2 (bq, 1H), 7.1 (t, 1H), 7.05 (t, 1H), 6.7 (bq, 1H), 6.55 (s, 1H), 3.7 (s, 3H), etc.

Preparation of 3:

To 60 g, (0.150 mol) of the diels alder adduct 2 suspended in 1.5 L of toluene was added 71.4 g (0.315 mol, 5% excess) of DDQ at room temperature with vigorous stirring. The temperature of the reaction mixture gradually rose to 33° C. over 1 hour period before returning to room temperature. The solid was collected on a filter, washed thoroughly with toluene and air dried. It was then dispersed in 2 L of water with vigorous stirring, and 80 g (theory 52.8 g) of sdium bicarbonate was added portion-wise. After stirring for 2 to 3 hours, the mixture was filtered and the solid was washed thoroughly with water until the washings were neutral. The crude product 3 weighed 61.5 g (96% purity by hplc). 1H NMR (DMSO-d6, 300 MHz): d 12.1 (s, 1H), 8.45 ( d, 1H), 7.60 (m, 2H), 7.25–7.4 (m, 2H), 7.0 (s, 1H), 6.9 (s, 1H), 4.35 (q, 2H), 3.8 (s, 3H), 3.15 (m, 2H), 2.9 (m,2H), 1.25 (t, 3H). The crude product was used for the next step without further purification.

Preparation of 4:

A mixture of 50 g (0.126 mol) of the cyanoester 3, 120 g (0.56 mol, 4.43 eq) of 2-bromoethylbenzyl ether and 250 mL of 10N sodium hyroxide in 1450 mL of acetone was heated under reflux overnight. Most of the acetone was removed under reduced pressure, 500 mL of water and 1250 mL of hexane were added and the mixture was stirre vigorously for 0.5 hr. The resulting solid was filtered, washed thouroughly with water until the washing became neutral. The solid was dried under vacuum, then washed with hexane to give 60 g of the product 4 (89.5% theory, 95% purity by hplc). 1H NMR (DMSO-d6, 300 MHz): d 8.55 (d, 1H), 7.85 (d, 1H), 7.15 (t, 1H), 7.4 (t, 1H), 7.25 (d, 1H), 7.15 (m, 3H), 7.0 (s, 1H), 6.9 (m, 3H), 4.9 (bs, 2H), 4.30 (m, 4H), 3.8 (m, 5H), 3.45 (t, 2H), 2.75 (t, 2H), 1.2 (t, 3H).

Preparation of 5:

A solution of 59.8 g (0.113 mol) of 4 in 1 L of DMF containing 100 mL of methanol was hydrogenated over 100 g of Raney nickel at 55 psi on a Parr apparatus. The catalyst was removed by filtration and the filtrate was concentrated under reduced pressure and the resulting semi-solid was triturated with 1.8 L of ether overnight to give 53.6 g of the lactam (93% theory) which was shown to contain 4% of further reduced product (debenzylated, 5104), 92% of desired product 5 and 4% impurity by hplc. 1H NMR (DMSO-d6, 300 MHz): d 8.45 (s, 1H), 7.95 (d, 1H), 7.85 (d, 1H), 7.7 (d, 1H), 7.50 (t, 1H), 7.3 (t, 1H), 7.15 (bq, 3H), 7.05 (bq, 2H), 6.85 (s, 1H), 6.80 (d, 1H), etc. The crude material was used for the subsequent reaction without further purification.

Preparation of the title compound

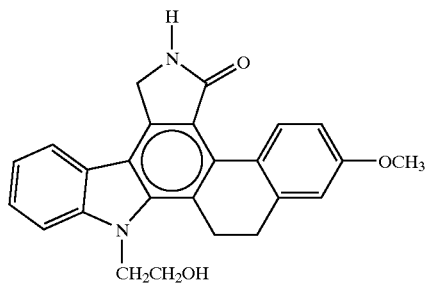

A solution of 43.6 g (89.2 mmol) of the lactam 5 in 1 L of DMF containing 5 drops of 12M hydrochloric acid was hydrogenated over 2.2 g of palladium hydroxide at 50 psi. The catalyst was removed by filtration through a bed of Celite, and the filtrate was concentrated under reduced pressure and the resulting semisolid was triturated with 2 L of ether overnight to give CEP-5104 as a pale yellowish solid, 36 g (100% theory, 97% purity by hplc. 1H NMR (DMSO-d6, 300 MHz): d 8.4 (s, 1H), 7.95 (d, 1H), 7.85 (d, 1H), 7.7 (d, 1H), 7.50 (t, 1H), 7.3 (t, 1H), 6.9 (s, 1H), 6.8 (d, 1H), 5.0 (bs, 1H), 4.8 (s, 2H), 4.65 (bt, 2H), 3.8 (bs, 5H), 3.3 (bt, 2H), 2.75 (bt, 2H). MS (ES+) m/e 399 (M+1).

EXAMPLE 12

The following fused pyrrolocarbazoles were prepared using the methods described herein.

EXAMPLE 12A

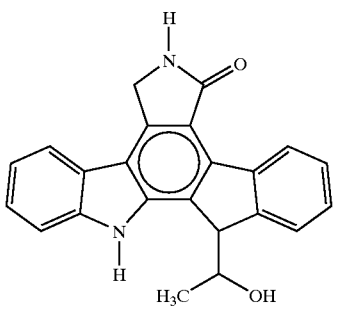

EXAMPLE 12B

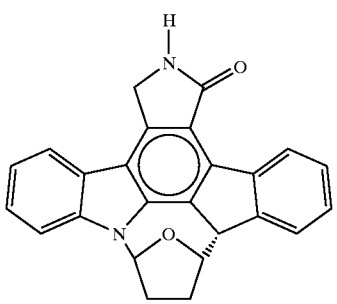

EXAMPLE 12C

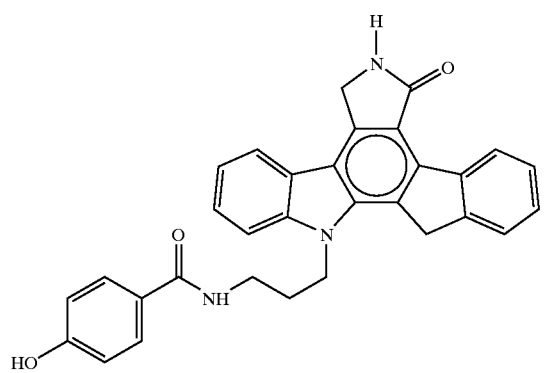

EXAMPLE 12D

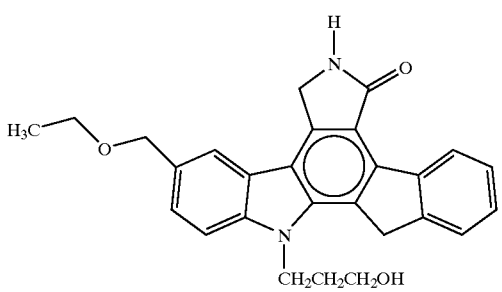

EXAMPLE 13

Preparation of 13-(3-hydroxypropyl)-3-(pyridyl-2-thiomethyl)-6H,12H-indeno[2,3-a]pyrrolo[3,4-c]carbazole-7(7H)one

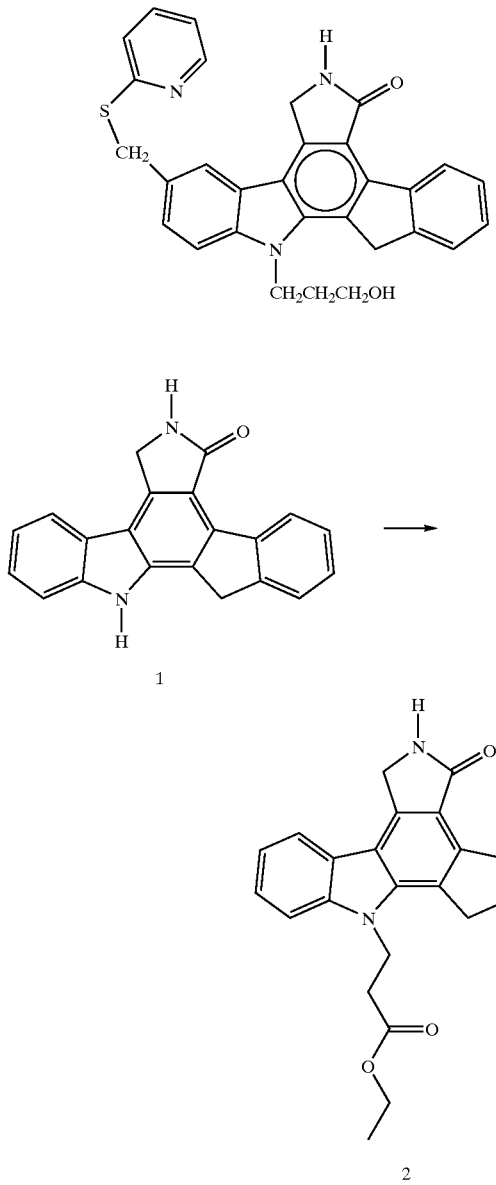

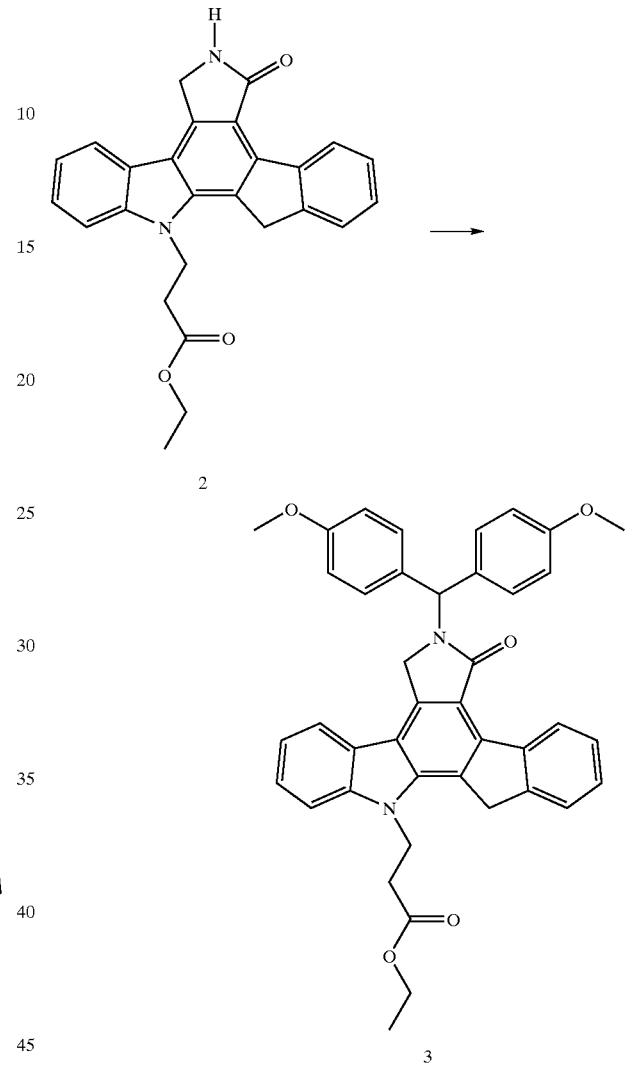

MHz): d 9.72 (t, 3H, J=6.8), 2.87 (m, 2H), 3.89 (q, 2H, J=6.8), 4.49 (s, 2H), 4.88 (s, 2H), 4.92 (m, 2H), 7.29–7.48 (m, 3H), 7.50–7.73 (m, 3H), 7.96 (d, 1H, J=7.33), 8.56 (s, 1H), 9.47 (d, 1H, J=7.33).

PREPARATION OF 2:

To a suspension of 1 (8.0 g, 0.258 mols) in acetonitrile (300 mL) at room temperature under nitrogen was added ethyl acrylate (4.19 mL, 0.387 mols) followed by 1,8-diazabicyclo[5.4.0]undec-7-ene (DBU) (1.93 mL, 0.013 mols). After addition of DBU, the reaction changed colors from orange to green. The reaction mixture was heated to reflux overnight. The mixture remained heterogeneous throughout the course of the reaction and became dark in color. A small aliquot was removed after 18 h and the solid was collected by filtration. 1H NMR of the sample showed no starting material remaining. The reaction mixture was cooled to room temperature and the solid was collected by filtration. The solid was washed several times with cold acetonitrile and dried in vacuo at 55° C. to yield a light orange solid (5.4 g, 78% yield). 1H NMR (DMSO-d6, 300

PREPARATION OF 3:

To a suspension of 2 (5.62 g, 0.0137 mols) in benzene (300 mL) and N-methylpyrrolidine (NMP) (60 mL) at room temperature under nitrogen was added p-toluenesulfonic acid monohydrate (2.48 g, 0.013 mols) and 4,4'-dimethoxybenzhydrol (3.19 g, 0.013 mols). The contents of the flask were heated to reflux for 8 h. After 45 min., the initially heterogeneous reaction mixture became homogeneous. The reaction mixture was cooled to room temperature, diluted with ethyl acetate (300 mL) and washed with a saturated bicarbonate solution, water, and brine. The organic layer was dried over magnesium sulfate, filtered and concentrated in vacuo to an orange solid (8.31 g, 95% yield). 1H NMR (CDCl3, 300 MHz): d 1.18 (t, 3H, J=7.1), 2.84 (m, 2H), 3.80 (6H, s), 4.12 (q, 2H, J=7.1), 4.38 (s, 2H), 4.72 (2H, s), 4.94 (m, 2H), 6.90 (d, 4H, J=8.5), 6.955 (s, 1H), 7.26 (d, 4H, J=8.5), 7.34–7.49 (m, 5H), 7.61 (d, 1H, J=7.4), 7.69 (d, 1H, J=7.7), 9.65 (d, 1H, J=7.8).

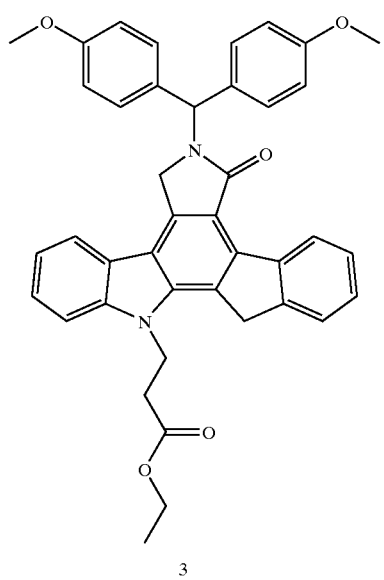

3

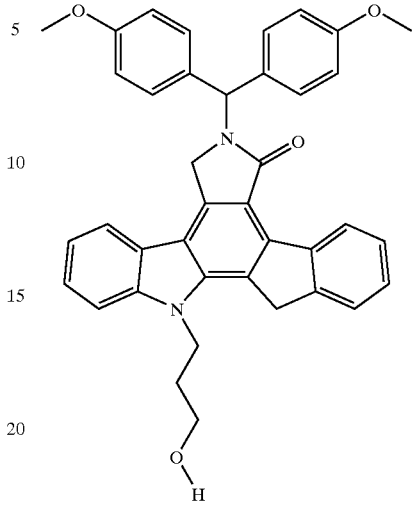

4

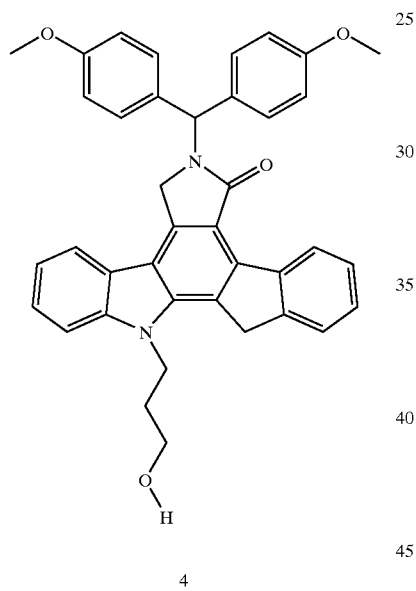

4

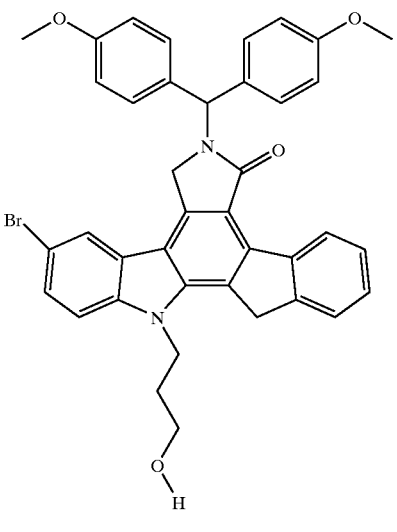

5

7.70 (d, 1H, J=8.26), 7.86 (d, 1H, J=7.82), 9.49 (d, 1H, J=7.49).

PREPARATION OF 4:

To a stirred solution of 3 (7.8 g, 0.0122 mols) in THF (480 mL) and methanol (93 mL) was added lithium borohydride (18.9 mL of a 2.0M soln, 0.0379 mols) dropwise. The reaction mixture was initially homogeneous, however, as the reaction proceeded, the mixture became heterogeneous. When all of the starting material had been consumed, the reaction mixture was cooled in an ice bath and carefully quenched with 2N HCl (60 mL). The reaction mixture became homogeneous and light orange in color. Water (750 mL) was added to the mixture and a milky white precipitate formed. The precipitate was collected by filtration and dried in vacuo to give a fluffy white solid (7.2 g, 99% yield). 1H NMR (DMSO-d6, 300 MHz): d 1.93 (m, 2H), 3.66 (m, 2H), 3.71 (s, 6H), 4.55 (s, 2H), 4.73 (m, 2H), 4.79 (s, 2H), 6.70 (s, 1H), 6.93 (d, 4H, J=8.44), 7.22 (d, 4H, J=8.4), 7.26 (m, 1H), 7.34–7.46 (m, 2H), 7.49 (m, 1H), 7.65 (d, 1H, J=7.01),

PREPARATION OF 5:

To a suspension of 4 (2.02 g, 0.0034 mols) in THF (131 mL) at room temperature under nitrogen was added N-bromosuccinimide (0.63 g, 0.0036 mols) in one portion. The reaction mixture stirred at room temperature overnight. The reaction solvent was removed in vacuo leaving a pale yellow solid. The solid was triturated with cold methanol and collected by filtration. The solid was dried in vacuo to give a pale yellow solid (1.98, 87% yield). 1H NMR (DMSO-d6, 300 MHz): d 1.91 (m, 2H), 3.44 (m, 2H), 3.72 (s, 6H), 4.53 (s, 2H), 474 (m, 2H), 4.87 (s, 2H), 6.71 (s, 1H), 6.93 (d, 4H, J=8.14), 7.25 (d, 4H, J=8.1), 7.37 (m, 2H), 7.59–7.69 (m, 3H), 8.08 (s, 1H), 9.50 (d, 1H, J=7.01).

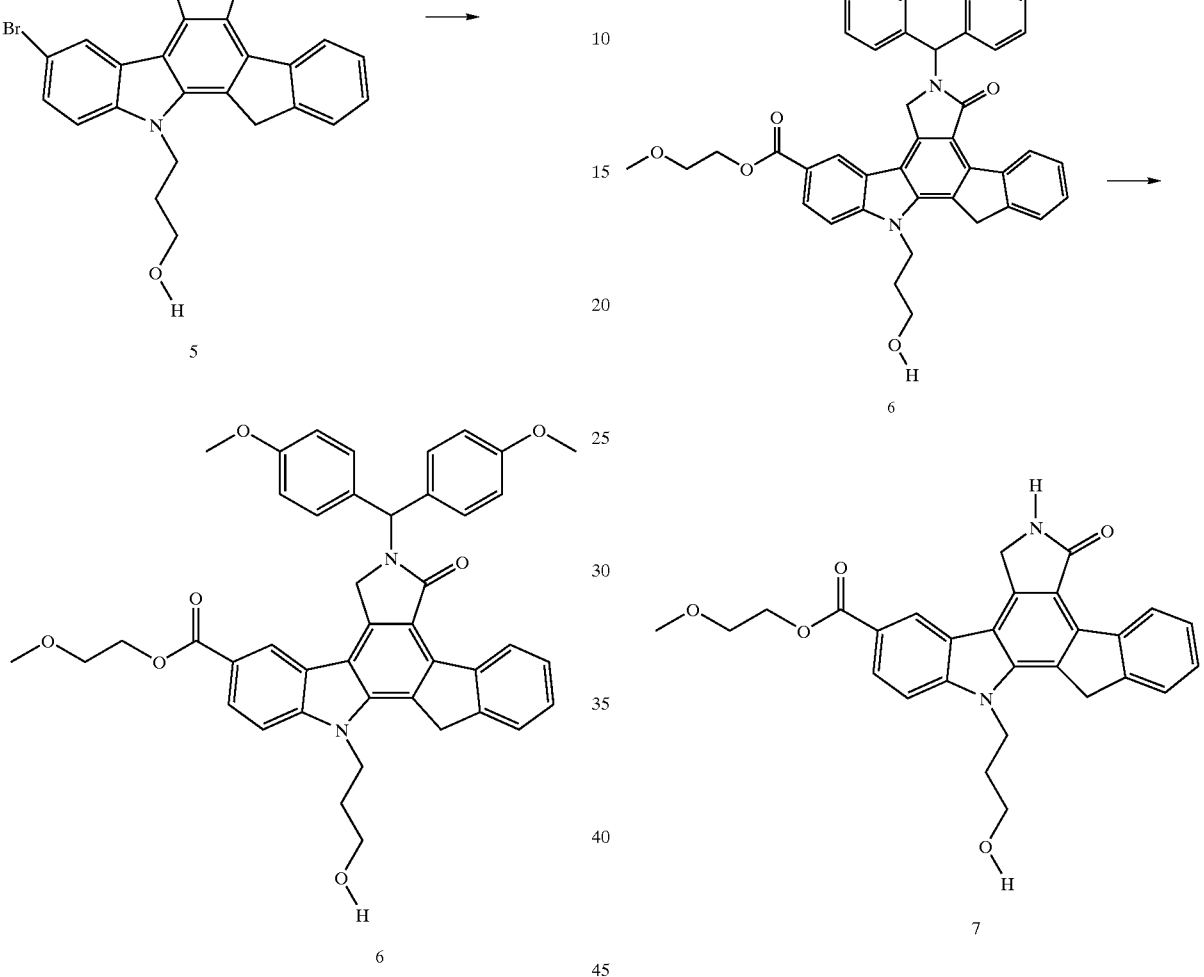

3.67–3.78 (m, 4H), 3.81 (s, 6H), 4.44 (s, 2H), 4.51 (m, 2H), 4.81 (m, 4H), 6.91 (d, 4H, J=8.53), 6.98 (s, 1H), 7.28 (d, 4H, 8.6), 7.34–7.7.61 (m, 4H), 8.21 (d, 1H, J=8.32), 8.42 (s, 1H), 9.67 (d, 1H, J=7.61).

PREPARATION OF 6:

In a Schlenk tube was placed 5 (0.79 g, 0.0017 mols) in methoxyethanol (25 mL) followed by sodium acetate (0.57 g, 0.00702 mols) and dichlorobis(triphenylphosphine)-palladium(II) (0.082 g, 0.000117 mols). The tube was evacuated and filled with carbon monoxide. The reaction mixture was heated in the sealed tube at 155° C. in an oil bath for 3 h. The reaction was cooled to room temperature and additional carbon monoxide was added. The mixture was reheated to 150° C. for another 3 h. Additional CO and PdCl2(PPh3)2 were added and the mixture heated for 4 h. The reaction mixture was diluted with methylene chloride and flushed through a pad of celite. The filtrate was concentrated in vacuo to a residue which was dissolved in ethyl acetate and washed with water. The organic layer was dried over magnesium sulfate, filtered, and concentrated in vacuo to a solid which was triturated with ethyl ether and collected by filtration to yield a light orange solid (0.7 g, 85% yield). 1H NMR (CDCl3, 300 MHz): d 2.14 (m, 2H), 3.44 (s, 3H),

PREPARATION OF 7:

To a solution of 6 (0.96 g, 0.00138 mols) in CH2Cl2 (30 mL) at 0° C. under nitrogen was added thioanisole (3.2 mL, 0.110 mols) followed by trifluoroacetic acid (TFA)(8.5 mL, 0.0276 mols). Upon addition of TFA, the reaction mixture turned red in color. The mixture stirred at 0° C. for 1 h and was warmed to room temperature overnight. The reaction solvent was removed in vacuo leaving a dark red oil. Ethyl ether was added to the oil and the reaction mixture turned yellow in color and a tan solid precipitated out of solution. The solid was collected by filtration (0.6 g, 92% yield). 1H NMR (DMSO-d6, 300 MHz): d 2.29 (m, 2H), 3.3 (m, 2H), 3.73 (m, 2H), 4.45 (m, 2H), 4.54 (m, 3H), 4.82 (m, 2H), 4.99 (s, 2H), 7.40 (m, 2H), 7.58 (d, 1H), 7.85 (d, 1H), 8.13 (d, 1H), 8.52 (s, 1H), 8.6 (s, 1H), 9.49 (d, 1H).

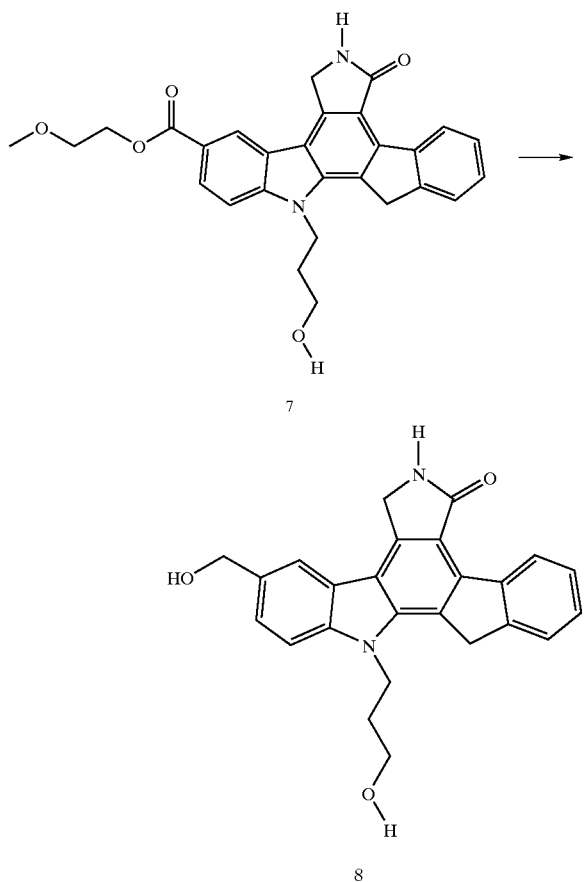

7

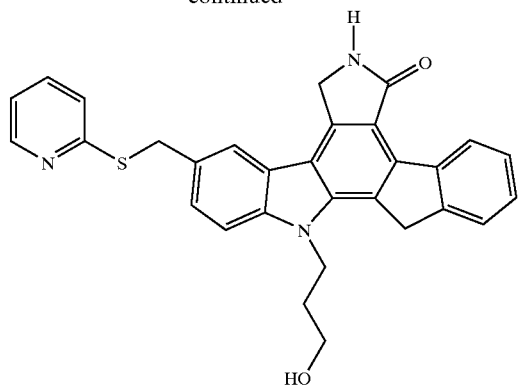

9

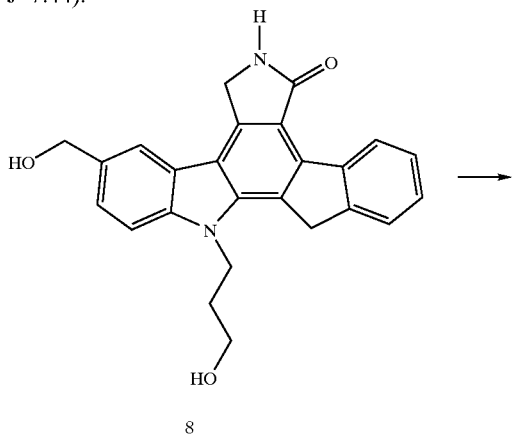

8

PREPARATION OF 8:

To a stirred suspension of 7 (4.4 g, 0.00935 mols) in CHCl2 (220 mL) at 0° C. under nitrogen was added DIBAL-H slowly dropwise. The reaction gradually became homogeneious. The orange-colored reaction mixture stirred at 0° C. for 1 h then was warmed to room temperature and was stirred for 6 h. The mixture was cooled to 0° C. in an ice bath and water (50 mL) was added extremely slowly initially. Vigorous evolution of gas was observed. An aqueous solution of NaOH (1M, 300 mL) was added and the reaction mixture stirred at room temperature for 1 h. A precipitate formed and was collected by filtration to yield a tan solid (3.6 g, 96%). 1H NMR (DMSO-d6, 300 MHz): d 1.92 (m, 2H), 3.46 (m, 2H), 4.50 (s, 2H), 4.65 (s, 2H), 4.71 (m, 2H), 4.88 (s, 2H), 7.32–7.39 (m, 2H), 7.47 (d, 1H, J=8.34), 7.65 (m, 2H), 7.89 (s, 1H), 8.53 (s, 1H), 9.46 (d, 1H, J=7.44).

PREPARATION OF 9:

To a suspension of 8 (105.6 mg, 0.265 mmols) in dioxane (3 mL) was added 2-mercaptopyridine (73.7 mg, 0.663 mmols) and camphorsulfonic acid (184.7 mg, 0.795 mmols). The suspension was heated in a sealed tube at 80° C. for 5 h during which time the reaction mixture became a homogeneous solution. The reaction mixture was cooled to room temperature overnight. Thin layer chromatography (100% ethyl acetate) showed a small amount of starting material present so the mixture was heated for an additional 6 h at 80° C. After cooling to room temperature, the reaction mixture was triturated with ethyl ether. A solid precipitated out of solution and was collected by filtration. The solid was suspended in ethyl acetate and washed with a saturated sodium bicarbonate solution to remove the camphorsulfonic acid. The organic layer was dried over sodium sulfate, filtered and concentrated in vacuo to a light orange solid. The solid was triturated with ethyl ether and collected by filtration to yield pure product (67 mg, 51% yield). MS (ESI): m/e 514 (M+Na)+, 1H NMR (DMSO-d6, 300 MHz): d 1.014 (m, 2H), 3.45 (m, 2H), 4.51 (s, 2H), 4.60 (s, 2H), 4.72 (m, 3H), 4.85 (s, 2H), 7.11 (m, 1H), 7.30–7.41 (m, 3H), 7.54–7.67 (m, 4H), 8.02 (s, 1H), 8.48 (d, 1H, J=3.97), 8.55 (s, 1H), 9.46 (d, 1H, J=7.36).

EXAMPLE 14

The following fused pyrrolocarbazoles were prepared using the methods described herein.

EXAMPLE 14A

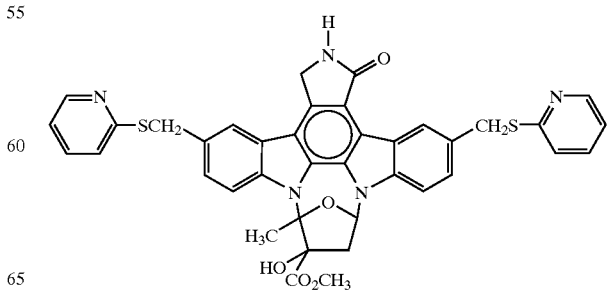

EXAMPLE 14B

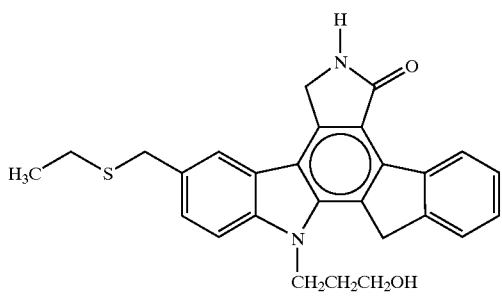

EXAMPLE 15

Protective effect of the different compounds of Formula I and the compound of Formula II against neomycin in neonatal rat cochlear explants The compounds of Formula I and the compound of Formula II attenuated neomycin-induced cochlear sensory hair cell loss in vitro. The effect of the compounds of Formula I and the compound of Formula II on neomycin-induced hair cell degeneration was determined in organotypic cultures of the neonatal organ of Corti.

Cochlear cultures.

The basal half of cochleas containing the basal and middle turns were dissected from postnatal day 2 Wistar rats. The cultures were maintained on Nuclepore filters (pore size 0.1 mm; Pleasanton, Calif.) placed on a metal grid in F12 medium (Life Technologies, Gaithersburg, Md.) containing 15% fetal bovine serum (Life Technologies). After a 2-hour-long stabilization period, explants were exposed to 100 μM neomycin sulfate (Sigma, St Louis, Mo.) for 48 hr. The compounds of Formula I and the compound of Formula I were added at 500 nM at the time of initiation of the cultures and every 12 hr thereafter. Neomycin plus vehicle was used as a control.

Hair cell counts in cochlear cultures.

Explants were fixed with 4% paraformaldehyde/0.5% glutaraldehyde in phosphate buffered saline (PBS), pH 7.4, for 30 min and dissected for surface preparations. They were stained with a 1:100 dilution of rhodamine-phalloidin in PBS containing 0.25% Triton X-100 overnight at 4° C. and mounted in Vectashield (Vector). Outer hair cell (OHC) numbers were quantified with a Zeiss Axiovert 100/135 epifluorescent microscope (Germany) connected to a Bio-Rad MRC-1024 confocal laser scanning system (Richmond, Calif.). Hair cells were characterized as missing if no stereocilia and cuticular plate were observed. Numbers of OHCs were evaluated using a 40x objective lens and an ocular grid. Several fields filled by 30 OHCs in each of the 3 rows (when all of them were present) were studied from each explant. Basal and middle coils were analyzed separately.

Results

When the cultures were treated with 100 μM neomycin, many sensory hair cells were lost within 48 hours. 100μM neomycin caused the loss of most basally located sensory hair cells, as detected in surface preparations of the cultures using F-actin (phalloidin) as a sensory hair cell marker. When 500 nM of the compounds of Formula I was added to the cultures together with neomycin, different levels of sensory hair cell protection was achieved. Table 6 shows the protection against loss of sensory hair cell degeneration by coincubation with the compounds of Formula I and the compound of Formula II. Datapoints marked with "**" indicate results which are thought to be indicative of artifacts.

TABLE 6

Compounds of Formula I and Formula II in Cochlear Cultures

| Compound | # fields | total HCs | missing HCs | % preserved |
|---|---|---|---|---|
| Example 8 | 11 | 1320 | 1040 | 21 |
| Example 8 | 9 | 1080 | 850 | 21 |
| Example 9 | 15 | 1560 | 1060 | 32 |
| Example 9 | 10 | 1200 | 890 | 26 |
| Example 9 | 9 | 1080 | 240 | 78** |
| Example 9 | 8 | 960 | 840 | 13 |
| Example 10 | 8 | 960 | 115 | 88 |
| Example 10 | 10 | 1200 | 20 | 98 |
| Example 10 | 10 | 1200 | 120 | 98 |
| Example 10 | 7 | 840 | 20 | 98 |
| Example 10 | 7 | 840 | 200 | 76 |
| Example 11 | 6 | 720 | 585 | 19 |
| Example 11 | 8 | 960 | 420 | 56 |
| Example 11 | 8 | 960 | 620 | 35 |
| Example 11 | 13 | 1560 | 845 | 46 |
| Example 12A | 6 | 720 | 500 | 25 |
| Example 12A | 7 | 840 | 500 | 60 |
| Example 12A | 8 | 960 | 700 | 35 |
| Example 12A | 10 | 1200 | 1100 | 10 |
| Example 12A | 5 | 600 | 120 | 20 |
| Example 12B | 6 | 720 | 20 | 97 |
| Example 12B | 18 | 2160 | 560 | 74** |
| Example 12B | 4 | 480 | 20 | 95 |
| Example 12C | 8 | 960 | 720 | 25 |
| Example 12C | 10 | 1200 | 600 | 50 |
| Example 12C | 8 | 960 | 860 | 10 |
| Example 12D | 10 | 1200 | 1000 | 17 |
| Example 12D | 7 | 840 | 725 | 12 |
| Example 12D | 8 | 960 | 620 | 35 |
| Example 13 | 4 | 480 | 80 | 83 |
| Example 13 | 6 | 720 | 270 | 62 |
| Example 13 | 10 | 1200 | 570 | 50 |
| Example 14A | 11 | 1320 | 910 | 31 |
| Example 14A | 8 | 960 | 840 | 12 |
| Example 14A | 8 | 960 | 900 | 6 |
| Example 14B | 9 | 1080 | 520 | 50 |
| Example 14B | 8 | 960 | 830 | 15 |
| Example 14B | 9 | 1080 | 1005 | 5 |
| Formula II | 7 | 840 | 70 | 92 |
| Formula II | 8 | 960 | 165 | 83 |
| Fonnula II | 10 | 1200 | 60 | 95 |
| Formula II | 4 | 480 | 15 | 97 |
| NEO | 11 | 1320 | 1270 | 4 |
| NEO | 7 | 840 | 680 | 19 |
| NEO | 9 | 1080 | 1040 | 4 |
| NEO | 12 | 1440 | 1210 | 16 |

The disclosures of each patent, patent application and publication cited or described in this document are hereby incorporated by reference herein in their entirety.

Various modifications of the invention, in addition to those described herein, will be apparent to those skilled in the art from the foregoing description. Such modifications are also intended to fall within the scope of the appended claims.

What is claimed is:

1. A method for preventing hearing loss in a subject, said method comprising:

administering to said subject an effective amount of a fused pyrrolocarbazole of Formula I having the formula:

FORMULA I

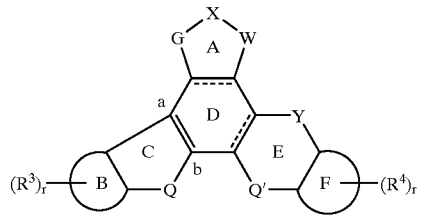

or a stereoisomer or pharmaceutically acceptable salt form thereof, wherein:

ring D is selected from phenyl and cyclohexene with double bond a-b;

ring B and ring F are independently selected from:
(a) a 6-membered carbocyclic ring in which from 1 to 3 carbon atoms may be replaced by heteroatoms;
(b) a 5-membered carbocyclic ring; and
(c) a 5-membered carbocyclic ring in which either:
(1) one carbon atom is replaced with an oxygen, nitrogen, or sulfur atom;
(2) two carbon atoms are replaced with a sulfur and a nitrogen atom, an oxygen and a nitrogen atom, or two nitrogen atoms; or
(3) three carbon atoms are replaced with three nitrogen atoms, one oxygen and two nitrogen atoms, or one sulfur and two nitrogen atoms;

G-X-W is selected from:
(a) $(Z^1Z^2)C-N(R^1)-C(Z^1Z^2)$;
(b) $CH(R^1)-C(=O)-N(R^1)$; and
(c) $N(R^1)-C(=O)-CH(R^1)$;

$Z^1$ and $Z^2$, at each occurrence, are independently selected from H, H; H, OR; H, SR; H, $N(R)_2$; and a group wherein $Z^1$ and $Z^2$ together form a moiety selected from $=O$, $=S$, and $=NR$; with the proviso that at least one of the pairs $Z^1$ and $Z^2$ forms $=O$;

R is independently selected from H, optionally substituted alkyl, OH, alkoxy, $OC(=O)R^{1a}$, $OC(=O)NR^{1c}R^{1d}$, $O(CH_2)pNR^{1c}R^{1d}$, $O(CH_2)_pOR^{1b}$, optionally substituted arylalkyl and optionally substituted heteroarylalkyl;

$R^1$ is independently selected from:
(a) H, optionally substituted alkyl, optionally substituted aryl, optionally substituted arylalkyl, optionally substituted heteroaryl and optionally substituted heteroarylalkyl;
(b) $C(=O)R^{1a}$;
(c) $OR^{1b}$;
(d) $C(=O)NHR^{1b}$, $NR^{1c}R^{1d}$, $(CH_2)pNR^{1c}R^{1d}$, $(CH_2)_pOR^{1b}$, $O(CH_2)_pOR^{1b}$ and $O(CH_2)_pNR^{1c}R^{1d}$;

$R^{1a}$ is independently selected from optionally substituted alkyl, optionally substituted aryl and optionally substituted heteroaryl;

$R^{1b}$ is independently selected from H and optionally substituted alkyl;

$R^{1c}$ and $R^{1d}$ are each independently selected from H, optionally substituted alkyl and a linking group of the formula $(CH_2)_2-X^1-(CH_2)_2$;

$X^1$ is independently selected from O, S and $CH_2$;

Q is selected from $NR^2$, O, S, $NR^{22}$, $CHR^{23}$, $X^4CH(R^{23})$, $CH(R^{23})X^4$, wherein $X^4$ is selected from O, S, $CH_2$, $NR^{22}$ and $NR^2$;

$R^2$ is selected from H, $SO_2R^{2a}$, $CO_2R^{2a}$, $C(=O)R^{2a}$, $C(=O)NR^2CR^{2d}$, optionally substituted alkyl, optionally substituted alkenyl and optionally substituted alkynyl, wherein said optional substituents are one to about three $R^5$ groups;

$R^{2a}$ is independently selected from optionally substituted alkyl, optionally substituted aryl, optionally substituted carbocyclyl, optionally substituted heterocyclyl, $OR^{2b}$, $CONH_2$, $NR^{2c}R^{2d}$, $(CH_2)_pNR^{2c}R^{2d}$ and $O(CH_2)_pNR^{2c}R^{2d}$;

$R^{2b}$ is selected from H and optionally substituted alkyl;

$R^{2c}$ and $R^{2d}$ are each independently selected from H and optionally substituted alkyl, or together form a linking group of the formula $(CH_2)_2-X'-(CH_2)_2$;

$R^3$ and $R^4$ are each independently selected from:
(a) H, aryl, heteroaryl, F, Cl, Br, I, CN, $CF_3$, $NO_2$, OH, $OR^9$, $O(CH_2)_pNR^{11}R^{12}$, $OC(=O)R^9$, $OC(=O)NR^{11}R^{12}$, $O(CH_2)_pOR^{11}$, $CH_2OR^{10}$, $NR^{11}R^{12}$, $NR^{10}S(=O)_2R^9$ and $NR^{10}C(=O)R^9$;
(b) $CH_2OR^{14}$;
(c) $NR^{10}C(=O)NR^{11}R^{12}$, $CO_2R^{10}$, $C(=O)R^9$, $C(=O)NR^{11}R^{12}$, $CH=NOR^{10}$, $CH=NR^{10}$, $(CH_2)_pNR^{11}R^{12}$, $(CH_2)_pNHR^{14}$ and $CH=NNR^{11}R^{12}$;
(d) $S(O)_yR^9$, $(CH_2)_pS(O)_yR^9$ and $CH_2S(O)_yR^{14}$;
(e) optionally substituted alkyl, optionally substituted alkenyl and optionally substituted alkynyl, wherein said optional substituents are one to about three $R^5$ groups;

$R^9$ is selected from alkyl, $(CH_2)_r$aryl and $(CH_2)_r$heteroaryl;

$R^{10}$ is selected from H, alkyl, $(CH_2)_r$aryl and $(CH_2)_r$heteroaryl;

$R^{11}$ and $R^{12}$ are independently selected from H and optionally substituted alkyl, or together form a linking group of the formula $(CH_2)_2-X^1-(CH_2)_2$;

$R^5$ is selected from aryl, heteroaryl, arylalkoxy, heterocycloalkoxy, hydroxyalkoxy, alkyloxy-alkoxy, hydroxyalkylthio, alkoxy-alkylthio, F, Cl, Br, I, CN, $NO_2$, OH, $OR^9$, $X^2(CH_2)_pNR^{11}R^{12}$, $X^2(CH_2)_pC(=O)NR^{11}R^{12}$, $X^2(CH_2)_pOC(=O)NR^{11}R^{12}$, $X^2(CH_2)_pCO_2R^9$, $X^2(CH_2)_pS(O)_yR^9$, $X^2(CH_2)_pNR^{10}C(=O)NR^{11}R^{12}$, $OC(=O)R^9$, $OC(=O)NHR^{10}$, O-tetrahydropyranyl, $NR^{11}R^{12}$, $NR^{10}C(=O)R^9$, $NR^{10}CO_2R^9$, $NR^{10}C(=O)NR^{11}R^{12}$, $NHC(=NH)NH_2$, $NR^{10}S(O)_2R^9$, $S(O)_yR^9$, $CO_2R^{10}$, $C(=O)NR^{11}R^{12}$, $C(=O)R^9$, $CH_2OR^{10}$, $CH=NNR^{11}R^{12}$, $CH=NOR^{10}$, $CH=NR^9$, $CH=NNHCH(N=NH)NH_2$, $S(=O)_2NR^{11}R^{12}$, $P(=O)(OR^{10})_2$, $OR^{14}$, and a monosaccharide wherein each hydroxyl group of the monosaccharide is independently either unsubstituted or is replaced by H, alkyl, alkylcarbonyloxy, or alkoxy;

$X^2$ is O, S, or $NR^{10}$;

Y is selected from:
(a) a direct bond;
(b) optionally substituted $CH_2$, $CH_2CH_2$ or $CH_2CH_2CH_2$, wherein said optional substituents are one to about three $R^{19}$ groups; and
(c) $CH=CH$, $CH(OH)-CH(OH)$, O, S, $S(=O)$, $S(=O)2$, $C(R^{18})_2$, $C=C(R^{19})_2$, $C(=O)$, $C(=NOR^{20})$, $C(OR^{20})R^{20}$, $C(=O)CH(R^{18})$, $CH(R^{18})C(=O)$, $C(=NOR^{20})CH(R^{18})$, $CHR^{21}C(=NOR^{20})$, $C(=O)N(R^{21})$, $N(R^{21})C(=O)$, $CH_2Z$, $ZCH_2$ and $CH_2ZCH_2$, where Z is selected from $C(R^{21})_2$, O, S, $CO_2R^{20}$, $C(=NOR^{20})$ and $N(R^{20})$;

$R^{18}$ is independently selected from H, $SO_2R^{18a}$, $CO_2R^{18a}$, $C(=O)R^{18a}$, $C(=O)NR_{18c}CR^{18d}$, optionally substituted alkyl, optionally substituted alkenyl, and optionally substituted alkynyl;

89

$R^{18a}$ is independently selected from optionally substituted alkyl, optionally substituted aryl, optionally substituted carbocyclyl and optionally substituted heterocyclyl;

$R^{18a}$ and $R^{18d}$ are each independently selected from H and optionally substituted alkyl, or together form a linking group of the formula $(CH_2)_2$—X'—$(CH_2)_2$;

$R^{19}$ is independently selected from $R^{20}$, thioalkyl, halogen, optionally substituted alkyl, optionally substituted alkenyl and optionally substituted alkynyl;

$R^{20}$ is independently selected from H, alkyl, OH, alkoxy, $OC(=O)R^{18a}$, $OC(=O)NR^{18c}R^{18d}$, $OC(=S)NR^{18c}R^{18d}$, $O(CH_2)_pNR^{18c}R^{18d}$, $O(CH_2)_pOR^{21}$, optionally substituted arylalkyl, optionally substituted heterocyclylalkyl and optionally substituted carbocyclyl;

$R^{21}$ is independently selected from H and alkyl;

Q' is selected from:
 (a) a direct bond;
 (b) $NR^6$;
 (c) optionally substituted $CH_2$, $CH_2CH_2$ or $CH_2CH_2CH_2$;
 (d) $CR^{22}R^{24}$; and
 (e) CH=CH, CH(OH)CH(OH), O, S, S(=O), S(=O)$_2$, C(=O), C(=$NOR^{11}$), C($OR^{11}$)($R^{12}$), C(=O)CH($R^{13}$), CH($R^{13}$)C(=O), C($R^{10}$)$_2$, C(=$NOR^{11}$)CH($R^{13}$), CH($R^{13}$)C(=$NOR^{11}$), $CH_2Z'$, Z'—$CH_2$ and $CH_2Z'CH_2$;

Z' is selected from C($R^{11}$)($R^{12}$), O, S, C(=O), C(=$NOR^{11}$) and $NR^{11}$;

$R^6$ is selected from H, $SO_2R^{2a}$, $CO_2R^{2a}$, C(=O)$R^{2a}$, C(=O)$NR^{1a}$, $CR^{1d}$, optionally substituted alkyl, optionally substituted alkenyl, and optionally substituted alkynyl, wherein said optional substituents are one to about three $R^5$ groups; or alternatively, when Q is $NR^2$ and Q' is $NR^6$ or C($R^{10}$)$_2$, $R^2$ and $R^6$ or one of $R^{10}$ are joined together to form:

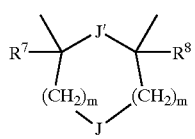

wherein $R^7$ and $R^8$ are each independently selected from H, OH, alkyl, alkoxy, optionally substituted arylalkyl, optionally substituted heteroarylalkyl, $(CH_2)_pOR^{10}$, $(CH_2)_pOC(=O)NR^{11}R^{12}$ and $(CH_2)_pNR^{11}R^{12}$; or $R^7$ and $R^8$ together form a linking group of the formula $CH_2$—$X^3$—$CH_2$;

$X^3$ is a bond, O, S, or $NR^{10}$;

J is selected from a bond, O, CH=CH, S, C(=O), CH($OR^{10}$), N($R^{10}$), N($OR^{10}$), CH($NR^{11}R^{12}$), C(=O)N($R^{17}$), N($R^{17}$)C(=O), N(S(O)$_x R^9$), N(S(O)$_y NR^{11}R^{12}$), N(C(=O)$R^7$), C($R^{15}R^{16}$), $N^+(O^-)(R^{10})$, CH(OH)CH(OH) and CH(O(C=O)$R^9$)CH(OC(=O)$R^9$);

J' is selected from O, S, N($R^{10}$), $N^+(O^-)(R^{10})$, N(O$R^{10}$) and $CH_2$;

$R^{13}$ is selected from alkyl, aryl and arylalkyl;

$R^{14}$ is the residue of an amino acid after the hydroxyl group of the carboxyl group is removed;

$R^{15}$ and $R^{16}$ are independently selected from H, OH, C(=O)$R^{10}$, O(C=O)$R^9$, alkyl-OH, alkoxy and $CO_2R^{10}$;

$R^{17}$ is selected from H, alkyl, aryl and heteroaryl;

90

$R^{22}$ is

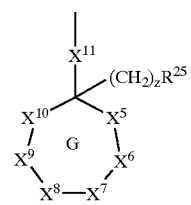

$X^5$ and $X^6$ are independently selected from O, N, S, $CHR^{26}$, C(OH)$R^{26}$, C(=O) and $CH_2$=C;

$X^7$ and $X^8$ are independently selected from a bond, O, N, S, $CHR^{26}$, C(OH)$R^{26}$, C(=O) and $CH_2$=C;

$X^9$ and $X^{10}$ are independently selected from a bond, O, N, S, C(=O) and $CHR^{26}$;

$X^{11}$ is a bond or alkylene optionally substituted with $NR^{11}R^{12}$ or $OR^{30}$;

$R^{23}$ is selected from H, $OR^{27}$, $SR^{27}$, $R^{22}$ and $R^{28}$;

$R^{24}$ is selected from R, thioalkyl, and halogen;

$R^{25}$ is selected from $R^1$ and OC(=O)$NR^{1c}R^{1d}$;

$R^{26}$ is selected from H, optionally substituted alkyl and optionally substituted alkoxy, wherein
 (1) ring G contains 0 to about 3 ring heteroatoms;
 (2) any two adjacent hydroxyl groups of ring G can be joined to form a dioxolane ring;
 (3) any two adjacent ring carbon atoms of ring G can be joined to form a fused aryl or heteroaryl ring; with the provisos that:
  (a) when $X^{11}$ is a bond, ring G can be heteroaryl; and
  (b) ring G:
   (i) contains at least one carbon atom that is saturated;
   (ii) does not contain two adjacent ring O atoms;
   (iii) contains a maximum of two C(=O) groups;

$R^{27}$ is selected from H and alkyl;

$R^{28}$ is selected from aryl, arylalkyl, $SO_2R^{29}$, $CO_2R^{29}$, C(=O)$R^{29}$, optionally substituted alkyl, optionally substituted alkenyl and optionally substituted alkynyl;

$R^{29}$ is selected from alkyl, aryl and heteroaryl;

$R^{30}$ is selected from H, alkyl, acyl and C(=O)$NR^{11}R^{12}$;

m is independently selected from 0, 1, and 2;

p is independently selected from 1, 2, 3, and 4;

r is independently selected from 0, 1, and 2;

y is independently selected from 0, 1 and 2; and z is selected from 0, 1, 2, 3 and 4;

with the provisos that at least one of Y and Q' is a direct bond, when Y is a direct bond, Q' is other than a direct bond, when Q' is a direct bond, Y is other than a direct bond, and when rings B and F are phenyl, G-X-W is $CH_2NHC(=O)$, Y is a direct bond, Q is $NR^2$ and Q' is $NR^6$ where $R^6$ is joined with $R^2$ to form

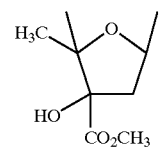

then $R^3$ is other than $CH_2SCH_2CH_3$.

2. A method according to claim 1 wherein,

Y is a direct bond; and

Q is $NR_2$.

3. A method according to claim 2 wherein ring B and ring F of the fused pyrrolocarbazole are phenyl, G-X-W is selected from $CH_2NR^1C(=O)$, $C(=O)NR^1CH_2$, and $C(=O)NR^1C(=O)$, and Q' is $NR^6$.

4. A method according to claim 3 wherein the fused pyrrolocarbazole has the formula:

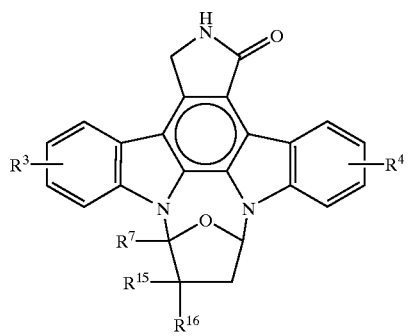

5. A method according to claim 4 wherein $R^3$ and $R^4$ of the fused pyrrolocarbazole are selected from H, alkyl, Cl, Br, $CH_2OH$, $CH_2SOCH_2CH_3$, $CH_2SO_2CH_2CH_3$, $NHCONHC_6H_5$, $CH_2SCH_2CH_3$, $CH_2S$-phenyl, $CH_2S$-pyridyl, $CH\ NHCO_2CH_3$, $CH_{20}C(=O)NHCH_2CH_3$, $N(CH_3)_2$, $CH=NNH$, $CH_2N(CH_3)_2$, and $CH_2OCH_2CH_3$; $R^7$ is selected from H and alkyl; and $R^{15}$ and $R^{16}$ are independently selected from H, alkyl, OH, $CH_2OH$, alkoxy, and $CO_2$alkyl.

6. A method according to claim 5 wherein the fused pyrrolocarbazole has the formula:

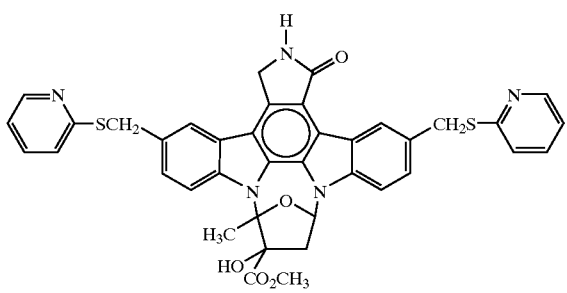

7. A method according to claim 2 wherein

Q' is $CH_2$, $CH_2CH_2$, S or $CH(CH(CH_3)(OH))$.

8. A method according to claim 7 wherein ring B and ring F of the fused pyrrolocarbazole are phenyl and G-X-W is selected from $CH_2NR^1C(=O)$, $C(=O)NR^1CH_2$.

9. A method according to claim 8 wherein the fused pyrrolocarbazole has the formula

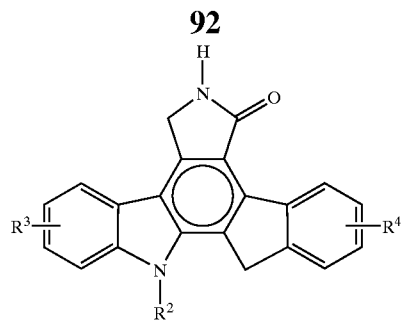

10. A method according to claim 9 wherein $R^2$ is H, $CH_2CH_2OH$, $CH_2CH_2NHC(=O)-C_6H_5$-OH, $CH_2CH_2CH_2OH$, $R^3$ and $R^4$ of the fused pyrrolocarbazole are elected from H, alkyl, Cl, Br, alkoxy, $CH_2OH$, $CH_2SOCH_2CH_3$, $CH_2SO_2CH_2CH_3$, $NHCONHC_6H_5$, $CH_2SCH_2CH_3$, $CH_2S$-phenyl, $CH_2S$-pyridyl, $CHNHCO_2CH_3$, $CH_2OC(=O)NHCH_2CH_3$, $N(CH_3)_2$, $CH=NNH$, $CH_2N(CH_3)_2$, and $CH_2OCH_2CH_3$; $R^7$ is selected from H and alkyl; and $R^{15}$ and $R^{16}$ are independently selected from H, alkyl, OH, $CH_2OH$, alkoxy, and $CO_2$alkyl.

11. A method according to claim 10 wherein the fused pyrrolocarbazole has the formula:

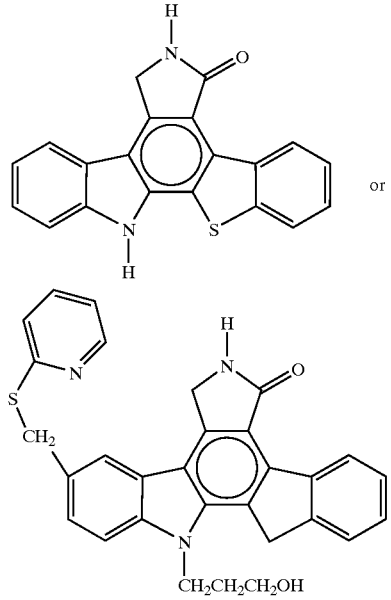

or

12. A method according to claim 8 wherein the fused pyrrolocarbazole has the formula:

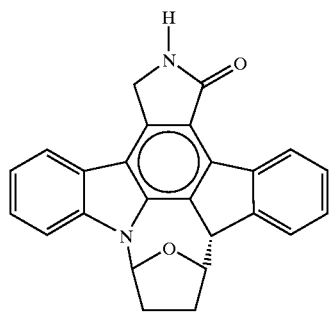

* * * * *

UNITED STATES PATENT AND TRADEMARK OFFICE
CERTIFICATE OF CORRECTION

PATENT NO. : 6,448,283 B1
DATED : September 10, 2002
INVENTOR(S) : Jukka Ylikoski et al.

It is certified that error appears in the above-identified patent and that said Letters Patent is hereby corrected as shown below:

Title page,
Item [56], References Cited, OTHER PUBLICATIONS, "Behrens et al.," reference, please delete "phosphorylationof" and insert -- phosphorylation of -- therefor.
"Malgrange et al.," reference, please delete "ainoglycoside" and insert -- aminoglycoside -- therefor.
"Maroney et al.," reference, please delete "18(91)" and insert -- 18(1) -- therefor.

Column 7,
Line 20, please delete "0" and insert -- O -- therefor.

Colunm 8,
Line 60, please delete "$CO_2R^{2c}$" and insert -- $CO_2R^{2a}$ -- therefor.

Column 17,
Line 12, please delete "$R_{1d}$" and insert -- $R^{1d}$ -- therefor.

Column 19,
Line 57, please delete "0" and insert -- O -- therefor.

Column 21,
Line 24, please delete "preffered" and insert -- preferred -- therefor.

Column 25,
Line 36, please delete "$CO_2R^{18}$" and insert -- $CO_2R^{18a}$ -- therefor.

Column 39,
Line 1, please delete "$OC(=O)NR^{1c}CR^{1d}$" and insert -- $OC(=O)NR^{1c}R^{1d}$ -- therefor.

Column 45,
Line 27, please delete "R' " and insert -- $R^5$ -- therefor.

Column 47,
Line 15, please delete "0" and insert -- O -- therefor.

Column 50,
Line 24, please delete "$CHR21C$" and insert -- $CHR^{21}C$ -- therefor.
Line 29, please delete "$C(=O)NR^{18}CR^{18d}$" and insert -- $C(=O)NR^{18c}R^{18d}$ -- therefor.
Line 43, please delete "$O(CH_2)_pNR^{18c}R^{18d}O(CH_2)_pOR^{21}$" and insert
-- $O(CH_2)_pNR^{18c}R^{18d}O(CH_2)_pOR^{21}$ -- therefor.

UNITED STATES PATENT AND TRADEMARK OFFICE
CERTIFICATE OF CORRECTION

PATENT NO.     : 6,448,283 B1
DATED          : September 10, 2002
INVENTOR(S)    : Jukka Ylikoski et al.

It is certified that error appears in the above-identified patent and that said Letters Patent is hereby corrected as shown below:

Column 53,
Line 12, please delete "$O(CH_2)_pOR$" and insert -- $O(CH_2)_pOR^{1b}$ -- therefor.

Column 54,
Line 30, please delete "$CHR^{20}$" and insert -- $CHR^{21}$ -- therefor.
Line 34, please delete "$CO_2R^{18}$" and insert -- $CO_2R^{18a}$ -- therefor.
Line 35, please delete "$C(=O)R^{18a} C(=O)NR^{18}CR^{18d}$" and insert
-- $C(=O)R^{18a} C(=O)NR^{18c}R^{18d}$ -- therefor.

Column 60,
Line 15, please delete "discloses" and insert -- disclosures -- therefor.

Column 62,
Lines 13-30, Table 2, at MEAN, forth column, please delete "547" and insert -- 847 -- therefor.

Column 64,
Line 29, Table 3, seventh column, please delete "ORC loss" and insert -- OHC loss -- therefor.
Line 30, Table 3, sixth column, please delete "ORC3" and insert -- OHC3 -- therefor.

Column 65,
Line 3, Table 3-continued, seventh column, please delete "ORC loss" and insert
-- OHC loss -- therefor.
Line 4, Table 3-continued, sixth column, please delete "ORC3" and insert -- OHC3 -- therefor.

Column 66,
Line 1, please delete "Nine to 1" and insert -- Nine to 11 -- therefor.

Column 71,
Line 33, please delete "63.9" and insert -- $\delta 3.9$ -- therefor.
Line 46, please delete "63.1" and insert -- $\delta 3.1$ -- therefor.

Column 72,
Line 30, please delete "64.15" and insert -- $\delta 4.15$ -- therefor.

UNITED STATES PATENT AND TRADEMARK OFFICE
CERTIFICATE OF CORRECTION

PATENT NO. : 6,448,283 B1
DATED : September 10, 2002
INVENTOR(S) : Jukka Ylikoski et al.

It is certified that error appears in the above-identified patent and that said Letters Patent is hereby corrected as shown below:

Column 74,
Line 46, please delete "$^1$H" and insert -- 1H -- therefor.
Line 58, please delete "sdium" and insert -- sodium -- therefor.

Column 75,
Line 8, please delete "stirre" and insert -- stirred -- therefor.
Line 9, please delete "thouroughly" and insert -- thoroughly -- therefor.

Column 83,
Line 39, please delete "homogeneious" and insert -- homogeneous -- therefor.

Column 87,
Line 41, please delete "O(CH$_2$)pNR$^{1c}$R$^{1d}$" and insert -- O(CH$_2$)$_p$NR$^{1c}$R$^{1d}$ -- therefor.
Line 51, please delete "(CH$_2$)pNR$^{1c}$R$^{1d}$" and insert -- (CH$_2$)$_p$NR$^{1c}$R$^{1d}$ -- therefor.
Line 67, please delete "C(=O)NR$^2$CR$^{2d}$" and insert -- C(=O)NR$^{2c}$R$^{2d}$ -- therefor.

Column 88,
Line 15, please delete "O(CH$_2$)$_p$OR$^{11}$" and insert -- O(CH$_2$)$_p$OR$^{10}$ -- therefor.
Line 58, please delete "S(=O)2" and insert -- S(=O)$_2$ -- therefor.
Line 63, please delete "C(R$^{21}$)$_2$" and insert -- C(R$^{20}$)$_2$ -- therefor.
Line 65, please delete "C(=O)NR$_{18c}$CR$^{18d}$" and insert -- C(=O)NR$^{18c}$R$^{18d}$ -- therefor.

Column 89,
Line 4, please delete "R$^{18a}$" and insert -- R$^{18c}$ -- therefor.
Line 32, please delete "C(=O)NR$^{1a}$, CR$^{1d}$" and insert -- C(=O)NR$^{1c}$R$^{1d}$ -- therefor.
Line 56, please delete "N(C(=O)R$^7$)" and insert -- N(C(=O)R$^{17}$) -- therefor.

Column 91,
Line 34, please delete "CH$_{20}$C(=O)NHCH$_2$CH$_3$" and insert
-- CH$_2$OC(=O)NHCH$_2$CH$_3$ -- therefor.

UNITED STATES PATENT AND TRADEMARK OFFICE
CERTIFICATE OF CORRECTION

PATENT NO. : 6,448,283 B1
DATED : September 10, 2002
INVENTOR(S) : Jukka Ylikoski et al.

It is certified that error appears in the above-identified patent and that said Letters Patent is hereby corrected as shown below:

Column 92,
Line 16, please delete "elected" and insert -- selected -- therefor.

Signed and Sealed this

Thirtieth Day of November, 2004

JON W. DUDAS
*Director of the United States Patent and Trademark Office*